(12) United States Patent
McMinn

(10) Patent No.: US 9,283,079 B2
(45) Date of Patent: Mar. 15, 2016

(54) CUP WITH CROSSLINKED POLYMER LAYER CABLE TIES

(71) Applicant: Derek James Wallace McMinn, West Midlands (GB)

(72) Inventor: Derek James Wallace McMinn, West Midlands (GB)

( * ) Notice: Subject to any disclaimer, the term of this patent is extended or adjusted under 35 U.S.C. 154(b) by 283 days.

(21) Appl. No.: 13/775,533

(22) Filed: Feb. 25, 2013

(65) Prior Publication Data
US 2013/0268083 A1    Oct. 10, 2013

Related U.S. Application Data

(60) Division of application No. 13/517,125, filed as application No. PCT/GB2010/002292 on Dec. 17, 2010, which is a continuation of application No. 12/819,540, filed on Jun. 21, 2010.

(30) Foreign Application Priority Data

Dec. 21, 2009 (GB) .................................. 0922339.7
Jan. 18, 2010 (GB) .................................. 1000744.1

(51) Int. Cl.
*A61F 2/32* (2006.01)
*A61F 2/34* (2006.01)
(Continued)

(52) U.S. Cl.
CPC .............. *A61F 2/34* (2013.01); *A61F 2/30771* (2013.01); *A61F 2/4609* (2013.01); *A61L 27/14* (2013.01); *A61L 27/50* (2013.01); *A61L 27/505* (2013.01); *B32B 1/00* (2013.01); *B32B 3/00* (2013.01); *B32B 7/12* (2013.01); *B32B 15/08* (2013.01); *C08J 3/00* (2013.01); *C08J 3/24* (2013.01); *A61F 2/3094* (2013.01); *A61F 2/38* (2013.01); *A61F 2002/30026* (2013.01);
(Continued)

(58) Field of Classification Search
CPC ......................... A61F 2/34; A61F 2002/3401
See application file for complete search history.

(56) References Cited

U.S. PATENT DOCUMENTS

| | | | |
|---|---|---|---|
| 4,520,511 A | 6/1985 | Gianezio et al. | |
| 5,133,757 A | 7/1992 | Sioshansi et al. | |

(Continued)

FOREIGN PATENT DOCUMENTS

| | | |
|---|---|---|
| DE | 3918970 A1 | 12/1990 |
| EP | 0681845 A2 | 11/1995 |

(Continued)

OTHER PUBLICATIONS

International Search Report and Written Opinion for International Application No. PCT/GB2012/000522 issued Jan. 24, 2013 and mailed Jan. 31, 2013, 7 pages.

(Continued)

*Primary Examiner* — Jason-Dennis Stewart
(74) *Attorney, Agent, or Firm* — Morgan, Lewis & Bockius LLP

(57) ABSTRACT

This invention related to a method of forming a polymer component and comprises blending polymer particles with antioxidant to form a mixture in which the antioxidant coats the polymer particles, irradiating the polymer particles to cross-link the polymer particles therein and forming the irradiated mixture into a consolidated component. The invention also relates to a method of forming an articular surface for a prosthesis and a prosthesis having a polymer articular bearing surface wherein at least one predetermined portion of the bearing surface is provided with cross-linked polymer bonds.

19 Claims, 45 Drawing Sheets

(51) Int. Cl.

| | | |
|---|---|---|
| A61F 2/30 | (2006.01) | |
| A61F 2/46 | (2006.01) | |
| A61L 27/14 | (2006.01) | |
| A61L 27/50 | (2006.01) | |
| B32B 1/00 | (2006.01) | |
| B32B 3/00 | (2006.01) | |
| B32B 7/12 | (2006.01) | |
| B32B 15/08 | (2006.01) | |
| C08J 3/00 | (2006.01) | |
| C08J 3/24 | (2006.01) | |
| A61F 2/38 | (2006.01) | |

(52) U.S. Cl.
CPC ............... *A61F 2002/3052* (2013.01); *A61F 2002/30112* (2013.01); *A61F 2002/30143* (2013.01); *A61F 2002/30331* (2013.01); *A61F 2002/30352* (2013.01); *A61F 2002/30378* (2013.01); *A61F 2002/30448* (2013.01); *A61F 2002/30462* (2013.01); *A61F 2002/30561* (2013.01); *A61F 2002/30685* (2013.01); *A61F 2002/30841* (2013.01); *A61F 2002/30878* (2013.01); *A61F 2002/30904* (2013.01); *A61F 2002/30971* (2013.01); *A61F 2002/30986* (2013.01); *A61F 2002/344* (2013.01); *A61F 2002/4681* (2013.01); *A61F 2220/005* (2013.01); *A61F 2220/0025* (2013.01); *A61F 2220/0033* (2013.01); *A61F 2220/0075* (2013.01); *A61F 2230/0004* (2013.01); *A61F 2230/0017* (2013.01); *B32B 2535/00* (2013.01); *C08J 2300/00* (2013.01)

(56) References Cited

U.S. PATENT DOCUMENTS

| | | | |
|---|---|---|---|
| 5,310,408 | A | 5/1994 | Schryver et al. |
| 5,639,280 | A | 6/1997 | Warner et al. |
| 5,645,594 | A | 7/1997 | Devanathan et al. |
| 5,766,255 | A | 6/1998 | Slamin et al. |
| 5,879,400 | A | 3/1999 | Merrill et al. |
| 5,879,404 | A | 3/1999 | Bateman et al. |
| 6,143,232 | A | 11/2000 | Rohr |
| 6,156,220 | A | 12/2000 | Ohlig |
| 6,165,220 | A | 12/2000 | McKellop et al. |
| 6,168,626 | B1 | 1/2001 | Hyon et al. |
| 6,217,615 | B1 | 4/2001 | Sioshansi et al. |
| 6,231,612 | B1 | 5/2001 | Balay et al. |
| 6,281,264 | B1 | 8/2001 | Salovey et al. |
| 6,290,727 | B1 | 9/2001 | Otto et al. |
| 6,365,089 | B1 | 4/2002 | Krebs et al. |
| 6,436,137 | B2 | 8/2002 | Wang et al. |
| 6,451,058 | B2 | 9/2002 | Tuke et al. |
| 6,494,917 | B1 | 12/2002 | McKellop et al. |
| 6,503,281 | B1 | 1/2003 | Mallory |
| 6,503,439 | B1 | 1/2003 | Burstein |
| 6,641,617 | B1 | 11/2003 | Merrill et al. |
| 6,652,586 | B2 | 11/2003 | Hunter et al. |
| 6,682,567 | B1 | 1/2004 | Schroeder |
| 6,709,464 | B2 | 3/2004 | Scott et al. |
| 6,746,452 | B2 | 6/2004 | Tuke et al. |
| 6,786,933 | B2 | 9/2004 | Merrill et al. |
| 6,794,423 | B1 | 9/2004 | Li |
| 6,800,670 | B2 | 10/2004 | Shen et al. |
| 6,818,171 | B2 | 11/2004 | Wang et al. |
| 6,849,224 | B2 | 2/2005 | Wang et al. |
| 6,905,511 | B2 | 6/2005 | Wang et al. |
| 7,169,186 | B2 | 1/2007 | Harris et al. |
| 7,186,362 | B2 | 3/2007 | Wang et al. |
| 7,205,339 | B2 | 4/2007 | Muratoglu |
| 7,288,115 | B2 | 10/2007 | Hawkins |
| 7,304,097 | B2 | 12/2007 | Muratoglu et al. |
| 7,344,672 | B2 | 3/2008 | Schroeder et al. |
| 7,364,685 | B2 | 4/2008 | Schmotzer |
| 7,381,752 | B2 | 6/2008 | Muratoglu |
| 7,384,430 | B2 | 6/2008 | Greer et al. |
| 7,431,874 | B2 | 10/2008 | Muratoglu et al. |
| 7,473,279 | B2 | 1/2009 | Baege et al. |
| 7,498,365 | B2 | 3/2009 | Muratoglu et al. |
| 7,507,774 | B2 | 3/2009 | Muratoglu et al. |
| 7,569,620 | B2 | 8/2009 | Muratoglu et al. |
| 7,714,036 | B2 | 5/2010 | Wang et al. |
| 7,785,372 | B2 | 8/2010 | Ishihara et al. |
| 7,790,095 | B2 | 9/2010 | Muratoglu et al. |
| 7,790,779 | B2 | 9/2010 | Muratoglu |
| 7,819,925 | B2 | 10/2010 | King et al. |
| 7,831,752 | B2 | 11/2010 | Illowsky et al. |
| 7,833,274 | B2 | 11/2010 | Popoola et al. |
| 7,833,452 | B2 | 11/2010 | Muratoglu et al. |
| 7,846,376 | B2 | 12/2010 | Abt et al. |
| 7,863,348 | B2 | 1/2011 | Abt et al. |
| 7,883,653 | B2 | 2/2011 | Smith et al. |
| 7,896,921 | B2 | 3/2011 | Smith et al. |
| 7,906,064 | B2 | 3/2011 | Muratoglu et al. |
| 7,955,393 | B2 | 6/2011 | Hawkins |
| 2001/0011190 | A1 | 8/2001 | Park |
| 2001/0027345 | A1 | 10/2001 | Merrill et al. |
| 2001/0049401 | A1 | 12/2001 | Salovey et al. |
| 2002/0002246 | A1 | 1/2002 | Wang et al. |
| 2002/0007219 | A1 | 1/2002 | Merrill et al. |
| 2002/0093124 | A1 | 7/2002 | Wang et al. |
| 2002/0161438 | A1 | 10/2002 | Scott et al. |
| 2002/0177854 | A1 | 11/2002 | Tuke et al. |
| 2003/0009230 | A1 | 1/2003 | Gundlapalli et al. |
| 2003/0130743 | A1 | 7/2003 | Scott et al. |
| 2003/0139555 | A1 | 7/2003 | Hubbard et al. |
| 2003/0144741 | A1 | 7/2003 | King et al. |
| 2003/0149125 | A1 | 8/2003 | Muratoglu et al. |
| 2003/0208278 | A1 | 11/2003 | Richard |
| 2003/0212161 | A1 | 11/2003 | McKellop et al. |
| 2003/0212458 | A1 | 11/2003 | Harris et al. |
| 2004/0019380 | A1 | 1/2004 | Baege et al. |
| 2004/0051213 | A1 | 3/2004 | Muratoglu |
| 2004/0054418 | A1 | 3/2004 | McLean et al. |
| 2004/0098127 | A1 | 5/2004 | Charlebois et al. |
| 2004/0132856 | A1 | 7/2004 | Merrill et al. |
| 2004/0156879 | A1 | 8/2004 | Muratoglu et al. |
| 2004/0210316 | A1 | 10/2004 | King et al. |
| 2005/0006821 | A1 | 1/2005 | Merrill et al. |
| 2005/0010288 | A1 | 1/2005 | Merrill et al. |
| 2005/0043815 | A1 | 2/2005 | King et al. |
| 2005/0048096 | A1 | 3/2005 | Shen et al. |
| 2005/0069696 | A1 | 3/2005 | King et al. |
| 2005/0070625 | A1 | 3/2005 | Hubbard et al. |
| 2005/0096749 | A1 | 5/2005 | Marrill et al. |
| 2005/0113935 | A1 | 5/2005 | Wang et al. |
| 2005/0125074 | A1 | 6/2005 | Salovey et al. |
| 2005/0146070 | A1 | 7/2005 | Muratoglu et al. |
| 2005/0149198 | A1 | 7/2005 | Hawkins |
| 2005/0165495 | A1 | 7/2005 | Merrill et al. |
| 2005/0194722 | A1 | 9/2005 | Muratoglu et al. |
| 2005/0194723 | A1 | 9/2005 | Muratoglu et al. |
| 2005/0267594 | A1 | 12/2005 | Merrill et al. |
| 2006/0079595 | A1 | 4/2006 | Schroeder et al. |
| 2006/0149387 | A1 | 7/2006 | Smith et al. |
| 2006/0149388 | A1 | 7/2006 | Smith et al. |
| 2006/0155383 | A1 | 7/2006 | Smith et al. |
| 2006/0264541 | A1 | 11/2006 | Lederer et al. |
| 2006/0293686 | A1* | 12/2006 | Wozencroft .......... A61F 2/4609 606/91 |
| 2007/0043137 | A1 | 2/2007 | Muratoglu et al. |
| 2007/0059334 | A1 | 3/2007 | Abt et al. |
| 2007/0067044 | A1 | 3/2007 | Hanes et al. |
| 2007/0093909 | A1 | 4/2007 | King |
| 2007/0100016 | A1 | 5/2007 | Shen |
| 2007/0100017 | A1 | 5/2007 | Shen et al. |
| 2007/0114702 | A1 | 5/2007 | Muratoglu et al. |
| 2007/0135927 | A1 | 6/2007 | Harris et al. |
| 2007/0173948 | A1 | 7/2007 | Meridew et al. |
| 2007/0191504 | A1 | 8/2007 | Muratoglu |
| 2007/0219562 | A1* | 9/2007 | Slone ................ A61F 2/34 606/99 |

(56) References Cited

U.S. PATENT DOCUMENTS

| | | | |
|---|---|---|---|
| 2007/0265369 A1 | 11/2007 | Muratoglu et al. | |
| 2007/0267030 A1 | 11/2007 | Muratoglu et al. | |
| 2007/0293647 A1 | 12/2007 | McKellop et al. | |
| 2008/0036111 A1 | 2/2008 | Sun | |
| 2008/0039545 A1 | 2/2008 | Muratoglu et al. | |
| 2008/0067724 A1 | 3/2008 | Muratoglu et al. | |
| 2008/0071026 A1 | 3/2008 | King et al. | |
| 2008/0090934 A1 | 4/2008 | Muratoglu et al. | |
| 2008/0119582 A1 | 5/2008 | Muratoglu et al. | |
| 2008/0208350 A1 | 8/2008 | Roger | |
| 2008/0214692 A1 | 9/2008 | Muratoglu et al. | |
| 2008/0215142 A1 | 9/2008 | Muratoglu et al. | |
| 2008/0262120 A1 | 10/2008 | Muratoglu | |
| 2008/0319137 A1 | 12/2008 | Rufner et al. | |
| 2009/0030524 A1 | 1/2009 | Schroeder et al. | |
| 2009/0048679 A1 | 2/2009 | Howald et al. | |
| 2009/0118390 A1 | 5/2009 | Abt et al. | |
| 2009/0192610 A1 | 7/2009 | Case et al. | |
| 2009/0243159 A1 | 10/2009 | Sun | |
| 2009/0265001 A1 | 10/2009 | Muratoglu et al. | |
| 2010/0029858 A1 | 2/2010 | Rufner et al. | |
| 2010/0036491 A1 | 2/2010 | He et al. | |
| 2010/0082101 A1 | 4/2010 | Muratoglu et al. | |
| 2010/0137481 A1 | 6/2010 | Shen et al. | |
| 2010/0161072 A1* | 6/2010 | Drescher | 623/22.29 |
| 2010/0190882 A1 | 7/2010 | Muratoglu et al. | |
| 2010/0190920 A1 | 7/2010 | Bellare | |
| 2010/0262251 A1 | 10/2010 | Muratoglu et al. | |
| 2011/0004315 A1 | 1/2011 | Muratoglu et al. | |
| 2011/0015753 A1* | 1/2011 | Meridew | A61F 2/34 623/22.24 |
| 2011/0028600 A1 | 2/2011 | Rufner et al. | |
| 2011/0039014 A1 | 2/2011 | King et al. | |
| 2011/0077743 A1 | 3/2011 | Smith et al. | |
| 2011/0104003 A1 | 5/2011 | Muratoglu et al. | |
| 2011/0109017 A1 | 5/2011 | Muratoglu et al. | |
| 2011/0112646 A1 | 5/2011 | Brunner et al. | |
| 2011/0133371 A1 | 6/2011 | Rufner et al. | |
| 2011/0136933 A1 | 6/2011 | Abt et al. | |
| 2011/0153025 A1 | 6/2011 | McMinn | |
| 2012/0319332 A1 | 12/2012 | McMinn | |
| 2013/0268084 A1 | 10/2013 | McMinn | |
| 2014/0207245 A1 | 7/2014 | McMinn | |

FOREIGN PATENT DOCUMENTS

| | | |
|---|---|---|
| EP | 0761242 A1 | 3/1997 |
| EP | 1216667 A1 | 6/2002 |
| EP | 1297800 A2 | 4/2003 |
| EP | 1353977 A2 | 10/2003 |
| EP | 0850606 B1 | 5/2004 |
| EP | 1421918 A1 | 5/2004 |
| EP | 1 634 551 | 3/2006 |
| EP | 1 634 552 | 6/2006 |
| EP | 1676548 A1 | 7/2006 |
| EP | 1681036 A1 | 7/2006 |
| EP | 2189135 A1 | 5/2010 |
| FR | 2803192 A1 | 7/2001 |
| FR | 2803740 A1 | 7/2001 |
| GB | 2246957 A | 2/1992 |
| GB | 2323036 A | 9/1998 |
| GB | 2476319 A | 6/2011 |
| WO | WO-94/05234 A1 | 3/1994 |
| WO | WO9421199 | 9/1994 |
| WO | WO-98/14223 A1 | 4/1998 |
| WO | WO-99/52474 A1 | 10/1999 |
| WO | WO-0049079 A1 | 8/2000 |
| WO | WO-0248259 A2 | 6/2002 |
| WO | WO-02/069819 A2 | 9/2002 |
| WO | WO-2004/032987 A1 | 4/2004 |
| WO | WO-2007019874 A1 | 2/2007 |
| WO | WO-2007108848 A1 | 9/2007 |
| WO | WO-2008/080595 A2 | 7/2008 |
| WO | WO-2008/092047 A1 | 7/2008 |
| WO | WO2008103457 | 8/2008 |
| WO | WO-2008/124824 A1 | 10/2008 |
| WO | WO-2009032909 A2 | 3/2009 |
| WO | WO-2009/138103 A1 | 11/2009 |
| WO | WO-2010/096771 A2 | 8/2010 |
| WO | WO-2010/135526 A2 | 11/2010 |
| WO | WO-2011077074 A1 | 6/2011 |
| WO | WO-2012172293 A2 | 12/2012 |

OTHER PUBLICATIONS

Australian Office Action dated Feb. 7, 2013, for Australian Patent Application No. 2010334670, Earliest Priority Date, Dec. 21, 2009; Examination Request Date, Aug. 31, 2012, 4 pages.

Australian Office Action dated Oct. 14, 2013, for Australian Patent Application No. 2013200902, Earliest Priority Date, Dec. 21, 2009, Examination Request Date, Feb. 19, 2013, 4 pages.

Australian Office Action dated Oct. 21, 2013, for Australian Patent Application No. 2013200906, Earliest Priority Date, Dec. 21, 2009, Examination Request Date, Feb. 19, 2013, 6 pages.

United States Office Action dated Nov. 15, 2012, for U.S. Appl. No. 12/819,540, 8 pages.

United States Office Action dated Jun. 13, 2013, for U.S. Appl. No. 12/819,540, 5 pages.

United States Office Action dated Jul. 8, 2014, for U.S. Appl. No. 12/819,540, 8 pages.

British Search Report dated May 7, 2013, for Great Britain Application No. 1307451.3, 5 pages.

International Search Report and Written Opinion mailed Jun. 27, 2014 for International Application No. PCT/GB2014/051211 (10 pages).

Tomita N. et al. "Prevention of fatigue cracks in ultrahigh molecular weight polyethylene joint components by the addition of vitamin E." J Biomed Mater Res. 1999;48(4):474-8.

Parth M. et al. "Studies on the effect of electron beam radiation on the molecular structure of ultra-high molecular weight polyethylene under the influence of alpha-tocopherol with respect to its application in medical implants." J Mater Sci Mater Med. Oct. 2002;13(10):917-21.

International Search Report and Written Opinion mailed Apr. 1, 2011 for International Application No. PCT/GB2010/002292 (13 pages).

International Search Report mailed Jan. 5, 2011 for United Kingdom Application No. GB1000744.1 (2 pages).

International Search Report mailed Jan. 6, 2011 for United Kingdom Application No. GB1000744.1 (1 page).

Oral, et al. "Surface Cross-linked UHMWPE: The Holy Grail in Arthroplasty," Massachusetts General Hospital, Dept. of Ortho. Surg. (2 pages).

Chinese Office Action dated Feb. 26, 2014, for Chinese Patent Application No. 2010800641890, 4 pages.

Chinese Office Action dated Jun. 3, 2015 for corresponding Chinese Patent Application No. 201280039688.3.

Chinese Office Action dated May 27, 2015 for corresponding Chinese Patent Application No. 201410014686.X.

Office Action issued in a related U.S. Appl. No. 13/517,125 dated Oct. 6, 2015.

Office Action issued in a related U.S. Appl. No. 13/776,022 dated Oct. 7, 2015.

* cited by examiner

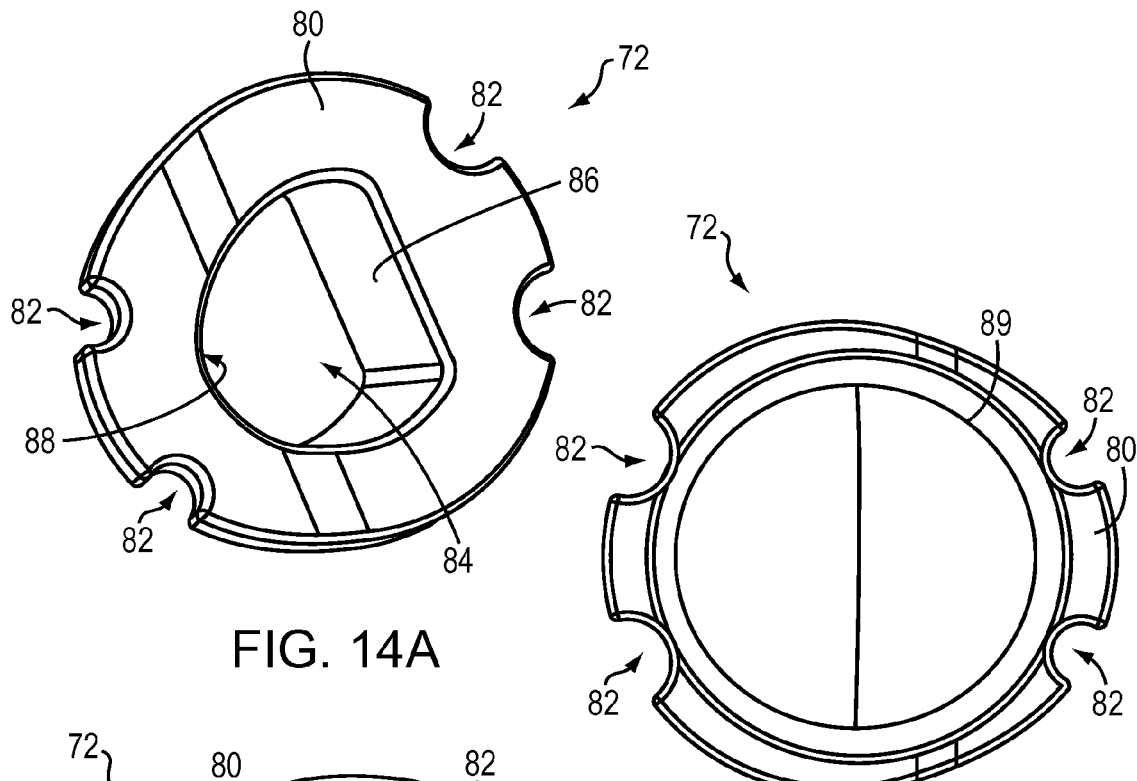
FIG. 14A
FIG. 14B
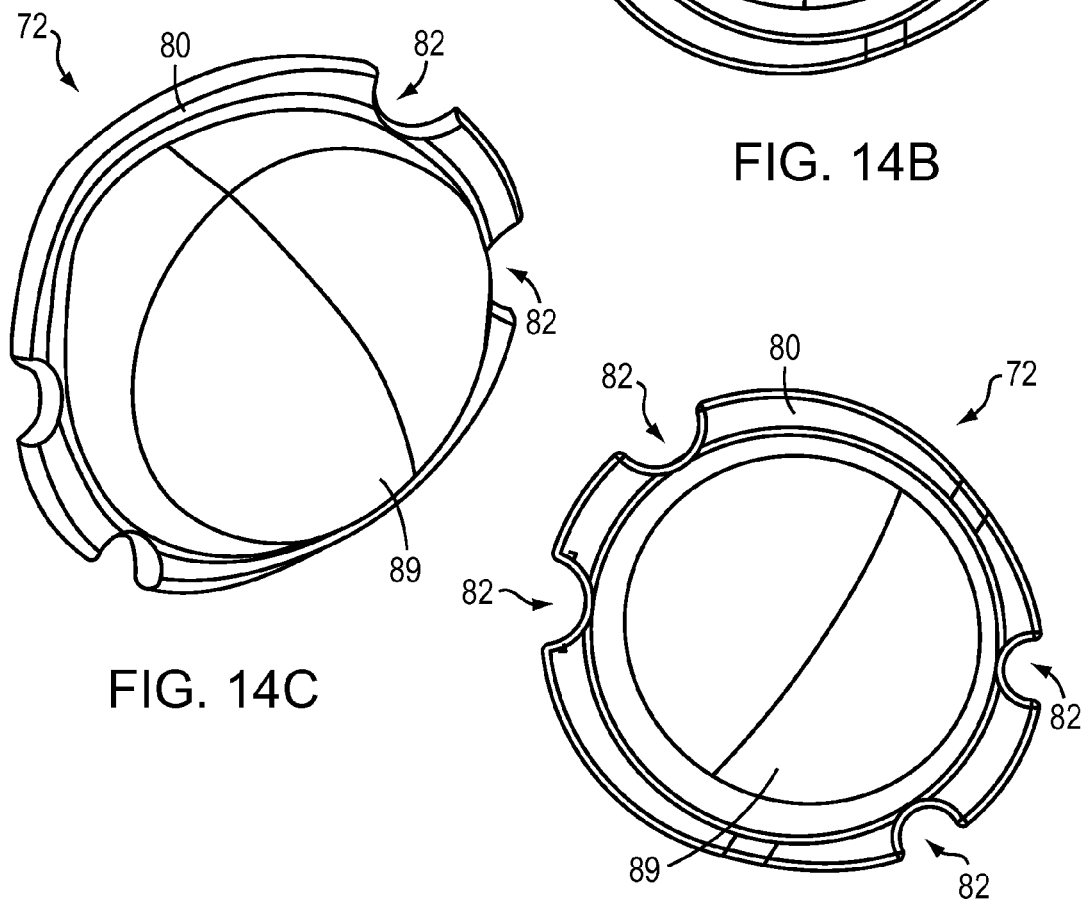
FIG. 14C
FIG. 14D

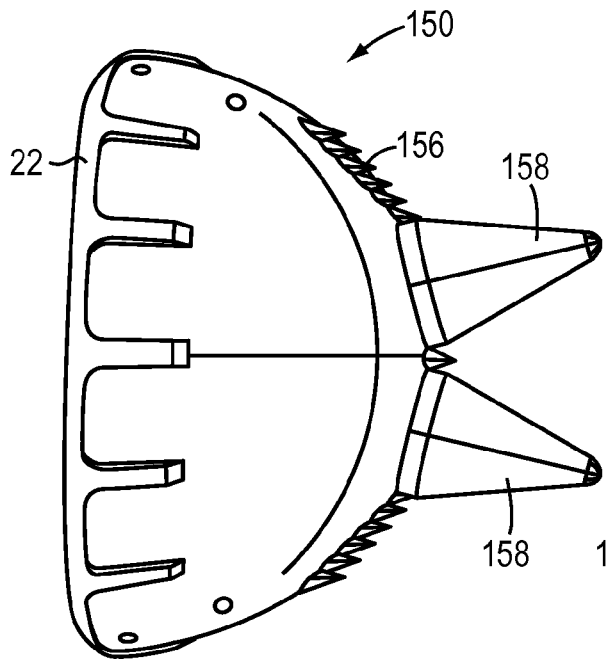
FIG. 25A
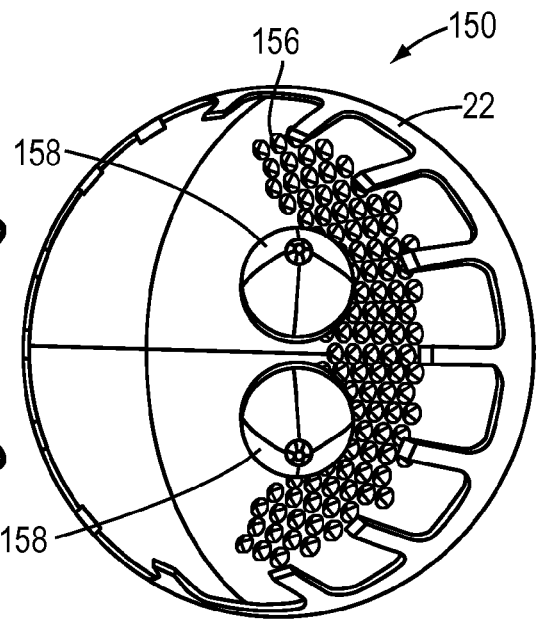
FIG. 25B
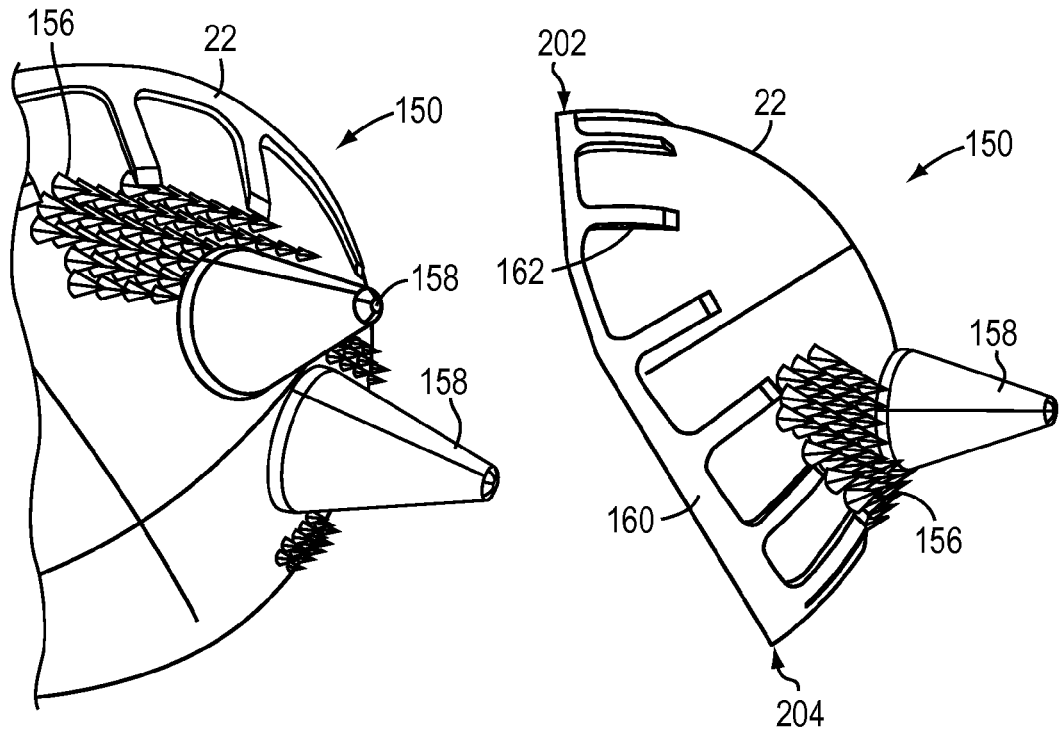
FIG. 25C
FIG. 25D

CUP WITH CROSSLINKED POLYMER LAYER CABLE TIES

RELATED APPLICATIONS

This application is a divisional of U.S. patent application Ser. No. 13/517,125, filed Aug. 27, 2012, which is a U.S. National Phase Application of PCT/GB 2010/002292, filed Dec. 17, 2010, which claims priority to and the benefit of United Kingdom Patent Application No. 0922339.7, filed on Dec. 21, 2009, United Kingdom Patent Application No. 1000744.1, filed Jan. 18, 2010, and U.S. patent application Ser. No. 12/819,540, filed Jun. 21, 2010, all of which are incorporated herein by reference.

FIELD OF THE INVENTION

This invention relates to a method of forming a polymer component. Particularly, but not exclusively, the invention relates to a method of forming a polymer component for a prosthesis such as an acetabular cup prosthesis for use in hip resurfacing.

BACKGROUND TO THE INVENTION

Hip resurfacing is commonly performed using acetabular cups and femoral components which are made from solid metal. However, it has been estimated that approximately 1% of patients who undergo such metal-on-metal hip resurfacing have a pseudo-tumour in the form of a soft tissue mass or large symptomatic effusion within 5 years. The symptoms of these pseudo-tumours include discomfort, spontaneous dislocation, nerve palsy, a noticeable mass and a rash, while the common histological features are extensive necrosis and lymphocytic infiltration. As a consequence, many patients require revision surgery followed by conventional total hip replacement.

Whilst the cause of these pseudo-tumours is currently unconfirmed, it has been observed that they occur in situations of high bearing wear. This could be caused by poor wearing metal as a result of non-optimal heat treatment during processing or due to component misalignment, which may either result from the surgeon mal-positioning one or more of the components or from an underlying bony misalignment of the skeleton (e.g. developmental dysplasia of the hip). Edge wear of the acetabular component has also been observed along with excessive wear of the femoral component due to impingement.

It is believed that the pseudo-tumours may, in fact, be due to a toxic reaction to an excess of particulate metal wear debris or metal ions or, perhaps, a hypersensitivity reaction to a normal amount of metal wear debris. There is therefore a concern that, with time, the incidence of these pseudo-tumours may increase.

Other materials have been considered for use in hip resurfacing. For example, a metal outer cup shell has been combined with a polymer (e.g. conventional non cross-linked polyethylene) inner cup liner. However, in these instances an even higher failure rate is encountered because wear of the bearing surface leads to early loosening of the joint and the production of large quantities of polymer debris. This results in osteolysis of the acetabulum and femur making revision surgery difficult due to the loss of bone stock.

Commonly, acetabular cups are configured for press-fit fixation (e.g. by forcing a 50 mm outer diameter component into a 48 mm diameter hole). This can result in considerable deformation (e.g. in the range of 100 microns to over 350 microns), even where thick metal shells are employed, and so there is a risk that the cup will grip the femoral component leading to early acetabular component breakout. Alternative fixation features, such as large projecting pegs, are therefore sometimes employed. To aid fixation of these components, the external surface of the cup is often provided with a porous coating (e.g. by plasma spraying titanium particles) to encourage bone in-growth. However, such a coating only tends to provide limited contact between the bone and the metal coating leading to poor grip. In addition, the titanium particles can easily become dislodged, such that they then serve as abrasive debris.

It is therefore an aim of the present invention to provide a method of forming a polymer component (e.g. for a prosthesis such as an acetabular cup prosthesis), which helps to ameliorate some of all of the afore-mentioned problems.

SUMMARY OF THE INVENTION

According to a first aspect of the present invention there is provided a method of forming a polymer component comprising:
blending polymer particles with antioxidant to form a mixture in which the antioxidant coats the polymer particles;
irradiating the polymer particles to cross-link molecules therein; and forming the irradiated mixture into a consolidated component.

The step of blending the polymer particles with antioxidant may be performed before, during or after the step of irradiating the polymer particles to cross-link the molecules therein.

It will be understood that the step of blending the polymer particles with antioxidant will occur before the irradiated mixture is formed into a consolidated component.

The method may further comprise the step of reducing or substantially eliminating the presence of oxygen in or between the polymer particles. This step may be performed prior to or during irradiation and/or when forming the irradiated mixture into a consolidated component.

The cross-linking of polymer material (e.g. polyethylene) has previously been performed by irradiating bar stock or a finished product after consolidation. Free radicals are an unwanted by-product of this process and commonly re-melting of the cross-linked polymer is performed to eliminate the free radicals. However, the mechanical properties of the polymer have been found to deteriorate as a result of re-melting.

It is also known to irradiate polythene resin (powder, particles or flakes) in air or a reduced oxygen atmosphere so as to minimise free radical formation during cross-linking to thereby try to eliminate the need for re-melting. After the polythene resin has been cross-linked the material is consolidated (e.g. by compression moulding) and this step further helps to eliminate free radicals due to the application of heat and pressure. The problem with this approach, however, is that the very large surface area of the polyethylene resin permits oxidation of the material during or after irradiation, even when irradiation is carried out in a reduced oxygen atmosphere. It is believed that one reason for this problem of oxidation during irradiation or during subsequent moulding of the irradiated particles is that approximately 5% oxygen can be contained within the polymer (e.g. polyethylene) particles (e.g. in the interstices thereof). The free radicals produced during irradiation can thus combine with the oxygen contained in the polymer particles. The resulting oxidized polymer is of a poor quality since it will be susceptible to severe wear and fracture due to mechanical weakening.

Embodiments of the present invention solve the problems outlined above by initially reducing or eliminating the oxygen in the polymer particles, prior to irradiation. This may be done by storing the polymer particles in a container providing an inert gas atmosphere (e.g. nitrogen) for a period of time (e.g. hours, days or weeks). The inert gas in the container with the polymer particles may be changed on a plurality of occasions to assist oxygen diffusion from the polymer particles. Alternatively, storage of the polymer particles in a vacuum may assist the diffusion of oxygen out of the polymer particles. Although the above methods serve to reduce the oxygen concentration in the polymer particles. it is near impossible to reduce the oxygen concentration to zero. Since there will likely remain a finite concentration of oxygen in the polymer particles, it is a further object of the invention to blend antioxidant (e.g. vitamin E) with the polymer particles, before, during or after irradiation to prevent or reduce oxidation by combination of any remnant oxygen with free radicals produced as a consequence of the cross-linking irradiation. It will be understood that the step of blending the polymer particles with antioxidant will be performed until the antioxidant substantially coats the surfaces of all of the polymer particles.

The step of forming the irradiated mixture into a consolidated component may comprise use of direct compression moulding, ram extrusion or compression moulding.

It is known in compression moulding or direct compression moulding to introduce reptations in order to more completely fuse together polymer particles (e.g. polymer powder). Typically during a moulding cycle the compression pressure is relaxed several times. A common regimen is to apply pressure for 1 minute, then relax the compression pressure for 1 minute, then apply pressure for 1 minute, this cycle being repeated between 3 and 6 times. This has been found to expel air more completely from between the polymer particles and to ensure that the particles are more tightly packed together giving improved mechanical properties. The applicant has devised a method of applying mechanical vibrations or more preferably ultrasound energy to the moulding apparatus in order to assist in a more complete expulsion of air from between the polymer particles and to ensure a tighter packing of the polymer particles.

The applicant has further devised a method for enclosing the moulding apparatus in a chamber which is subjected to a vacuum. The object is to remove air and oxygen which has been displaced from between the polymer particles in order to minimise the opportunity for oxidation to occur.

According to the known art, if an antioxidant blended polymer powder is consolidated by heat and pressure (e.g. by compression moulding) the antioxidant (e.g. vitamin E) will diffuse from the surface of the polymer powder into every molecule of the polymer under the influence of heat from the consolidation process. In the case of polyethylene the diffusion is into the loosely formed, amorphous phase of each polyethylene molecules (which accounts for about 50% of each polyethylene molecule). The crystalline phase is much tighter packed and harder to diffuse substances into. When the antioxidant containing consolidated polyethylene cools and is irradiated the antioxidant hinders cross-linking for the following reasons. It is the amorphous phase that is largely involved in cross-linking. Irradiation normally results in cross-linking by causing scissions in the polyethylene molecular chains. These scissions have free radicals on the ends of the broken chains. The broken ends tend to link with other surrounding molecular chain ends or sides so producing a cross-linked structure. However, when antioxidant is present in the amorphous phase, the antioxidant neutralises the free radicals on the broken chain ends, thus inhibiting cross-linking.

With the present invention, it is the polymer particles that are irradiated rather than a consolidated component. When blending of the polymer particles with antioxidant occurs before irradiation, then, as the blended polymer has not been heated prior to irradiation, the antioxidant will be substantially on the surface of the polymer particles. The irradiation will therefore cause uninhibited cross-linking inside the polymer particles. However, on the surface of the polymer particles the antioxidant will prevent oxidation.

When the irradiated mixture of the present invention is consolidated, the antioxidant is allowed to diffuse into the amorphous phase of each polymer molecule, for example under the influence of heat. It is noted that, when hot, antioxidants (e.g. vitamin E) are relatively inactive. It is also noted that during heating the cross-links tend to break up and when cooling starts the cross-links start to reform. Free radicals are also eradicated during this heating and cooling phase of consolidation of the polymer and instead of remaining as free radicals, they are involved in further cross-linking of the polymer chains. On cooling, the extensive cross-linking joins what were individual polymer particles into a homogenous mass, thus eliminating fusion defects. When the consolidated polymer cools to approximately 37 degrees C., the antioxidant (e.g. vitamin E) becomes fully active again, although in certain embodiments the process of heating and cooling has been found to destroy approximately 50% of the antioxidant activity.

It is the case that using the known art, whereby vitamin E is blended with polyethylene powder, then consolidated by heat and pressure and then cooled to ambient temperature, vitamin E in the amorphous phase inhibits radiation induced cross-linking of the consolidated polymer. There is therefore a delicate balance to be struck in providing enough vitamin E to neutralise the free radicals that are produced as an unwanted by product of cross-linking, but not too high a concentration of vitamin E to inhibit cross-linking. If the concentration of vitamin E is too low, then all of the vitamin E may be consumed in neutralising free radicals produced as an unwanted by product of irradiation. In this eventuality, no vitamin E will be available to neutralise free radicals produced by further irradiation (e.g. during a sterilisation process) or by stress-induced cross-link breakdown during use.

It is possible to modify the known art, by heating the consolidated polymer prior to and/or during irradiation so that during irradiation the antioxidant is substantially reversibly inactivated, thus allowing radiation induced cross-linking.

It is a great advantage of the present invention that cross-linking is not inhibited by having a high concentration of antioxidant. In fact, high concentrations of antioxidant can be advantageous in significantly reducing the amount of oxidation of the polymer. Furthermore, the applicants have found that the same cross-link density can be obtained using two very different amounts of antioxidant and so it has been determined that a high concentration of antioxidant on the polymer particle surfaces does not inhibit cross-linking.

A possible disadvantage of the above method whereby antioxidant is blended with the polymer particles followed by cross-linking irradiation, is that the antioxidant is subjected to high doses of radiation. There is currently concern that irradiation of antioxidant may produce harmful by-products. The applicant has surprisingly found, however, that the antioxidant blending of polymer particles can be performed after irradiation and before moulding with heat and pressure into the consolidated product. By this method, oxidation is still prevented, but the antioxidant is not subjected to high doses of cross-linking irradiation. In order to totally (or substantially)

eliminate the occurrence of irradiation of antioxidant blended with the consolidated polymer product, radiation sterilization should be substituted with either gas plasma or ethylene oxide sterilization.

The applicant also believes that the antioxidant may not be needed after the consolidation step, since the heat that may be required for consolidation may eliminate all free radicals. However, if a low dose of irradiation was to be used on the consolidation (e.g. to sterilise the final component), free radicals would be formed during this process and the antioxidant would neutralise these free radicals and prevent oxidation in use. Further, high contact stress in use can cause breakdown of some cross-links and exposure of free radicals. The antioxidant in the final product can therefore act as a safeguard preventing oxidation in this eventuality by neutralising any free radicals formed.

In certain embodiments of the present invention, the antioxidant (e.g. vitamin E) may constitute up to 3% of the weight of the mixture. In particular embodiments, the antioxidant (e.g. vitamin E) may constitute 0.1%, 0.5%, 1%, 2%, or 3% of the weight of the mixture.

The step of forming the irradiated mixture into a consolidated component may comprise the use of heat and/or pressure (e.g. by performing hot or cold compression moulding). Where heat is employed in the consolidation process, it will be understood that any free radicals present in the irradiated mixture will be eliminated or minimised, thus obviating the need for re-melting or annealing and thereby maintaining good mechanical properties of the consolidated material. Furthermore, as the consolidated component contains antioxidant, any free radicals generated during future use of the component will tend to be neutralised by the antioxidant.

The polymer particles may be provided in the form of a resin (e.g. comprising powder, flakes and/or small pellets) or a hydrogel (e.g. comprising a polymer capable of absorbing water).

The antioxidant may be provided in the form of a liquid, powder, solution or suspension. For example, a powder (or liquid) antioxidant may be dissolved in a solvent such as alcohol to increase the volume of the antioxidant containing element and allow it to more easily coat the polymer particles. The solvent may be evaporated off after the blending. Alternatively, for example for insoluble antioxidants, the bulk of the antioxidant containing element can be increased by placing the antioxidant in a suspension of liquid (e.g. water).

The polymer particles may comprise a plurality of molecules.

The polymer particles may comprise the following but are not limited thereto: polyethylene, polypropylene, polyamide, polyimide, polyether ketone, or any polyolefin, including high-density-polyethylene, low-density-polyethylene, linear-low-density-polyethylene, ultra-high molecular weight polyethylene (UHMWPE), copolymers and mixtures thereof; hydrogels such as poly(vinyl alcohol), poly(ethylene glycol), poly(ethylene oxide), poly(acrylic acid), poly(methacrylic acid), poly(acrylamide), copolymers and mixtures thereof; copolymers and mixtures of a hydrogels with any polyolefin.

The antioxidant may comprise the following but is not limited thereto: vitamin E; alpha-tocopherol, delta-tocopherol; propyl, octyl, or dedocyl gallates; lactic, citric, ascorbic, tartaric acids; organic acids and their salts; orthophosphates; tocopherol acetate and Irganox 1010.

The method may further comprise the step of processing the consolidated component, for example, using high pressure and/or high temperature crystallization. This may have the advantage of further improving the mechanical properties of the consolidated component.

The consolidated component may form a product, a part of a product, or bar stock from which a product or a part of a product may be made (e.g. machined). The product may be constituted by a bearing component, a medical device, or a prosthesis. The prosthesis may be configured for use in any joint, for example, the hip, knee, spine, neck, ankle, toe, shoulder, elbow, wrist, finger or thumb.

Where the consolidated component forms a part of a product, the part may form a surface of the product, in particular, a surface that is normally expected to be subjected to wear (e.g. a bearing surface). The part may constitute the whole or a part of at least one surface of a product, such as an articular surface of a prosthesis.

Thus, a component formed by the present method may be used in partial articular surface cross-linking (as will be disclosed in detail in this application), full articular surface cross-linking, both the front and back elements of modular polymer bearing inserts to reduce front and back wear, both front and back elements of inserts for dual mobility hip bearings to reduce wear on both sides, and full component cross-linking by forming the component using direct compression moulding (exploiting the good mechanical properties of the material).

In embodiments of the invention, the component may be direct compression moulded into a porous or non-porous shell or backing material. The shell or backing material may be suitable for contacting bone (e.g. may be formed from metal, ceramic or polymer). The shell or backing material may be formed by, for example, casting, forging or machining from bar stock (e.g. for a metal shell), or injection moulding or compression moulding (e.g. for a polymer shell).

The present method may used to form bulk material (i.e. wherein the consolidated component of the first aspect of the invention is in the form of bulk material, e.g. in the form of large compression moulded sheets or long ram extruded rods). The step of forming the bulk material may therefore be by compression moulding, ram extrusion or other known methods. Products such as implants (or parts therefor) may then be machined from the bulk material.

In certain embodiments of the invention, irradiation of the polymer powder (with or without blended antioxidant) is carried out in the presence of a sensitizing gas or liquid (e.g. acetylene).

The method according to the first aspect of the invention may be configured for forming an articular surface (or a part of an articular surface) for an acetabular cup prosthesis. In which case, the articular surface may be configured as a liner for an acetabular cup configured for use in either total hip replacement or hip resurfacing. In specific embodiments, the articular surface may be configured for use in an acetabular cup comprising any of the features described below in relation to the fifth to fifteenth aspects of the present invention.

According to a second aspect of the present invention there is provided a method of forming an articular surface for a prosthesis comprising:

forming a first layer comprising a first polymer;
forming a second layer comprising a second polymer, wherein the second layer constitutes the whole or a part of an articular surface layer;
joining the first and second layers together to form an articular surface component;
irradiating the second polymer to cross-link the molecules therein; and facilitating the consumption of free radicals in the second layer to thereby minimise the risk of oxidation of the second layer.

The first and second polymers may be the same or different prior to the step of irradiation.

The first layer may further comprise an antioxidant. The antioxidant may comprise the following but is not limited thereto: vitamin E; alpha-tocopherol, delta-tocopherol; propyl, octyl, or dedocyl gallates; lactic, citric, ascorbic, tartaric acids; organic acids and their salts; orthophosphates; tocopherol acetate and Irganox 1010. The first layer may include at least 1% by weight of vitamin E. In a first embodiment, the first layer may include 2% by weight of vitamin E. In a second embodiment, the first layer may include 3% by weight of vitamin E. It will be noted that the amount of antioxidant provided in the first layer may be selected so as to prevent cross-linking of the first layer when the second polymer is irradiated.

It will be understood that since the second layer is intended to be cross-linked, it may be desirable that no antioxidant is present in this layer. However, in practice, a small amount of antioxidant may nevertheless be present in this layer as long as it is not sufficient to significantly prevent the formation of cross-linked bonds in the second layer. Thus, a low concentration of antioxidant (e.g. vitamin E) of, say, less than 0.2%, may be present in the second layer. For example, the second layer may contain 0.05% or 0.1% of antioxidant (e.g. vitamin E).

The step of facilitating the consumption of free radicals in the second layer may be performed by ensuring that the concentration of antioxidant in the second layer is low enough to allow polymer cross-linking with radiation but high enough to consume the free radicals generated as a result of the radiation.

It will be understood that the step of joining the first and second layers together may comprise the application of heat and/or pressure. Thus, the first and second layers may be joined by hot compression moulding. Alternatively, they may be cold compression moulded or joined by an adhesive or mechanical means.

The second polymer may be irradiated before or after it is formed into the second layer. Thus, the second layer may be formed in accordance with the first aspect of the present invention (i.e. by coating the second polymer with antioxidant, before or after the polymer is irradiated, and then forming the irradiated mixture into the second layer). Additionally or alternatively, the second polymer may be irradiated after the second layer has been joined to the first layer.

It may be advantageous to irradiate the second polymer prior to the second layer being joined to the first layer, since this may negate the need to alter the first polymer (e.g. by mixing it with an antioxidant) so as to prevent the first polymer from cross-linking, thereby weakening the first layer. Alternatively, irradiating the second polymer prior to the second layer being joined to the first layer could mean that after the first and second layers are joined only a low dose of radiation is required to obtain the desired amount of cross-linking in the second layer—thus, again, minimizing damage to the first layer as a result of the radiation.

The second polymer may be irradiated with approximately 100 kGy of absorbed radiation.

The step of facilitating the consumption of free radicals may comprise heating to encourage the antioxidant when present in the first layer to diffuse into the second layer to consume the free radicals therein. This step can be considered an annealing step wherein the component is heated to below its melting point.

The steps of forming the first and/or second layers may comprise moulding. The moulding may comprise compression moulding and may be in the form of either cold compression moulding or hot compression moulding. The first layer may be moulded from a first powder comprising the first polymer and, optionally, the antioxidant. The second layer may be moulded from a second powder comprising the second polymer. The first and/or second powders may comprise a mix of particle sizes (e.g. from fine particles to flakes).

Alternatively, the steps of forming the first and/or second layers may comprise machining The first layer may be machined from a first bar stock comprising the first polymer and the antioxidant. The second layer may be machined from a second bar stock comprising the second polymer. The first and/or second bar stock may be formed by compression moulding a block (e.g. having dimensions of 3 m by 2 m by 10 cm) of the relevant materials. For example, the first bar stock may be formed by compression moulding a first block from a first powder comprising the first polymer and, optionally, the antioxidant and/or the second bar stock may be formed by compression moulding a second block from a second powder comprising the second polymer. Alternatively, the first and/or second bar stock may be formed by ram extrusion.

In a certain embodiment, the step of forming the first layer may comprise compression moulding the first layer by placing the first powder into a mould and hot or cold compression stamping (e.g. with 10 tonnes of pressure) the first powder into the desired shape of the first layer. When present, the antioxidant may be mixed or blended into the first polymer powder. The desired shape may include multiple protrusions in the intended wear zone to diffuse the interface between the first and second layers.

In a particular embodiment, the step of forming the second layer may comprise compression moulding by placing the second polymer powder over the whole or part of the formed first layer and applying a second mould to hot or cold compression stamp the desired shape of the second layer. In certain embodiments, this step may therefore comprise filling the area surrounding the protrusions created in the first layer with the second powder before applying the second mould to compression stamp the desired shape of the second layer.

In a specific embodiment, the first polymer powder may be compression moulded by applying a first piston through a syringe-like shroud. The first piston may then be removed from the shroud and the second polymer powder passed down the shroud before a second piston is applied through the shroud to compression mould the second layer onto the first layer. It has been found that this technique is particularly advantageous when the second layer forms only a part of an articular surface layer since the shroud helps to ensure that the second powder is not accidentally deposited on the first layer in the region outside that which is intended.

Alternatively, the step of forming the second layer may comprise compression moulding by placing the second powder into a second mould and hot or cold compression stamping the second powder into the desired shape of the second layer. This technique is expected to be particularly advantageous when the second layer forms the whole or a part of an articular surface layer which is not flat since it is difficult to evenly deposit the second powder onto a non-flat surface so as to obtain a second layer having an even (or pre-determined) thickness. Thus, in the case where the second layer forms a whole or a part of an articular surface layer of an acetabular cup prosthesis, it may be desirable to form the second layer separately from the first layer so as to ensure that the second powder does not accumulate in the pole of the cup thereby producing a thicker than intended layer of cross-linked polymer at the pole of the cup and a thinner than intended layer of cross-linked polymer at the periphery of the cup.

In a variant of the above method, the second powder may include a pre-determined amount of antioxidant, the concentration of which is determined to be low enough so as not to prevent cross-linking of the second layer but high enough so as to neutralise the oxidising effect of free radicals produced during the cross-linking process. In a further variant of the above, the second powder may include a relatively high concentration of blended antioxidant (e.g. 2% vitamin E), wherein the second powder is irradiated to cause extensive cross-linking of the second powder particles prior to formation of the second powder into the second layer.

In yet another variant of the second aspect of the present invention, the method may comprise cross-linking at least one further portion of the articular surface layer and/or at least one further surface of the component. This may be achieved using any of the methods described herein. In particular embodiments, the method could be employed to cross-link part of the articular surface and the whole (or part) of a back surface of a modular polymer acetabular bearing insert/liner to prevent or minimise wear of the back surface of the polymer against a metal acetabular cup shell. Other modular bearing inserts would also benefit by having their back surfaces highly cross-linked (for example, the back surface of a modular polymer bearing for a knee tibial component). In other embodiments, two (or more) surfaces may serve as articular bearing surfaces (e.g. in dual mobility hip bearings) and so these would also benefit from cross-linking in more than one area.

The method according to the second aspect of the invention may be configured for forming an articular surface for an acetabular cup prosthesis. In which case, the articular surface may be configured as a liner for an acetabular cup configured for use in either total hip replacement or hip resurfacing. In specific embodiments, the articular surface may be configured for use in an acetabular cup comprising any of the features described below in relation to the fifth to fifteenth aspects of the present invention.

An alternative method to that described above is specified below as a third aspect of the present invention. This method of forming an articular surface for a prosthesis comprises:
 forming a polymer component comprising an antioxidant;
 selectively removing the antioxidant, wholly or in part, from a portion of an articular surface layer;
 irradiating the component to cross-link the molecules in said portion; and
 facilitating the consumption of free radicals in said portion to thereby minimise the risk of oxidation of said portion.

The step of removing the antioxidant from a portion of an articular surface layer may comprise leaching out the antioxidant using a surfactant.

In embodiments of the third aspect of the invention, the method may further comprise selectively removing the antioxidant, wholly or in part, from at least one further portion of the articular surface layer and/or from at least one further surface of the component. The component may then be irradiated to cross-link the molecules in more than one portion and/or more than surface. In particular embodiments, the method could be employed to cross-link part of the articular surface and the whole (or part) of a back surface of a modular polymer acetabular bearing insert/liner to prevent or minimise wear of the back surface of the polymer against a metal acetabular cup shell. Other modular bearing inserts would also benefit by having their back surfaces highly cross-linked (for example, the back surface of a modular polymer bearing for a knee tibial component). In other embodiments, two (or more) surfaces may serve as articular bearing surfaces (e.g. in dual mobility hip bearings) and so these would also benefit from cross-linking in more than one area.

In a fourth aspect of the present invention, a method of forming an articular surface for a prosthesis comprises:
 forming a polymer component comprising an antioxidant;
 selectively inactivating the antioxidant, wholly or in part, from the whole or a portion of an articular surface layer;
 irradiating the component to cross-link the molecules in said articular surface layer; and
 facilitating the consumption of free radicals in said articular surface layer to thereby minimise the risk of oxidation of said articular surface layer.

The step of inactivating the antioxidant may comprise exposing the antioxidant to sunlight.

In embodiments of the fourth aspect of the present invention, the method may comprise cross-linking at least one further portion of the articular surface layer and/or at least one further surface of the component. This may be achieved using any of the methods described herein. In particular embodiments, the method could be employed to cross-link the whole (or a part) of the articular surface and the whole (or a part) of a back surface of a modular polymer acetabular bearing insert/liner to prevent or minimise wear of the back surface of the polymer against a metal acetabular cup shell. Other modular bearing inserts would also benefit by having their back surfaces highly cross-linked (for example, the back surface of a modular polymer bearing for a knee tibial component). In other embodiments, two (or more) surfaces may serve as articular bearing surfaces (e.g. in dual mobility hip bearings) and so these would also benefit from cross-linking in more than one area.

The following features are optional features of both the third and fourth aspects of the invention as defined above.

The antioxidant may comprise the following but is not limited thereto: vitamin E; alpha-tocopherol, delta-tocopherol; propyl, octyl, or dedocyl gallates; lactic, citric, ascorbic, tartaric acids; organic acids and their salts; orthophosphates; tocopherol acetate and Irganox 1010.

The step of forming the polymer component may comprise moulding (e.g. hot or cold compression moulding) and/or machining The step of facilitating the consumption of free radicals may be performed by ensuring that the concentration of antioxidant in the portion/articular surface layer is low enough to allow polymer cross-linking with radiation but high enough to consume the free radicals generated as a result of the radiation. Alternatively, the step of facilitating the consumption of free radicals may be performed by heating the component to encourage the antioxidant to diffuse from the remainder of the polymer component into the portion/articular surface layer to consume free radicals therein and thereby minimise the risk of oxidation.

The method according to the third or fourth aspects of the invention may be configured for forming an articular surface for an acetabular cup prosthesis. In which case, the articular surface may be configured as a liner for an acetabular cup configured for use in either total hip replacement or hip resurfacing. In specific embodiments, the articular surface may be configured for use in an acetabular cup comprising any of the features described below in relation to the fifth to fifteenth aspects of the present invention.

The present invention also relates to products and components produced by any of the methods described above in relation to the first to fourth aspects of the invention.

According to a fifth aspect of the present invention there is provided a prosthesis having a polymer articular bearing surface wherein at least one pre-determined portion of said bearing surface is provided with cross-linked polymer bonds.

In embodiments of this aspect of the invention, the predetermined portion will be arranged to correspond to the region that is believed to encounter the greatest abrasion from a mating articular surface (i.e. the pre-determined portion will be chosen to correspond to the zone likely to be subjected to the greatest amount of wear). It will be understood that a skilled person will readily be able to determine the likely wear zone from the geometry of the bearing surface and the mating articular surface, in view of the anticipated skeletal forces exhibited by the patient.

It is noted that, in the case of traditional acetabular cups having untreated (i.e. conventional) polyethylene inner liners, the volume of wear debris is found to be proportional to the size of the femoral head employed. Thus, in the case of total hip replacement, where, for example, 22 mm diameter heads are commonly used, the volume of wear debris from the polyethylene liner may be of an acceptable level. However, in the case of hip resurfacing it is common to use 45 to 55 mm diameter heads and, as a result, the volume of wear debris is relatively massive leading to unacceptable levels of wear, resulting in damage to the remaining bone stock. There is therefore a need for a high strength polymer which exhibits very low wear even when provided in thin layers against large femoral heads.

As described above, it is possible to prevent a polymer (e.g. polyethylene) from exhibiting any measurable wear by cross-linking its polymer bonds. This may be achieved by irradiating moulded or ram-extruded polymer. Whilst this does result in hard-wearing cross-linked polymer bonds, the process leaves free radicals which combine with oxygen such that the oxidised polymer is mechanically weak and therefore prone to breaking. It is possible to eradicate the free radicals (to prevent oxidation) by re-melting the material after radiation. This is known to give some reduction in the mechanical properties of the material (i.e. to make it weaker than before) but without weakening it as much as the oxidation process would. This process results in so-called first generation cross-linked polymer.

Second generation cross-linked polymer can be obtained by diffusing vitamin E into the substance of the polymer. The vitamin E is diffused after irradiation cross-linking such that the free radicals produced as a result of the cross-linking are consumed by the vitamin E. More specifically, the cross-linked polyethylene is immersed in a warm bath of liquid vitamin E and over several hours the vitamin E diffuses into the material. It is noted that second generation cross-linking cannot be performed by having substantial concentrations of vitamin E in the polyethylene powder before moulding or ram extrusion, as vitamin E and other anti-oxidants are known to prevent cross-linking.

Third generation cross-linking relates to cross-linking only the surface of a material. It has been found that increasing the concentration of vitamin E in the substance (prior to irradiation), decreases the amount of cross-linking and so vitamin E can effectively be used to prevent cross-linking in the bulk of the polymer—allowing only the surface layer to be cross-linked. It is then desirable to allow the vitamin E to diffuse into the surface layer so as to consume the free radicals resulting from the cross-linking process to prevent oxidation. In this case, the vitamin E from the bulk material is persuaded to diffuse into the surface cross-linked layer by annealing the material below its melting temperature for several hours.

The present aspect of the invention relates to partial surface cross-linking, which could be considered forth generation cross-linking. In essence only a selected part (or parts) of the surface is cross-linked to ensure that the intended wear zone is highly resistant to wearing while preserving the mechanical strength of the remainder of the polymer material. The fact that the cross-linking is limited to only a portion of the surface of the material is particularly advantageous where only thin layers of polymer are used since, in this case, the mechanical strength of the entire polymer construct is determined largely by the mechanical strength of the bulk material and the surface of the material surrounding the cross-linked area, which retains the strength of a conventional polymer.

It is believed that first, second and third generation cross-linked polymers lack the strength required for use in thin layer hip resurfacing components. However, it is believed that fourth generation (i.e. partial surface) cross-linking will provide sufficient strength (akin to that of conventional, non-cross-linked polymer) plus sufficient wear resistance in the area of articulation, even when used in thin layers as required in hip resurfacing, particularly when large femoral heads are employed.

It is also noted that metal-on-metal, ceramic-on-ceramic, and metal-on-cross-linked polymer bearings are all intolerant of so-called edge loading. Edge loading occurs when component mal-alignment (commonly cup misplacement due to surgeon error) results in load being transmitted from a prosthetic femoral head onto the edge of a prosthetic acetabular component. With metal-on-metal bearings this results in severe wear of the component parts. With ceramic-on-ceramic bearings this results in fracture of the prosthetic acetabular cup edge, due to ceramic being a brittle material. With a metal head on a fully cross-linked polyethylene acetabular cup liner, fracture of the cup liner can occur due to the relatively poor strength of the cross-linked material. It is noted that conventional polymer (e.g. polyethylene) bearings perform better in relation to edge loading than cross-linked polymer bearings since conventional polymer is stronger and tends not to fracture under conditions of edge loading, making the implant more forgiving of minor mal-position by the surgeon. Since the prosthesis of the present aspect of the invention is configured with only a small portion which is cross-linked and importantly leaving the edge of the component as conventional non-cross-linked polymer, it is believed that the mechanical properties of the prosthesis will be much more like those of conventional polymers and so it is expected that edge loading will not be a significant problem.

In certain embodiments, the polymer may be made thicker in the region of the pre-determined portion. This will help to ensure that the mechanical properties of the hulk of the material are unaffected by the surface cross-linking of the pre-determined portion.

The Applicant notes that there is a difference in the degree of crystallinity in the cross-linked polymer (e.g. polyethylene) portion than in the non-cross-linked polymer. Consequently, there is a concern that an abrupt interface between the two types of polymer will result in a high risk of de-lamination at the interface. The Applicant therefore proposes that multiple protrusions may be provided at the interface between the cross-linked polymer portion and the remainder of the polymer so as to obviate or minimise the risk of de-lamination at this interface. The protrusions may be in the form of ridges or fingers, for example in the shape of spikes, or they may be provided by introducing roughness at the interface between the two types of polymer. It will be understood that the inter-digitation of the material resulting from the provision of the protrusions will help to break up the sharp transition between the two types of polymer so as to provide a smoother transition between the two mechanically different varieties of the polymer (e.g. polyethylene).

The prosthesis may be configured as an acetabular cup. The acetabular cup may comprise a metal outer shell and a polymer inner liner, the inner surface of which constitutes the articular bearing surface having said pre-determined portion provided with cross-linked polymer bonds.

It will be understood that the various features described above in relation to the first to fourth aspects of the present invention may be combined with any of the features described above in relation to the fifth aspect of the invention, and vice versa.

The prosthesis may be configured as a femoral component or a tibial component for use in total knee replacement techniques. In particular, the articular bearing surface may be constituted by the condylar bearing surfaces provided on the tibial component. Additionally or alternatively, the articular bearing surface may be constituted by one or both mating surfaces of a cam and peg follower, one of which is provided on the femoral component and the other of which is provided on the tibial component.

According to a sixth aspect of the present invention there is provided an acetabular cup prosthesis comprising a metal outer shell and a polymer inner liner, wherein a mechanical means is provided to attach the inner liner to the outer shell to form a composite one-piece cup.

The sixth aspect of the present invention helps to overcome some of the disadvantages of metal cups described above (such as extreme patient allergies to metal, and wear of metal leading to excess metal ions in a patient's blood with possible long-term effects) by employing a polymer layer between the metal shell and the femoral component. An advantage of mechanically attaching the polymer layer to the metal shell is that the cup can be handled and inserted as a one-piece device which is stronger and more robust than its individual component parts. The likelihood of deformation of the cup on insertion is therefore reduced.

It will be understood that the metal shell of the present aspect of the invention is constituted by a solid piece of metal initially formed as a discrete component.

In an embodiment, the metal outer shell may be relatively thin and the polymer inner liner may be relatively thick. This helps to reduce the risk of metal debris whilst at the same time helping to ensure that the stresses generated in the polymer (from the forces exerted by the femoral head) are more easily absorbed in the thicker polymer layer.

The metal shell may have a thickness of approximately 0.5 mm to 6 mm. In certain embodiments the metal shell may have a minimum thickness of approximately 1 mm The thickness of the metal shell may vary, for example, from its edges to its pole.

The polymer liner may have a thickness of approximately 0.5 mm to 10 mm. In certain embodiments the polymer liner may have a minimum thickness of approximately 4 mm in a pre-determined wear zone and 1 mm in other regions. Thus, the thickness of the polymer liner may vary, for example, from its edges to its pole.

The mechanical means may comprise at least one bore, aperture, slot, recess or undercut in the metal shell into which the polymer liner extends so as to mate the inner and outer shells together.

In one embodiment, the mechanical means is constituted by, or comprises, a plurality of undercut spheres provided in the inner surface of the metal shell. In this case, the polymer liner may be compression moulded onto the metal shell so as to form a plurality of polymer nodules which are retained by the metal undercuts. This embodiment is particularly effective at securing the inner and outer shells together. The plurality of undercut spheres (and respective polymer nodules) may be provided over a substantial portion of the metal shell and may be provided close to the edge of the metal shell, even when the metal is relatively thin in that area.

Furthermore, the size of each of the undercut spheres may vary depending on the thickness of the metal in a particular location.

In some embodiments, the mechanical means may comprise stitching of the inner liner to the outer shell. The stitching may be provided along the whole or part of the cup edge. In particular embodiments, the outer shell may be provided with a rim around the whole or part of the cup edge. The rim may be perforated with a plurality of holes through which the polymer inner liner may extend to stitch the liner and shell together. The rim may be inset from the external surface of the outer shell to allow for a portion of the polymer inner liner to extend along or envelope the exterior surface of the rim, within the cup profile. In embodiments where the polymer liner is moulded (e.g. direct compression moulded (DCM)) into the outer shell, threads of the polymer will be forced through the holes in the rim and then moulded into the polymer provided around the rim to thereby stitch the edge of the liner to the shell. An advantage of using this technique is that it is easier to manufacture than the undercuts described above. The stitching may also be advantageous in connection with other aspects of the invention described below since it can help to retain the liner within the shell even when forces are applied which might otherwise serve to detach the liner from the shell.

In addition to the above, the mechanical means may comprise a (relatively large) threaded hole provided at the interior pole of the metal shell. The hole may be a blind hole and can be used in the handling of the metal shell during manufacture. In embodiments where the polymer liner is moulded (e.g. direct compression moulded (DCM)) into the outer shell, the threaded hole may provide macro-fixation. In addition, if the cup ever has to be removed from the patient, the polymer in the hole can be drilled out and the shell grasped by inserting a threaded rod into the threaded hole.

Alternatively, or additionally, the mechanical means may comprise a rough interior surface provided on the whole or a portion of the outer shell for micro-attachment of the polymer liner.

It is noted that although glue is unlikely to prevent de-lamination of the inner liner and outer shell on its own it could advantageously be used in combination with any of the above mechanical means.

The polymer liner may comprise one or more of polyimide, polyurethane, hylamer, carbon-fibre reinforced "PEEK" (Polyetheretherketone) or Ultra-High Molecular Weight Polyethylene (UHM WPE).

The metal shell may comprise one or more of titanium, titanium alloy or cobalt chrome.

It will be understood that, when the inner liner and outer shell are both relatively thin, it is advisable not to rely on a press-fit fixation within the body because of the risk of deformation. It is therefore important to consider an alternative form of fixation and a suitable means for handling and inserting the cup during surgery. These aspects of the invention will therefore be discussed in more detail below.

It will be understood that the various features described above in relation to the fifth aspect of the present invention may be combined with any of the features described above in relation to the sixth aspect of the invention, and vice versa.

According to a seventh aspect of the present invention there is provided an acetabular cup prosthesis comprising an outer surface and an inner surface, wherein the centre of the inner surface is displaced with respect to the outer surface so as to allow for an increased cup thickness in a pre-determined wear zone and wherein a cut-out is provided at an inferior edge of the cup to compensate for the displacement of the inner surface.

With current hip resurfacing techniques it is generally felt necessary to have a cup with an inner diameter to outer diameter difference of 6 mm so as to accommodate a reasonably sized femoral head in a robust acetabular cup prosthesis. However, it has been found that pseudotumours are more common in patients (particularly women) of small size. The Applicants therefore propose the present invention to allow for an increased femoral head size (i.e. through provision of a displaced inner surface) whilst maintaining the outer cup diameter. This will ensure the joint is more stable and has a larger surface area of contact thereby spreading the loads applied more effectively to reduce wear, while ensuring that no additional bone is resected from the acetabular cavity.

It will be understood that by displacing the inner surface with respect to the outer surface, a smaller inner diameter to outer diameter difference can be obtained. The provision of the inferior cut-out also helps to maximize the size of the inner diameter since no thickness of cup is required at the inferior edge.

The cup may be constituted by a single component (i.e. a mono-block), or by two or more components (e.g. having an outer shell and an inner liner—the outer surface being provided by the outer shell and the inner surface being provided by the inner liner).

The component (or components) may be formed from metal, ceramic, polymer, or a composite thereof.

Thus, the cup may comprise a single metal, ceramic, polymer or composite component.

Alternatively, the cup may comprise a metal, ceramic, polymer or composite shell and at least one metal, ceramic, polymer or composite liner. Any combination of shell material and liner material is possible. Thus, the shell and liner may comprise the same or different materials.

The outer surface (e.g. of the single component or the shell) may comprise a porous coating. The porous coating may be constituted by a (vacuum or non-vacuum) plasma sprayed metal (e.g. titanium) coating. Prior to application of the porous coating, the outer surface may be sculptured to create a series of protrusions (e.g. spikes) and/or indentations (e.g. pits). This may be achieved using known laser or e-beam sculpturing techniques, by casting (e.g. of a spiky surface), by forging the surface, or by machining the surface. In other embodiments, the porous coating may be formed by sintering or it may be formed separately and then attached to the outer surface of the cup (e.g. factory fitted by gluing or welding). In further embodiments, the porous coating may be integrally formed with the outer surface of the cup (e.g. by using a lost-wax technique to cast a shell having an integral lattice on its outer surface).

The centre of the inner surface (i.e. the centre of articulation) may be displaced outwardly of the outer surface and/or inferiorly thereof.

The inner surface may be displaced outwardly by 3.5 mm to increase the thickness in the pre-determined (i.e. intended) wear zone.

In other embodiments, the inner surface may be displaced outwardly by 7 mm and inferiorly by 2 mm. In a cup having a 56 mm outer diameter, this displacement will provide a 54 mm inner diameter, permitting use of a 54 mm diameter femoral head instead of a standard 50 mm diameter head (as would normally be used in a 56 mm outer diameter cup, since traditionally the inner diameter of such a cup would only accommodate a 50 mm diameter head).

It will be understood that the pre-determined wear zone may be located approximately in the centre of the cup but will more usually be located around the polar region of the inner surface and/or the superior region of the cup.

The cup may include one or more strengthening ribs on its outer surface. The strengthening ribs may be disposed in the region adjacent the periphery of the cup. The strengthening ribs may extend in a longitudinal direction towards the pole of the outer surface. The strengthening ribs may terminate short of the pole, for example, when the thickness of the cup reaches a pre-defined value.

In embodiments where the outer surface includes a porous coating, the strengthening ribs may be provided to butt against a moulding tool, thus preventing crushing of the porous coating between the ribs.

It will be understood that various features described in relation to the fifth, sixth and eighth to fifteenth aspects of the present invention may be combined with any of the features described above in relation to the seventh aspect of the invention, and vice versa.

According to an eighth aspect of the present invention there is provided an acetabular cup prosthesis comprising a metal outer shell and a polymer inner liner, wherein the centre of the polymer inner liner is displaced with respect to the metal outer shell so as to allow for an increased cup thickness in a pre-determined wear zone and wherein a cut-out is provided at an inferior edge of the cup to compensate for the displacement of the inner liner.

In conventional hip replacement there is no constraint on the thickness of the acetabular component. The acetabular component is press-fitted into place and since the femoral head and part of the femoral neck are resected, a prosthetic femoral head is used with a diameter much less than the diameter of the natural femoral head. Typically, this will result in a difference of approximately 18 mm between the outer and inner diameters of such an acetabular component (e.g. the cup may have a thickness of approximately 9 mm around its periphery). However, the aim of hip resurfacing is to preserve as much bone as possible by only replacing the surface layer. It is therefore desirable to have a much smaller outer diameter to inner diameter difference and the present Applicant believes that a difference of approximately 6 mm may be optimal in certain circumstances for preserving bone whilst at the same time allowing for insertion of a robust resurfacing cup.

In order to provide an inner diameter to outer diameter difference of approximately 6 mm (e.g. to allow for a 56 mm outer diameter cup for use with a 50 mm outer diameter head), it is possible to design a cup having a 1 mm thick metal shell and a 2 mm thick polymer liner, thus resulting in a total cup thickness of 3 mm all over. However, the Applicant has found that having only 2 mm of polymer in the pre-determined wear zone (i.e. in the region that is believed to encounter the greatest pressure from the femoral head) is not ideal because the high internal stresses experienced by the polymer in this region causes it to delaminate and wear away. The Applicant therefore proposes to displace (i.e. offset) the centre of the polymer liner so that the thickness of the cup can be increased in this region, without requiring more bone to be removed.

The centre of the inner liner (i.e. the centre of articulation) may be displaced outwardly of the metal shell and/or inferiorly thereof.

If we consider the case of a hemispherical cup (i.e. without a cut-out) having a metal shell of uniform 1 mm thickness, it will be noted that when the centre of the inner liner is displaced so as to provide 4 mm or more of polymer at the superior aspect of the cup (in addition to the 1 mm metal shell), it will not be possible to provide any polymer at the opposite, inferior edge of the cup (in addition to the 1 mm metal shell), if we wish to retain an inner to outer diameter difference of 6 mm. Thus, the Applicant proposes to provide a cut-out at the inferior edge of the cup so as to negate this problem and allow for maximum cup thickness in the region of highest wear whilst ensuring that a minimum thickness of metal and polymer is provided over the entire surface of the cup. In addition, the cut-out helps the surgeon to orientate the cup for correct placement (e.g. to ensure the cup is not inserted upside down).

In light of the above, the inner liner may be displaced such that a 1 mm thickness metal shell is provided with polymer liner having a 4 mm thickness in the pre-determined (i.e. intended) wear zone and a 1 mm thickness at the inferior edge.

It will be understood that the predetermined wear zone may be located approximately in the centre of the cup but will more usually be located around the polar region of the inner liner and/or the superior region of the cup.

In certain embodiments, the metal shell may be thicker in the region adjacent the pre-determined wear zone than at its inferior edge. For example, the metal shell may include an inwardly extending bulge (e.g. in the form of a convex saucer) of 2 to 4 mm thickness in this region. Advantages of this construction are that the additional metal provides increased strength and stiffness at the polar region and also that it allows for the attachment and/or support of fixation means on the exterior surface of the cup, as will be described in more detail below. A further advantage of having a thicker shell at the pole of the cup is that the centre of rotation of the prosthetic articulation is displaced laterally and into a closer to normal position than is commonly observed with conventional hip resurfacing prosthetic cups.

It will be noted that, in embodiments where the thickness of the metal is increased in the region adjacent the pre-determined wear zone, the thickness of the polymer liner may or may not be reduced in the same region, since the desired outer to inner diameter difference can be maintained in both cases by taking into account the lateral displacement of the articular surface.

The metal shell may be thin (e.g. 1 mm thick) around the entire periphery of the cup.

The metal shell may include one or more strengthening ribs on its exterior surface. The strengthening ribs may be disposed in the region adjacent the periphery of the cup. The strengthening ribs may extend in a longitudinal direction towards the pole of the shell. The strengthening ribs may terminate short of the pole, for example, when the thickness of the metal and/or polymer liner reaches a pre-defined value.

In certain embodiments, the outer surface of the cup may include a porous coating and so the strengthening ribs may be provided to butt against a moulding tool, thus preventing crushing of the porous coating between the ribs.

The metal shell may include a beveled edge. The beveled edge may be inclined inwardly. This feature can help to maximise the thickness of the polymer liner around the edge of the cup whilst maintaining the desired inner diameter.

The polymer liner may include a rounded edge. The rounded edge may extend over the edge of the metal shell to ensure no sharp metal edges are exposed to the patient or surgeon and, in particular, that any sharp edges are prevented from scratching the femoral head in the event of unwanted subluxation or dislocation.

Alternatively, the polymer liner may extend beyond the edge of the metal shell with an outer diameter equal to that of the metal shell so as to provide a continuous extension thereto. The edge of the polymer liner may be sloped outwardly so as to maximise the articular surface area.

It will be understood that the various features described above in relation to the eighth aspect of the present invention may be combined with any of the features described in relation to the fifth to seventh aspects of the invention, and vice versa.

According to a ninth aspect of the present invention there is provided an acetabular cup prosthesis comprising a metal outer shell and a polymer inner liner, wherein an attachment means is provided which projects from or through the polymer liner for attachment of the cup to an introducer configured for insertion of the cup into a patient.

An advantage of this aspect of the present invention is that attachment means is readily available for handling and orientating the cup, without having to (correctly) attach any additional components first. In addition, the fact that the attachment means projects from or through the polymer liner means that they cannot project from the curved outer surface of the metal shell. Accordingly, they do not interfere with the placement of the cup in the prepared bone of the acetabulum. In other words, the acetabulum can be prepared as normal, simply taking into account the size and shape of the outer shell of the cup. No additional cut-outs are required in order to accommodate the attachment means. Furthermore, the polymer surrounding the attachment means can help to cushion the interface between the cup and the introducer when attached.

The attachment means may project from or through the edge of the polymer liner. The attachment means may project from or through the edge in a direction generally perpendicular to the plane of the edge. In certain embodiments, the attachment means may be sloped or curved inwardly towards the centre of the cup. For example, the attachment means may project from or through the edge at an angle of, say, 5, 10, or 20 degrees inwardly from the perpendicular direction. Alternatively, the attachment means may extend from or through the curved inner surface of the polymer liner.

The attachment means may be formed as an integral part of the polymer liner (e.g. by injection or compression moulding).

Alternatively, the attachment means may be formed as an integral part of the metal shell. In this case, the polymer liner may be moulded around the attachment means so that it protrudes therefrom.

In certain embodiments, the attachment means may be joined to the metal or polymer liner by melting or gluing or by mechanical means such as by small loops.

The attachment means may comprise one or more loops having a first end and a second end secured to the cup. The loops may be thickest at their first and second ends so as to provide more support at these joints. In one embodiment, two loops are provided, one on each side of the cup. The loops may be integrally moulded with the polymer liner. After insertion of the cup into a patient, the loops may be removed (e.g. by cutting the first and second ends from the polymer liner) so as to leave the polymer liner with a relatively flush, smooth surface.

The attachment means may comprise one or more projections having a serrated surface. Alternatively, the attachment means may comprise one or more projections having a device configured to lock onto a serrated surface. The device may include an opening having a ridge arranged to locate between two adjacent serrations. The device may be configured to easily accept the serrated surface (i.e. to allow the serrated surface to be inserted into it) but to prevent the serrated surface from being removed from its grasp.

In other words, the device may be configured to allow the serrated surface to be passed through it in one direction but to prevent the serrated surface from passing through it in the opposite direction. Thus, the attachment means in these embodiments may take the form of cable ties, with either the serrated surface or the device for locking onto the serrated surface being provided as the attachment means on the cup and the other of the serrated surface or the device for locking onto the serrated surface being provided on the introducer.

In a further embodiment the attachment means may comprise one or more projections. The projections may be in the form of fingers or straps. The projections may have a smooth exterior surface. In this case, the introducer may comprise gripping means for gripping onto the projections. The gripping means may comprise teeth arranged to bite into the projections.

The attachment means may comprise one or more rods. The rods may be provided with an enlarged portion at their free ends configured for gripping by an introducer. The enlarged portion may be spherical. In a certain embodiment the enlarged portion may be generally conical and orientated with its tip at the free end of the rod. In one embodiment the enlarged portion may comprise two or more conical portions stacked with their tips all towards the free end of the rod. The rods may include a neck configured such that rotation of the rod with respect to the inner and outer shells will cause the rod to shear at the neck. In one embodiment the rods may be extensions of the polymer liner and, in this case, the location of the neck may be close to the base of each rod. In another embodiment the rods may be extensions of the metal shell and, in this case, the location of the neck may be below the height of the polymer liner through which it extends. This embodiment is particularly advantageous, because the polymer liner can serve to protect the surrounding tissue from damage by the portions of the metal rods remaining after the cup has been inserted.

It will be understood that the various features described above in relation to the fifth to eighth aspects of the present invention may be combined with any of the features described above in relation to the ninth aspect of the invention, and vice versa.

According to a tenth aspect of the present invention there is provided an impactor cap for an acetabular cup prosthesis comprising a bulbous outer surface configured to fill the interior of said acetabular cup; and a flange configured to extend around the outer edge of the cup and to rest thereon when said bulbous surface fills the cup interior.

This aspect of the invention therefore provides a device which snugly and completely mates with an acetabular cup and therefore it helps to impart strength to the cup so that it is less likely to deform when it is being forced into the prepared bone of a patient. As it is desirable to have a tight, and therefore secure, fit of the cup in the bone, it is common for a surgeon to hit the cup into place with a hammer or similar instrument. However, in the case of hip resurfacing, it common to use thin-walled cups and it will therefore be understood that directly hitting such a cup to insert it will have a high chance of damaging and/or deforming the cup. The present aspect of the invention therefore helps to minimise this risk.

The impactor cap may be configured such that it is only possible to fully insert it into a cup if it is presented in one particular orientation with respect to the cup. This can help to ensure that the surgeon inserts the cup into the patient in the correct orientation.

In one embodiment the acetabular cup prosthesis is provided with an inferior cut-out and the flange of the impactor cap will therefore be shaped to include said cut-out.

A location means may be provided for attachment of an introducer to the impactor cap. The location means may be configured such that it is only possible to correctly attach the introducer to the impactor cap if it is presented in one particular orientation with respect to the impactor cap (and therefore the cup).

In an embodiment the location means may be constituted by a rotationally constrained recess. In another embodiment the location means may be constituted by a rotationally constrained projection.

According to an eleventh aspect of the present invention there is provided an introducer for an acetabular cup prosthesis comprising a mating means for mating with the cup; a gripping means for securing the cup to the introducer; and a handle for manipulating the position of the cup for insertion; wherein the mating means is configured to mate with the cup in one orientation only.

As above, the present aspect of the invention helps to ensure that the surgeon inserts the cup into the patient in the correct orientation since it is not uncommon for a cup to be incorrectly inserted.

The mating means may be constituted by a rotationally constrained recess or projection configured for location with a cooperatively constrained portion of a cup or an impactor cap, such as those defined above.

In one embodiment the mating means may be constituted by an impactor cap in accordance with an embodiment of the tenth aspect of the invention. In other words, the impactor cap may form an integral part of the introducer.

The gripping means may be configured for co-operating with the attachment means of a cup, such as those defined above in relation to the ninth aspect of the invention. Accordingly, the gripping means may comprise one or more hooks, clamps, projections having a serrated surface or devices for locking onto a serrated surface. The gripping means may further comprise a tensioning means for tightening the grip on the attachment means so as to more securely fasten the cup to the introducer.

The handle may include a kink to navigate around a portion of the patient's body when inserting the cup into position. It will be understood that when the cup, the impactor cap and the introducer are all fixed together, it is not possible for the surgeon to insert the cup upside down as the kink in the introducer handle physically prevents this. The handle may be provided with an end suitable for hitting with a hammer or similar instrument to force the cup into position. The end may be arranged to be perpendicular to the axis of the pole of the cup so as to transmit a force applied to it through the axis of the cup. Where the inner diameter of the cup is displaced with respect to the outer diameter of the cup, the axis of the cup will be taken to be that in relation to the outer surface of the cup, in this instance.

According to a twelfth aspect of the present invention there is provided a prosthesis having an external surface provided with a rough exterior to aid initial fixation; a porous structure for bone in-growth; and a plurality of undercuts to allow bone to lock onto the surface.

In the case of thin-walled acetabular cup prosthesis, such as those required for hip resurfacing, it has been found that traditional, aggressive (e.g. 2 mm squeeze) press-fit techniques are unsuitable because the wall of the cup is not strong enough to withstand the compressive forces applied in this instance. Accordingly, it is necessary to employ another mechanism to fix the cup in position.

The present aspect of the invention provides a suitable fixation means for a prosthesis by including a rough (e.g. sharp-edged) exterior surface which can provide good primary fixation in the bony bed, including a porous structure which is bio-acceptable so as to allow bone to grow onto and into the surface of the prosthesis and undercuts so that ingrown bone can extend into these regions to develop a mechanical lock onto the implant.

Providing a porous external surface is one technique that has previously been employed to aid fixation of prosthesis. Such a porous surface has been achieved by gluing wax/polymer beads onto a surface of a wax/polymer facsimile of a prosthesis and by using the so-called lost-wax technique of creating a solid ceramic encasement around the resulting wax/polymer facsimile, melting and removing the wax/polymer from the ceramic, pouring molten metal into the resulting cavity, allowing the molten metal to solidify and then breaking the ceramic encasement (and dissolving the ceramic in the metal undercuts by leaching the material in a strong alkali) to release a solid metal implant having a beaded external surface. Whilst it has been found that such a beaded surface does permit bone in-growth (over time) to penetrate between adjacent beads to latch onto the prosthesis, the fact that the beads are generally spherical and therefore only have a single, smooth point of contact with the surrounding bone on insertion means that there is little frictional resistance to hold the implant in place. The present aspect of the invention addresses this problem by including a rough (e.g. sharp) surface to increase the frictional resistance between the prosthesis and the surrounding bone so as to aid initial fixation of the implant.

An alternative known method of creating a porous surface includes gluing a layer of sponge-like structure (e.g. a 2 mm thick piece of reticulated polyurethane foam) onto a wax/polymer facsimile of a prosthesis and using the lost-wax technique described above to create a metal casting having a sponge-like surface layer for bone in-growth. However, with this technique it is necessary for the sponge-like structure to have a thickness of at least 2 mm so as to provide structural integrity. As a consequence, the thickness of the solid metal of the prosthesis is required to be made thinner to accommodate such a thick porous layer, thereby resulting in an overall weaker metal structure. In addition, it has been observed that the interconnecting 'fibres' of the sponge-like structure can be relatively thin leading to areas of imperfect filling with the molten metal and resulting in defects in the porous coating. In order to obviate this problem the molten metal has to be made less viscous than normal by increasing the melt temperature. However, the downside of this temperature increase is that it increases the grain size of the resulting cast metal, which weakens the material and can lead to fatigue failure and fracture in use. It is therefore an aim of the present invention to ameliorate these problems.

The porous structure of the present aspect of the invention may be formed by e-beam or laser sintering of powdered metal (e.g. titanium, titanium alloy or cobalt chrome). These techniques essentially build the structure in layers and can be used to form features having microscopic dimensions.

Alternatively, the porous structure of the present aspect of the invention can be formed using lost-wax casting or centrifugal casting of metal. Such casting techniques are likely to be more cost-effective than the above sintering techniques for large-scale production.

The porous structure may be constituted by a lattice. It will be understood that the term lattice is used throughout to denote a series of interconnecting or contacting parts including gaps therebetween. The lattice may be formed as a repeating pattern of interconnected elements.

This embodiment has the advantage of providing a homogeneous surface having similar properties throughout. This therefore overcomes a disadvantage encountered in prior art prosthesis such as those described above, wherein, for example, discrete wax/polymer beads are required to be individually glued to a wax/polymer facsimile of a prosthesis in order to form a metal casting therefrom and the homogeneity of the beaded surface therefore depends on the skill of the person applying the beads. In addition, the interconnecting or touching structure of the lattice can impart mechanical resistance to bending thereby increasing the strength of the prosthesis. This is particularly advantageous when used on thin-walled components such as an acetabular hip resurfacing cup having a wall thickness of approximately 1 mm at least at the periphery of the cup.

In certain embodiments, the lattice may be 0.25 to 1 mm in thickness, for example, 0.5 mm The relatively thin nature of the lattice will help to ensure that valuable structural support thickness of the main body of the prosthesis will not need to be sacrificed to accommodate the porous structure.

The lattice may comprise a plurality of posts radially extending from the exterior surface of the prosthesis, the posts supporting a series of interconnected bridging elements. Two or more types of posts may be provided, each having a different transverse cross-section. In one embodiment, a first set of posts may have a circular cross-section and a second set of posts may have a multi-lobed cross-section (e.g. a triple-lobed cross-section). Each post in the first set of posts may be arranged to support mating ends of a plurality of bridging elements. In one embodiment, each post in the first set of posts may be arranged to support mating ends of six bridging elements. Each bridging element may extend radially from the first post to a lobe of one of the second sets of posts. Each of the second set of posts may be arranged to support mating ends of a plurality of bridging elements, one extending from each of its lobes. Accordingly, in an embodiment where each circular post supports six bridging elements and each lobed post supports three bridging elements, a tessellating pattern is created with gaps (i.e. cavities) forming between the bridging elements which are in the shape of 4-sided diamonds. The lattice may be configured such that the diamond holes may have a diameter of 0.1 to 1.0 mm, for example, 0.5 mm However, it will be understood that many different lattice configurations could be conceived in accordance with this aspect of the present invention.

It will be understood that the supported lattice structures described above not only allow bone in-growth through the gaps (e.g. diamond holes) between the bridging elements but also provide undercuts in the regions underneath the bridging elements, between the posts, into which bone can grow to mechanically lock the implant in place.

The lattice structure described above could be injection moulded in flexible plastic before the posts are glued to the exterior surface of a wax/polymer facsimile of the prosthesis. The lost-wax technique described above could then be employed to allow metal to flow through the posts and into the bridging elements to create the metal casting including the lattice in its exterior surface.

In specific embodiments, the posts may be 0.5 to 1.5 mm in diameter, for example, 1.0 mm These relatively wide elements will permit easy flow of material into the lattice during a casting process, so that complete filling of a mould can be achieved at normal casting temperatures (i.e. without requiring higher than normal melt temperatures resulting in a weakening of the material cast).

The bridging elements may also have a relatively thick cross-section (e.g. 0.5 to 1.5 mm wide and 0.2 to 0.5 mm thick) for the same reason as above. In a particular embodiment, the bridging elements may have a width of 0.7 mm and a thickness of 0.3 mm.

The rough exterior may be provided on the lattice by including cut-outs in the exterior surface of the bridging elements. For example, diamond or pyramid shaped cut-outs can be provided so that multiple sharp edges are presented to the bone for primary fixation of the implant. The cut-outs could be created by including the desired shapes in the injection mould tool for the lattice.

Alternatively, a rough exterior could be applied to the lattice by applying a plasma spray coating to the injection mold tool or sand blasting the injection mold tool to give the lattice and hence the final cast implant a rough outer surface.

In another embodiment, the lattice may comprise a plurality of touching truncated beads. The advantage of truncating the beads is that a larger surface area is provided for initial contact to a prepared bony cavity. Each bead may be truncated horizontally through its centre so as to present its largest surface area to the bone. The truncated surface of each bead may have a diameter of approximately 0.2 mm to 2 mm.

The truncated surface of each bead may be provided with a plurality of micro-spikes to provide the rough exterior to the prosthesis. These micro-spikes will enable better grip of the bone on insertion, thereby reducing the need for a press-fit fixation which is unsuitable for use with thin-walled components.

Each micro-spike may have a diameter of approximately 0.5 mm or less.

In certain embodiments, each bead may be provided with 3 to 50 micro-spikes (depending on the size of each bead and each micro-spike). In one embodiment, each bead is provided with 7 micro-spikes.

The external surface of the prosthesis may be formed of metal. The porous structure, undercuts and rough exterior may also be formed of metal and may be integrally formed with the external surface of the prosthesis.

The prosthesis may be configured as an acetabular cup. The acetabular cup may comprise a metal outer she !] and a polymer inner liner, the external surface of the prosthesis being constituted by the external surface of the metal outer shell.

In addition to the methods described above for casting a metal shell with an integral porous coating it is also possible to make a ceramic mould shell with an integral porous layer by Virtual Pattern Casting whereby a mould is built up directly in ceramic including the bulk implant and the integral porous surface layer. The mould can then be filled (preferably under pressure) using centrifugal casting but other casting methods can optionally be employed.

In embodiments of the present invention, a (vacuum or non-vacuum) plasma sprayed metal (e.g. titanium) coating may be employed to provide a porous structure for bone in-growth and/or undercuts (between the metal particles) to allow bone to lock onto the surface.

However, it has been discovered that such a coating can dislodge (although a vacuum plasma sprayed coating is thought to be less prone to this) and it is difficult to obtain a really rough surface with this technique. Accordingly, in certain embodiments, the applicant proposes to employ (e.g. laser or e-beam) sculpturing of the external surface of the prosthesis to create a plurality of spikes which can be made relatively sharp and can provide a rough surface which is good for initial fixation of the prosthesis, prior to applying a (vacuum or non-vacuum) plasma sprayed metal coating to provide undercuts and a good pore size for bone in-growth.

Laser and e-beam sculpturing of metal surfaces is known (for example, as described on the website of The Welding Institute (TWI) in relation to their so-called Surfi-Sculpt® technique). Essentially, the sculpturing is performed by using a laser/e-beam to melt a small droplet of metal on the surface. The laser/e-beam is then moved a small distance in a transverse direction (approximately parallel to the metal surface) so that the droplet of metal is pushed out of the melt pool and allowed to solidify into a protruding spike which may be approximately 0.5 mm in height.

It is believed that an additional advantage of the present embodiment is that by creating a spiky surface before plasma spraying, it is possible to improve the bonding of the sprayed metal particles. This is because it has been observed that, under normal circumstances, (i.e. when a plasma sprayed coating is employed without spikes) it is common for the metal particles to be sheared off the prosthesis when it is press-fitted into a patient. However, by having a sculptured (i.e. spiked) surface underlying the sprayed coating, it is hoped that the shear forces previously causing particle dislodgment will be converted into compressive forces making the particles much less likely to dislodge.

It will be understood that the various features described above in relation to the fifth to eleventh aspect of the present invention may be combined with any of the features described above in relation to the twelfth aspect of the invention, and vice versa.

The thickness of the metal shell defined in any of the described aspects of the invention may be taken to include both the thickness of the shell itself and the thickness of the external surface provided on that shell (including the porous structure, undercuts and rough exterior of the present aspect of the invention).

A further embodiment of the sixth aspect of the invention is contemplated wherein the exterior surface of the metal outer shell is constituted in accordance with the present aspect of the invention and the mechanical means attaching the metal outer shell to the polymer inner liner is in the form of a plurality of undercut spheres provided in the inner surface of the metal shell and extending into a solid portion of the porous structure. Thus, the undercut spheres for polymer attachment may be configured to extend into the posts or beads of a lattice porous structure as defined above. This configuration is particularly advantageous in minimising the thickness of the metal shell whilst maintaining its integrity and strength.

It will be noted that in embodiments of the present aspect of the invention, the porous structure, undercuts and rough exterior may not extend over the entire external surface area of the prosthesis. In particular, a rim of solid metal may be provided around the edge of the metal shell, where the metal may be thinnest. This rim of solid metal may vary in width around the edge of the shell. In particular, the rim may be widest (e.g. 3-4 mm) around the supero-lateral edge (often referred to as either the superior edge or the lateral edge) of the shell and narrowest (e.g. 1-2 mm) around the inferior edge of the shell. This additional rim width is advantageous for support since it is common to have no bone covering the supero-lateral edge of the cup (e.g. at 40 to 45 degrees of inclination).

Furthermore, the exterior surface of the prosthesis may be configured such that the porous structure is contained within the metal shell so that the rough exterior is substantially flush with any portions not including a rough exterior, such as the rim defined above and the strengthening ribs defined in relation to the seventh and eighth aspects of the invention.

In certain embodiments, strengthening ribs may be provided on the exterior surface of the cup to butt against a moulding tool, thus preventing crushing of the porous structure between the ribs.

The prosthesis of the present aspect of the invention may be configured as a hip resurfacing femoral component, or a femoral stem for use in total hip replacement.

In other embodiments, the prosthesis of the present aspect of the invention may be configured as a femoral component or a tibial component for use in knee replacement techniques.

In yet further embodiments, the prosthesis of the present aspect of the invention may be configured as any uncemented implant such as a shoulder, spinal, elbow, wrist, finger, ankle or toe implant.

According to a thirteenth aspect of the present invention there is provided a prosthesis having an external surface provided with an array of fixation spikes configured to penetrate into a prepared bone cavity.

The fixation spikes may be configured to penetrate the bone by a depth of 2 mm or so. Notably, it is desirable that no holes are cut in to the bone cavity to accommodate the spikes prior to their insertion. The spikes are therefore configured to penetrate into the bone simply on impaction of the prosthesis. Accordingly, the fixation spikes can function as a primary fixation means negating the need for an aggressive press-fit of the prosthesis which can cause deformation, particularly of thin-walled components.

The array may comprise 10 to 500 fixation spikes, for example, 100 or 200.

The array may be formed as an integral part of the external surface of the prosthesis.

Each fixation spike may have a height of approximately 2 mm. In some embodiments, the height of the fixation spikes may vary. For example, the fixation spikes at the edge of the array may be of a minimum height (e.g. 0.5 mm) with the height of the fixation spikes gradually increasing towards the centre of the array. At the centre the spikes may be 2 mm in height.

The spikes may be conical in shape, terminating in a sharp point.

The prosthesis may be configured as an acetabular cup. The acetabular cup may comprise a metal outer shell and a polymer inner liner, the external surface of the prosthesis being constituted by the external surface of the metal outer shell.

The array may be located on the most proximal region of the cup (as defined with reference to the body of the patient) when orientated ready for insertion. Thus, on impaction the spikes are the first portions of the cup to contact the bone and therefore they are able to be forced into the bone before the remainder of the cup contacts the bony cavity and prevents any further penetration.

Each fixation spike may point parallel to the axis of the pole of the cup, when viewed from the inferior side of the cup, and parallel to the axis of insertion of the cup into the bone.

It will be understood that the various features described above in relation to the fifth to twelfth aspects of the present invention may be combined with any of the features described above in relation to the thirteenth aspect of the invention, and vice versa.

A further embodiment of the eighth aspect of the invention is contemplated wherein the exterior surface of the metal outer shell is constituted in accordance with the present aspect of the invention and the fixation spikes are provided on the thicker region of the metal shell (adjacent the pre-determined wear zone).

According to a fourteenth aspect of the present invention there is provided a prosthesis having an external surface provided with at least one fixing means configured for the exterior attachment of a modular peg.

Thus, the present aspect of the invention provides a means for selectively attaching a peg to prosthesis from the exterior thereof. It is known to provide pegs on prosthesis such as acetabular cups by screwing the pegs into position by inserting them through an interior surface of the cup. It is, however, envisaged that embodiments of this aspect of the invention will be in the form of an acetabular cup prosthesis having a metal outer shell mechanically connected to a polymer inner liner such that attaching a peg to the prosthesis is not possible from the interior of the cup.

It will be understood that the provision of a peg extending from the prosthesis will limit the final position of the prosthesis and so it is important that the hole prepared in the bone to accommodate the peg is in the correct position. Commonly, the position of any holes required for pegs would be determined using a trial prosthesis such as a trial acetabular cup, which is also used to check that the cavity created for the cup is of the correct size. Generally, trial cups are configured for line-to-line fit within the bone cavity (or a very slight press-fit). They are also provided with a smooth exterior surface so that they can be removed from the cavity relatively easily (i.e. without much frictional resistance). Since the trial cup is not a tight press-fit in the acetabulum, it is possible to attach to the trail cup a navigation device or alignment device (such as that described the Applicant's co-pending US-2008-0269757-A 1). When the correct position of the trial cup has been achieved, the holes for the one or more pegs are drilled. These holes guide the pegs on the definitive implant to achieve a perfect position, without the need for an alignment or navigation device to be used on the definitive cup.

If the cavity is determined to be a good fit for the trial cup, the surgeon may decide that no modular pegs are required for additional fixation and so the prosthesis may be inserted without the modular pegs being attached. This is the ideal situation. However, if the trial cup is determined not to provide such a good fit, the surgeon may decide that additional fixation is required and, in which case, he/she can select to attach one or more modular pegs to the prosthesis and to drill the required holes through corresponding holes provided in the trail cup.

The fixing means may be constituted by a cavity having an internal screw-thread. In which case, the modular pegs would include a base having a complementary external screw thread. The cavity may have a closed end to prevent debris or tissue from passing through the external surface of the prosthesis and causing damage within. Where an inner polymer liner is provided, the closed end will also help to support the polymer layer which may be thin in this region. In addition, the closed end will prevent any polymer debris from migrating into the bone of the patient's acetabulum, which could lead to osteolysis.

A filling may be provided to substantially fill the cavity of the fixing means if the modular peg is not required. The filling may be in the form of a grub screw having an external screw thread to mate with that of the fixing means and a relatively small recess in its top surface for location of a tool (such as a screwdriver or Allen key) to selectively remove the filling.

Each modular peg may be conical in shape, terminating with a rounded tip.

The modular pegs may include one or more notches to aid grip when attaching them to the fixing means.

In a particular embodiment two fixing means and modular pegs are provided.

The prosthesis may be configured as an acetabular cup. The acetabular cup may comprise a metal outer shell and a polymer inner liner, the external surface of the prosthesis being constituted by the external surface of the metal outer shell.

The modular pegs (and hence, their fixing means) may be located on the most proximal region of the cup (as defined with reference to the body of the patient) when orientated ready for insertion.

The modular pegs may extend in a direction normal to the external surface of the cup. This is advantageous in that it allows for a maximum thickness of the cup (e.g. of the metal shell of the cup) for anchoring the modular pegs in the fixing means. However, it will be understood that when more than one peg extends in a direction normal to the curved surface of the cup, they will effectively diverge making insertion into the prepared bone impossible unless the outer sides of the pegs are either parallel or converging. Thus, conical pegs may be used for ease of insertion.

Where two conical modular pegs are provided, they may be configured such that each of their outer edges are parallel or converging. In this case, the conical shape means that the cup (and therefore the pegs) are insertable in a straight line even though the pegs have a diverging long axis (e.g. when viewed from the inferior edge).

It will be understood that the various features described above in relation to the fifth to thirteenth aspects of the present invention may be combined with any of the features described above in relation to the fourteenth aspect of the invention, and vice versa.

A further embodiment of the eighth aspect of the invention is contemplated wherein the exterior surface of the metal outer shell is constituted in accordance with the present aspect of the invention and the modular pegs are provided on the thicker region of the metal shell (adjacent the pre-determined wear zone).

According to a fifteenth aspect of the present invention there is provided a prosthesis having an external surface fitted with at least one permanent peg.

Thus, the present aspect of the invention provides a prosthesis having a peg permanently fixed to an outer surface thereof. This is possible with the present invention since it is envisaged that a trial cup will be used to determine the exact location of the peg(s) so that location of the peg(s) into holes created with the trail cup in the correct position will guide the prosthesis into the correct location with no further alignment required.

The at least one peg may be formed separately from the remainder of the prosthesis and then permanently fitted thereto (e.g. by gluing or welding). Alternatively, the at least one peg may be integrally formed with the prosthesis.

Each peg may be conical in shape, terminating with a rounded tip.

In a particular embodiment two pegs are provided.

The prosthesis may be configured as an acetabular cup. The acetabular cup may comprise a metal outer shell and a polymer inner liner, the external surface of the prosthesis being constituted by the external surface of the metal outer shell.

The at least one peg may be located on the most proximal region of the cup (as defined with reference to the body of the patient) when orientated ready for insertion.

The at least one peg may extend in a direction normal to the external surface of the cup. This is advantageous in that it allows for a maximum thickness of the cup (e.g. of the metal shell of the cup) for anchoring the peg in the fixing means. However, it will be understood that when more than one peg extends in a direction normal to the curved surface of the cup, they will effectively diverge making insertion into the prepared bone impossible unless the outer sides of the pegs are either parallel or converging. Thus, conical pegs may be used for ease of insertion.

Where two conical pegs are provided, they may be configured such that each of their outer edges are parallel or converging. In this case, the conical shape means that the cup (and therefore the pegs) are insertable in a straight line even though the pegs have a diverging long axis (e.g. when viewed from the inferior edge).

It will be understood that the various features described above in relation to the fifth to thirteenth aspects of the present invention may be combined with any of the features described above in relation to the fifteenth aspect of the invention, and vice versa.

A further embodiment of the eighth aspect of the invention is contemplated wherein the exterior surface of the metal outer shell is constituted in accordance with the present aspect of the invention and at least one peg is provided on the thicker region of the metal shell (adjacent the pre-determined wear zone).

BRIEF DESCRIPTION OF THE DRAWINGS

Embodiments of the present invention will now be described with reference to the accompanying drawings in which:

FIG. 14A shows a top perspective view of the impactor cap shown in FIGS. 6A-6D, 9,12 and 13;

FIG. 14B shows an underneath perspective view of the impactor cap of FIG. 14A; FIG. 14C shows an underneath perspective view from a first side of the impactor cap of FIG. 14A;

FIG. 14D shows an underneath perspective view from a second side of the impactor cap of FIG. 14A;

FIG. 25A shows the configuration of FIG. 24C in an elevation view from the inferior end of the cup;

FIG. 25B shows the configuration of FIG. 24C viewed from above the centre of the superior end of the cup;

FIG. 25C shows the configuration of FIG. 24C viewed from above the side of the superior end of the cup;

FIG. 25D shows the configuration of FIG. 24C in an elevation view from one side of the cup;

DETAILED DESCRIPTION OF CERTAIN EMBODIMENTS

Figure 1:
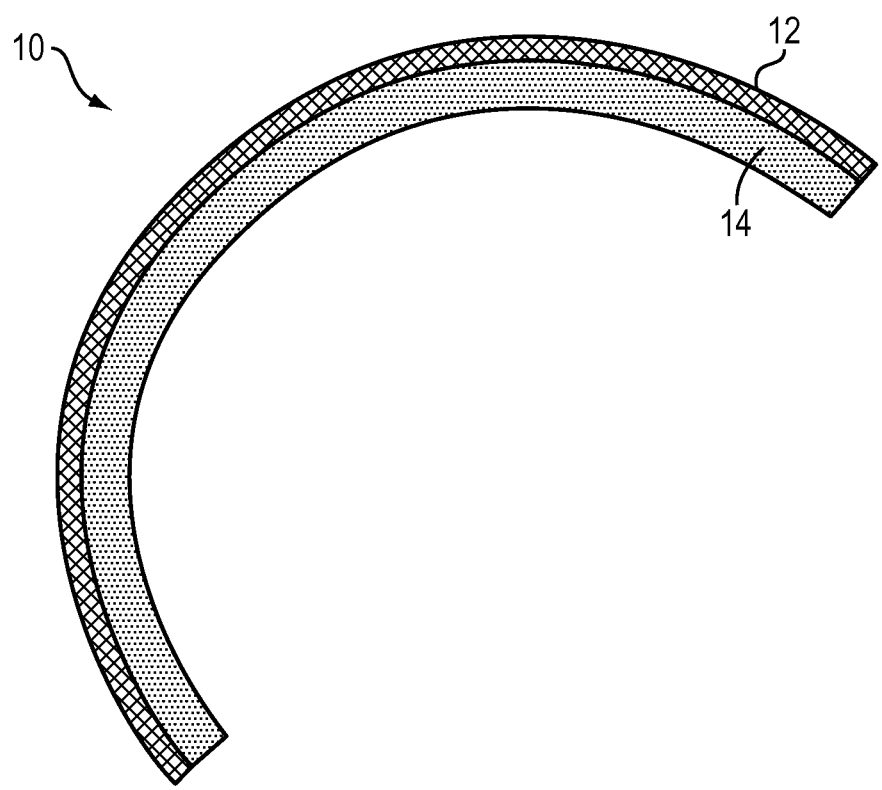
FIG. 1 illustrates schematically a cross-section through a proposed acetabular cup prosthesis having a relatively thin metal outer shell and a relatively thick polymer inner liner.

With reference to FIG. 1, there is illustrated a central cross-section of a proposed acetabular cup prosthesis 10 having a relatively thin (e.g. 1 mm) hemi-spherical metal outer shell 12 and a co-centred relatively thick (e.g. 2 mm) hemi-spherical polymer inner liner 14. In this case, the polymer inner liner or shell 14 is glued by an adhesive (not shown) to the inner surface of the metal outer shell 12. It will be noted that inner diameter to outer diameter difference of the cup 10 is 6 mm—the cup 10 having a thickness of 3 mm at each side.

While such a thin-walled acetabular cup prosthesis is desirable for hip resurfacing (where only a minimal amount of bone is removed to accommodate the implant), it has been proposed that insertion of the cup using a traditional 2 mm press-fit technique would lead to uncontrolled distortion and damage to the cup. Various aspects of the present invention therefore aim to address this problem.

Figure 2:
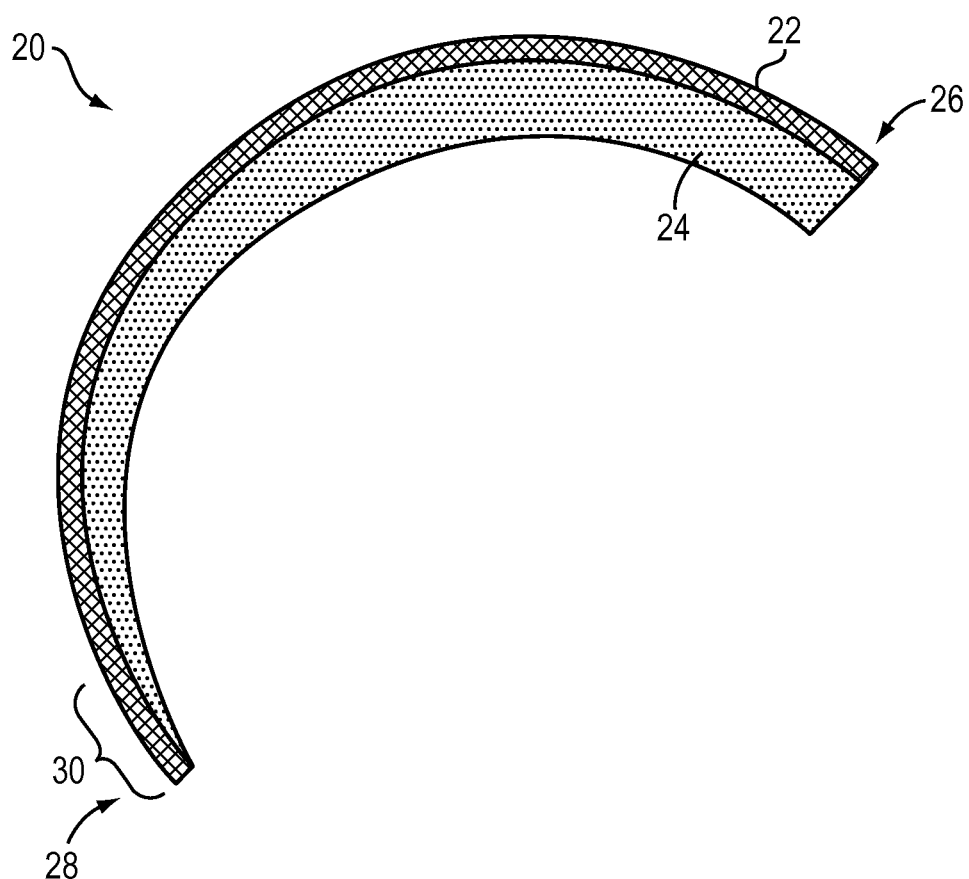
FIG. 2 shows a view similar to that of FIG. 1 but with the centre of the polymer inner liner displaced with respect to the metal outer shell to as to allow for an increased cup thickness in a pre-determined wear zone, in accordance with a first embodiment of the present invention.

FIG. 2 shows a central cross-section of an acetabular cup prosthesis 20, which is similar to that shown in FIG. 1 but with the centre of the polymer liner 24 displaced outwardly and downwardly (i.e. distally and inferiorly) with respect to the metal shell 22. This allows a greater thickness of the polymer liner 24 to be provided in the region of highest wear (i.e. in the intended wear zone) which generally extends towards the supero-lateral edge 26 of the cup 20 from slightly below the centre of the cup 20.

As one aim of the present invention is to preserve as much bone as possible, it is desirable not to increase the inner diameter to outer diameter difference of the acetabular cup 20 as a result of thickening the polymer liner 24 in the intended wear zone. Thus, as illustrated it can be seen that maintaining a 1 mm thick metal shell 22 and displacing the polymer liner 24 to provide 4 mm of thickness at the supero-lateral edge 26 results in the polymer liner 24 having zero thickness at the inferior edge 28. Accordingly, the Applicant proposes to provide a cut-out 30 along the inferior edge 28 of the cup 20 so as to negate this problem. As illustrated in later figures, the cut-out 30 is in the shape of an arc extending from one side of the cup 20 to the other. The cut-out 30 ensures an adequate thickness of polymer liner 24 covers the inner, articular surface of the metal shell 22 so as to prevent wear of the metal shell 22 in use. In addition, the cut-out 30 provides a useful reference point for the surgeon to help in the orientation of the cup for correct placement (e.g. to ensure the cup is not inserted upside down).

Figure 3:
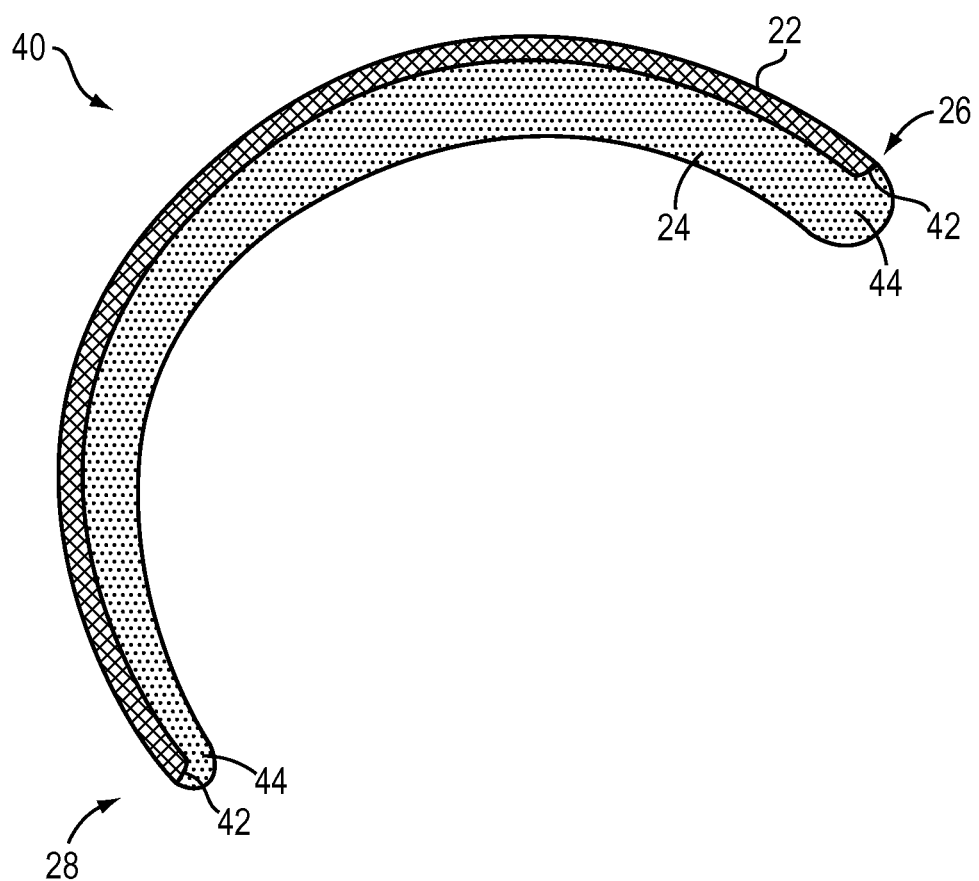
FIG. 3 shows a view similar to that of FIG. 2 but with a cut-out provided at an inferior edge of the cup to compensate for the displacement of the inner liner.

FIG. 3 shows a cup 40 according to an embodiment of the invention. The cup 40 is similar to that shown in FIG. 2 but with the cut-out 30 removed from the inferior edge 28. In addition, the metal shell 22 of the cup 40 is provided with inwardly inclined bevelled edges 42 and the polymer liner 24 is provided with a rounded edge 44 that extends over the edges 42 of the metal shell 22 to ensure no sharp edges are exposed to the patient or surgeon. Furthermore, it is advantageous to cover the metal edges 42 with the polymer edge 44 so as to prevent the metal shell 22 from scratching the femoral head in use, particularly in the event of inadvertent subluxation or dislocation.

Figure 4:
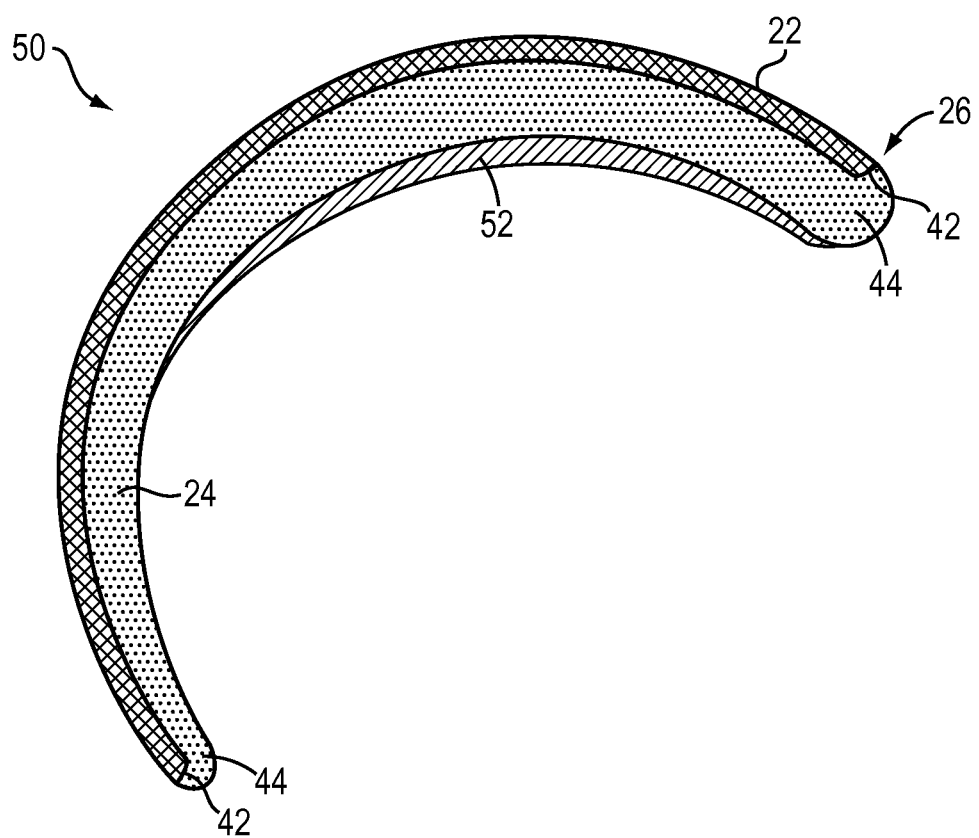
FIG. 4 shows a view similar to that of FIG. 3, wherein the pre-determined wear zone of the articular bearing surface of the polymer liner is provided with cross-linked polymer bonds.

FIG. 4 shows a cup 50 according to another embodiment of the invention. The cup 50 is similar to that shown in FIG. 3 but wherein a pre-determined wear zone 52 of the polymer liner 24 is provided with cross-linked polymer bonds. As discussed above, the wear zone 52 is provided in the region of maximum thickness of the polymer liner 24, the zone extending generally towards the supero-lateral edge 26 of the cup 50 from slightly below the centre of the cup 50. As illustrated, the cross-linked polymer bonds may penetrate into the polymer liner 24 in the shape of a part-spherical disc having a thickness which is at a maximum at its centre and tapers smoothly outwardly to a minimum thickness around its edges. Importantly, only a portion of the articular bearing surface of the cup 50 is cross-linked (i.e. in the wear zone) such that the remainder of the surface of the polymer liner 24 is not cross-linked. This helps to maintain the strength of the conventional polymer (in this case, polyethylene) throughout the majority of the polymer liner 24 and particularly in the thinnest and therefore more fragile regions of the polymer liner 24 while ensuring that the wear zone is modified by the cross-linked bonds to reduce the risk of wear.

The polymer liner 24 of the cup 50 of the present embodiment was formed by cold compressing a first layer of polyethylene powder including 2% of vitamin E to form a bulk layer and cold compressing a second layer of polyethylene powder including less than 0.2% vitamin E to form the wear zone. The powders of the first and second layers were then melted by hot compression moulding to form a single solid component.

Next, the component was irradiated (to provide approximately 100 kGy of absorbed radiation) so as to cross-link the molecules in the second layer; the molecules in the first layer being prevented from cross-linking due to the higher concentration of vitamin E. Lastly, the component was annealed by heating it below its melting point so as to encourage the vitamin E in the first layer to diffuse into the second layer to consume free radicals therein and thereby minimise the risk of oxidation of the second layer.

Figure 5:
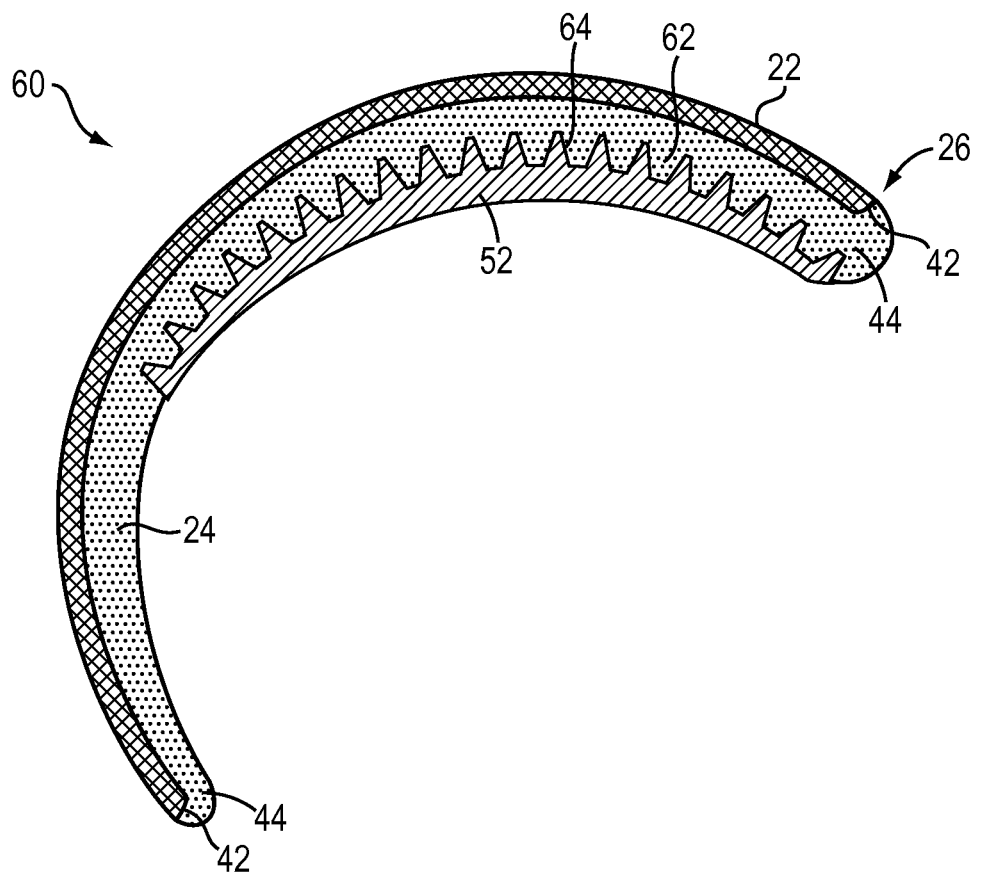
FIG. 5 shows a view similar to that of FIG. 4, but with an interdigitised interface between the portion of the polymer liner provided with cross-linked polymer bonds and the portion without cross-linked polymer bonds.

FIG. 5 shows a cup 60 according to a further embodiment of the invention. The cup 60 is similar to that shown in FIG. 4 but with an interdigitised interface 62 provided between the portion of the polymer liner 24 provided with cross-linked polymer bonds, also referred to as the wear zone 52, and the portion without cross-linked polymer bonds. The interdigitised interface 62 is provided by a series of spikes 64 of cross-linked polymer 52 which project into corresponding recesses in the non cross-linked polymer. The aim of the spikes 64 is to break up an otherwise sharp transition between the two types of polymer so as to provide a smoother transition between the two mechanical properties of the polymers to thereby reduce the risk of de-lamination at the interface 62.

The polymer liner 24 of the cup 60 may be formed in a similar way to that described above in relation to the cup 50 of FIG. 4. However, this time the step of cold compressing the first layer of polymer includes stamping the recesses in the first layer, in the region of the wear zone, and the step of cold compressing the second layer of polymer includes filling the recesses with the powder for the second layer before stamping the shape of the articular surface of the cup 60.

FIGS. 6A through 6D show various views of an acetabular cup prosthesis 70 in accordance with a particular embodiment of the invention, fitted with an impactor cap 72 in accordance with another embodiment of the invention. The acetabular cup 70 is essentially as shown in FIG. 4 but including further features on the external surface of the metal shell 22 for improved fixation in a prepared bone cavity. The external surface of the metal shell 22 is more clearly illustrated in FIG. 17 and so will be described in more detail below. In addition, the cup 70 shown in FIGS. 6A through 6D includes two relatively large polymer loops 74 extending from the edge of the polymer liner 24.

These loops 74 are configured as a means for attaching the cup 70 to an introducer configured for inserting the cup 70 into a patient. Some examples of suitable introducers are shown in FIGS. 15A through 15D and FIGS. 16A and B and will be described in more detail below.

In the embodiment shown in FIGS. 6A through 6D, each loop 74 is integrally moulded to the polymer liner 24. In addition, each loop 74 has a first end 76 located at the inferior end 28 of the cup 70 (i.e. in the region of the cut-out) and a second end 78 located at the opposite, supero-lateral end 26 of the cup 70. Notably, the loops 74 are thickest at their first and second ends 76, 78 so as to provide more support at these joints.

It will be understood that after insertion of the cup 70 into a patient, the loops 74 will be removed by cutting the first and second ends 76, 78 from the polymer liner 24 so as to leave the polymer liner 24 with a relatively flush, smooth surface.

The impactor cap 72 in FIGS. 6A through 6D is shown in more detail in FIGS. 14A through 14D. However, as can be seen from the present figures, the impactor cap 72 is designed to fit within the cup 70 and has a flange 80 around its peripheral edge which is shaped to rest on the edge 44 of the polymer liner 24. Thus, the impactor cap 72 is shaped to take account of the cut-out at the inferior edge 28 of the cup 70. The flange is also provided with four semi-circular cut-outs 82, one around each of the first and second ends 76, 78 of the loops 74 so as to allow the loops 74 to project outwardly from the edge 44 of the polymer liner 24. In addition, the impactor cap 72 includes a location means in the form of a recess 84 which is shaped such that a cooperating projection can only be received in the recess 84 in one orientation. In this embodiment, the recess 84 comprises a straight side 86 and a curved side 88 which together form the outline of a capital D. The recess 84 is provided so that it is only possible for a surgeon to attach an introducer to the cup 70 in the correct orientation as will be described in more detail below.

Figure 7:
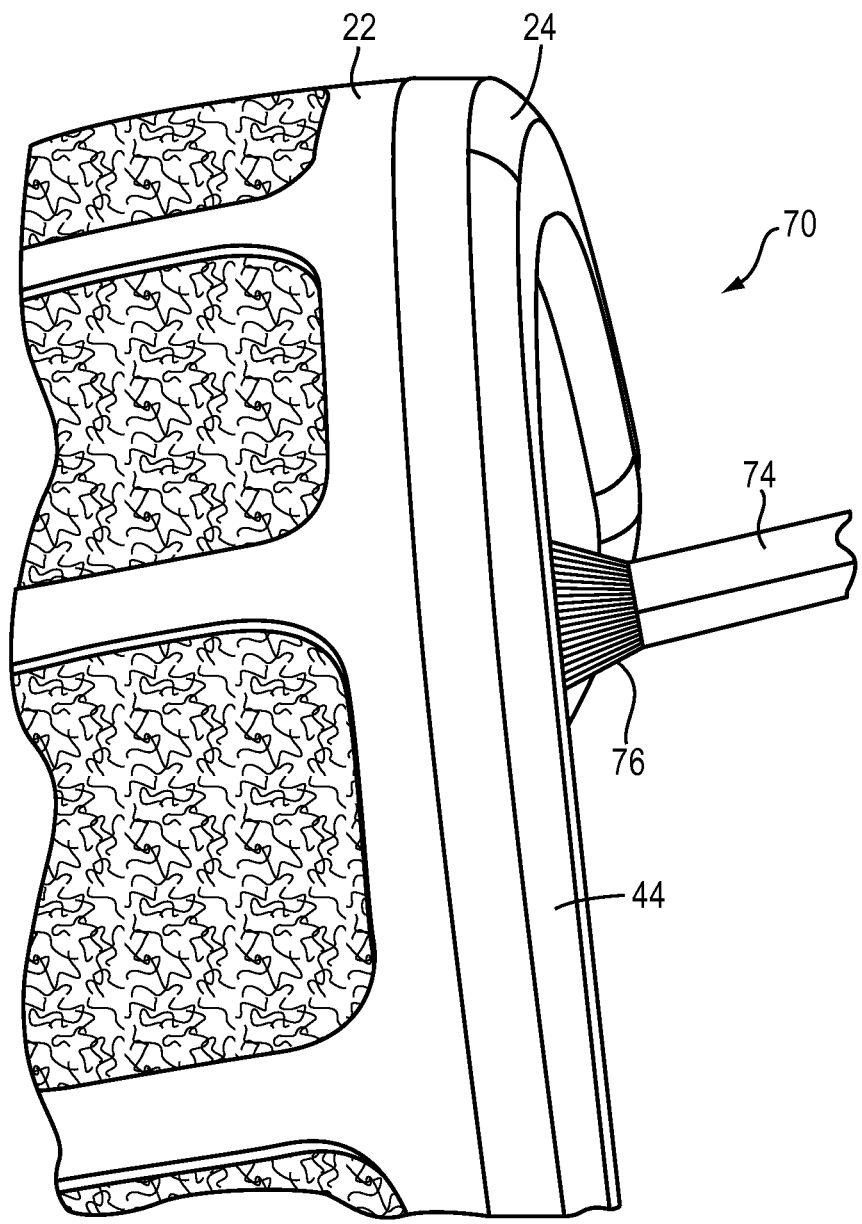
FIG. 7 shows a part-perspective view of the acetabular cup shown in FIGS. 6A through 6D, without the impactor cap, but showing in detail the base of one of the introducer attachment loops.

FIG. 7 shows an enlarged view of a portion of the cup 70 without the impactor cap 72. More specifically, FIG. 7 shows an enlarged view of the first end 76 of one the loops 74, showing the increased thickness in this region. Thus, it can be seen that in this embodiment, the first end 76 (and the second end 78, not shown) has the form of a frusto-conical foot which is thickest at its base.

Figure 8:
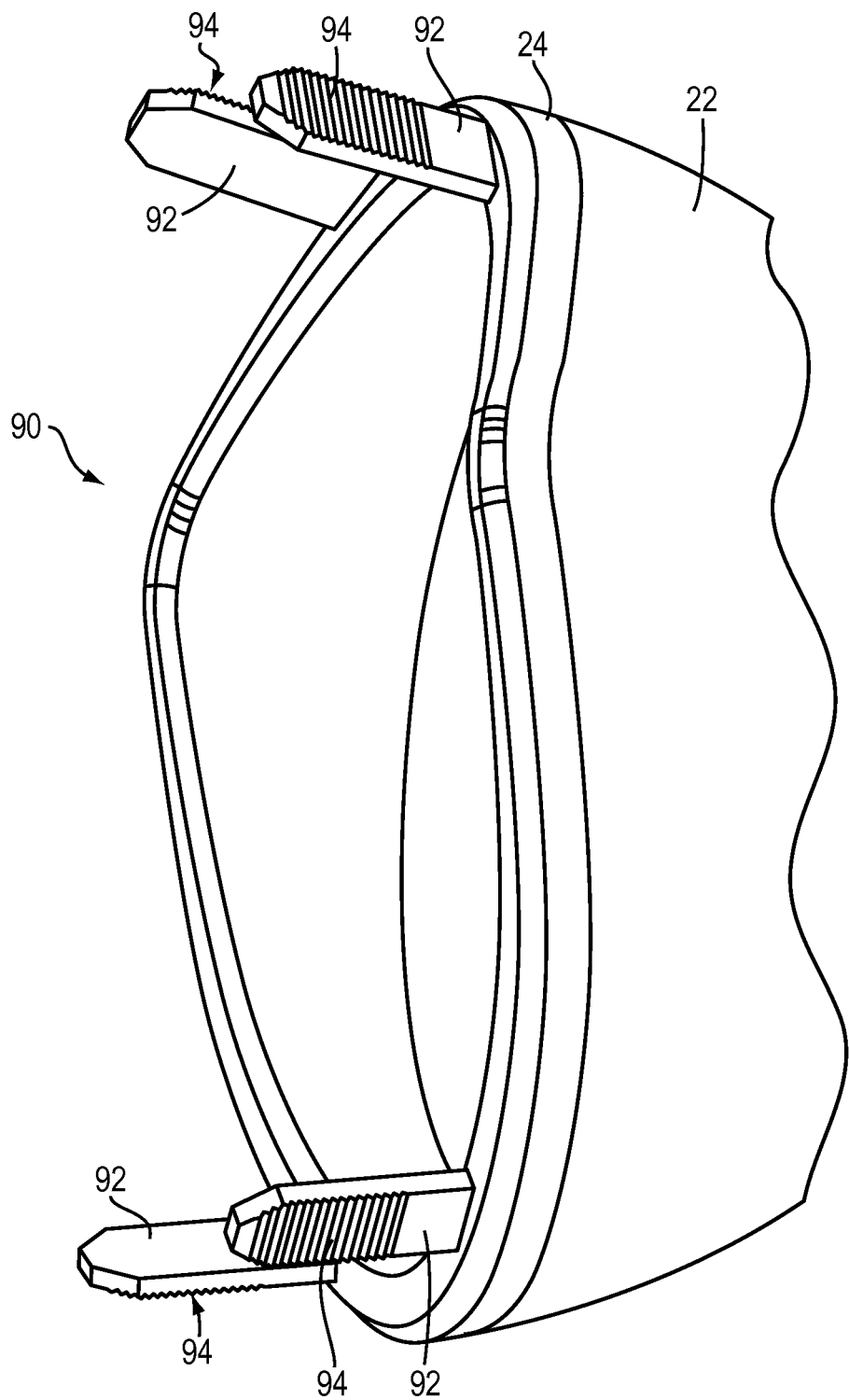
FIG. 8 shows a side part-perspective view of an acetabular cup prosthesis in accordance with a further embodiment of the invention, including serrated introducer attachment elements.

FIG. 8 shows an acetabular cup prosthesis 90 having an alternative attachment means in the form of four polymer bands 92 projecting from the edge of the polymer liner 24. The bands are integrally formed with the polymer liner 24 and include a serrated outer surface 94 towards their free ends. It will be understood that each of the serrated surfaces 94 are configured for use with a device configured to lock onto the serrations, much like in the form of a traditional cable tie. The device for locking onto the serrations will be provided on an introducer configured for use with the cup 90. Ideally, the device will be configured to allow the serrated surface 94 to be passed through it in one direction but to prevent the serrated surface 94 from passing through it in the opposite direction. As before, when the cup 94 is in position, the bands 92 will be cut from the polymer liner 24 to leave a smooth external surface.

Figure 9:
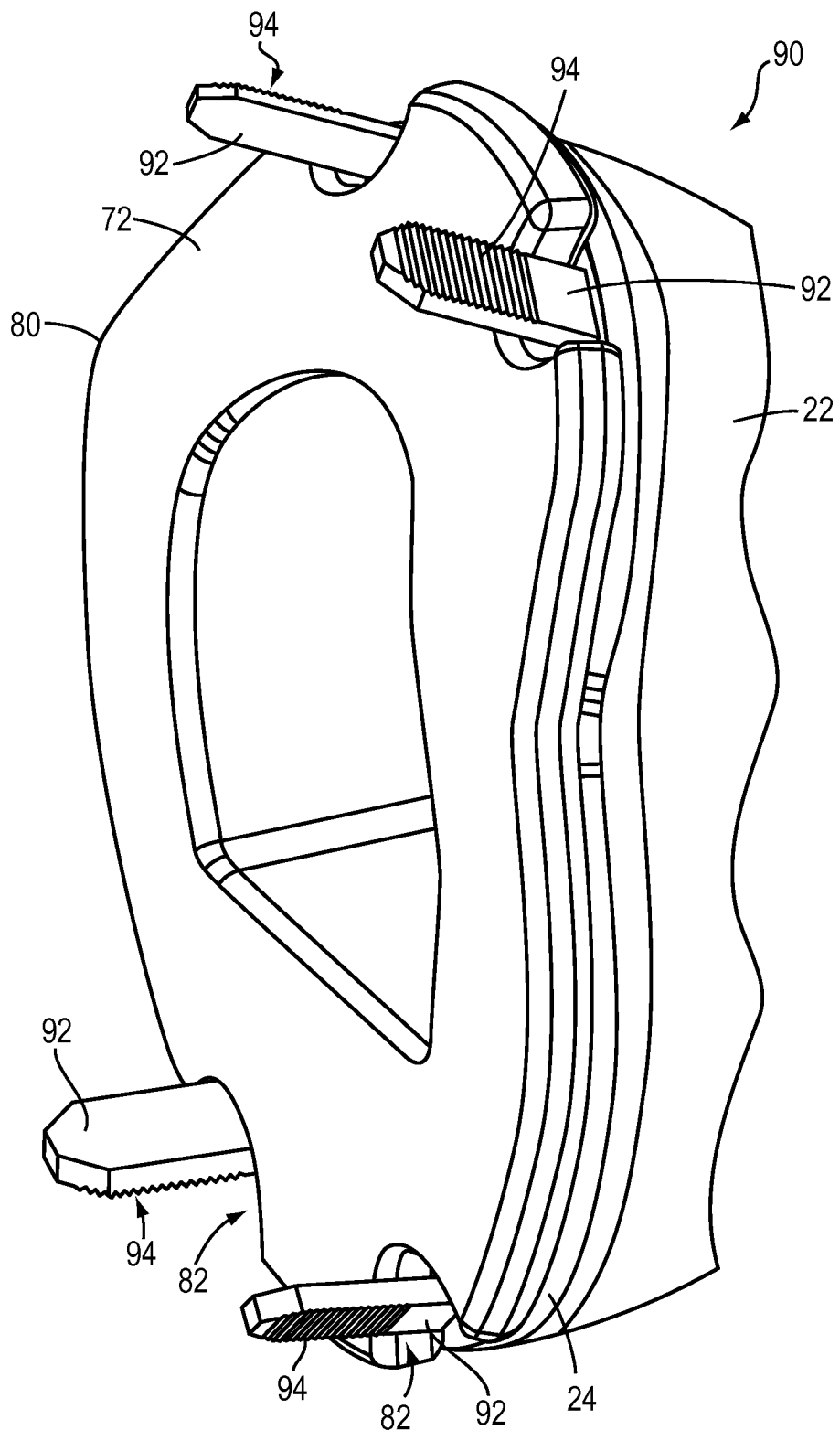
FIG. 9 shows a view similar to that of FIG. 8 but with an impactor cap fitted to the cup.

FIG. 9 shows the cup 90 of FIG. 8 fitted with the impactor cap 72 as described above. It is clear from this view that the impactor cap 72 will only fit onto the cup 90 one way due to the angling of the flange 80 which accommodates the cut-out at the inferior edge of the cup 90. As above, the four semi-circular cut-outs 82 in the flange 80 allow the attachment means (in this case the bands 92) to project outwardly from the edge 44 of the polymer liner 24.

Figure 10:
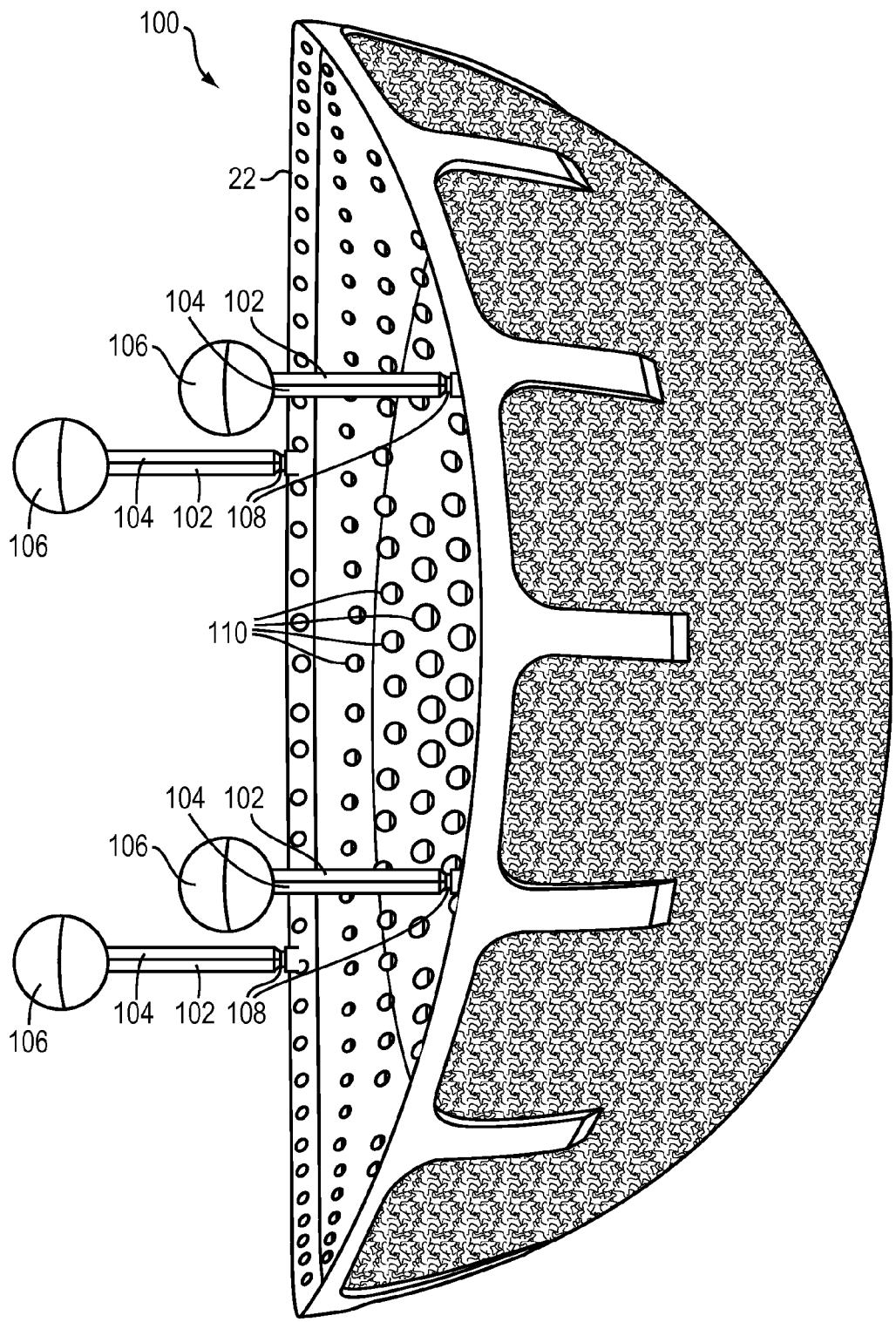
FIG. 10 shows a side part-perspective view of a metal shell of an acetabular cup prosthesis in accordance with another embodiment of the invention, including introducer attachment elements in the form of protruding metal rods.
Figure 11:
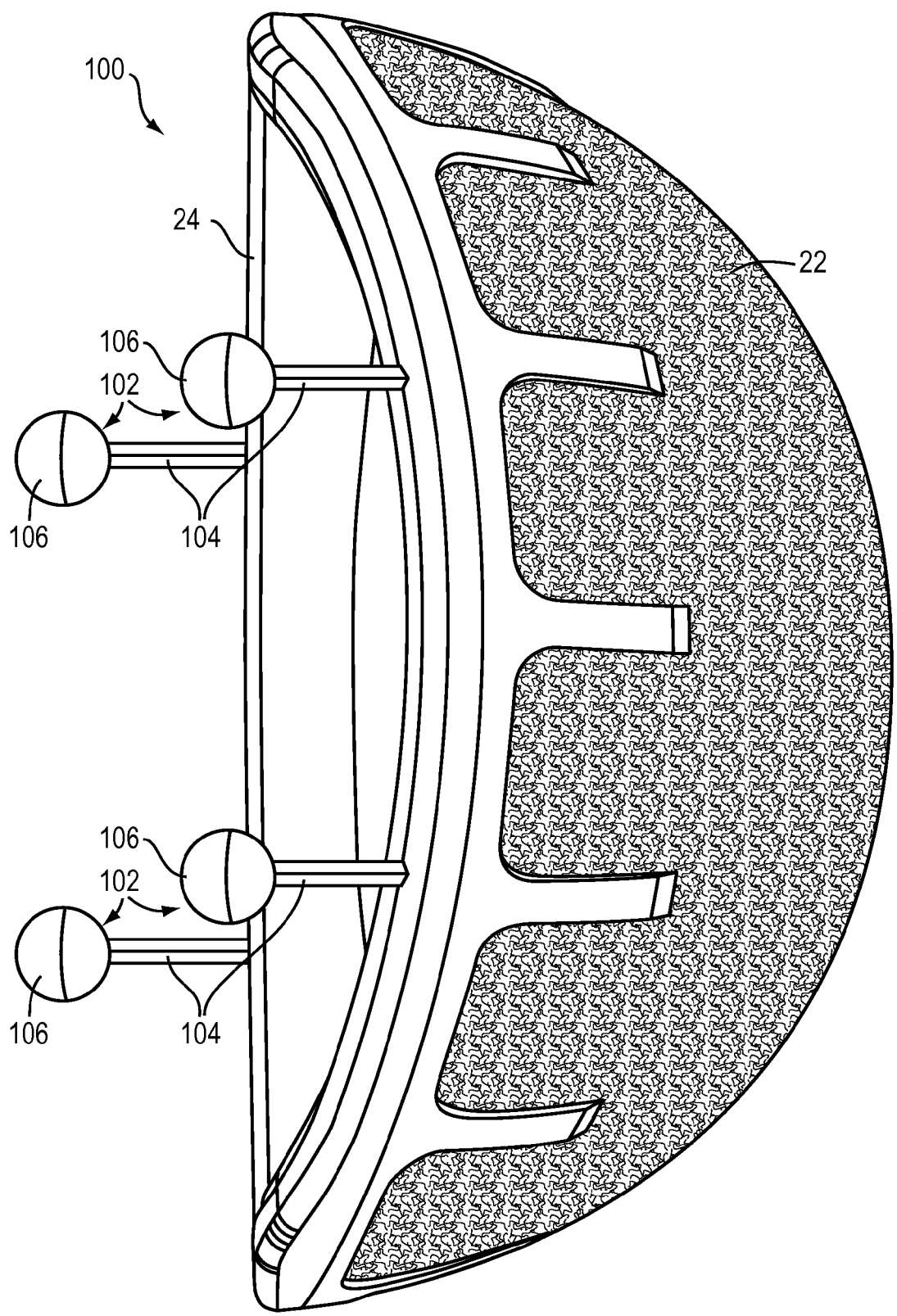
FIG. 11 shows a view similar to that of FIG. 10 but with a polymer liner moulded into the metal shell and around the metal rods.
Figure 12:
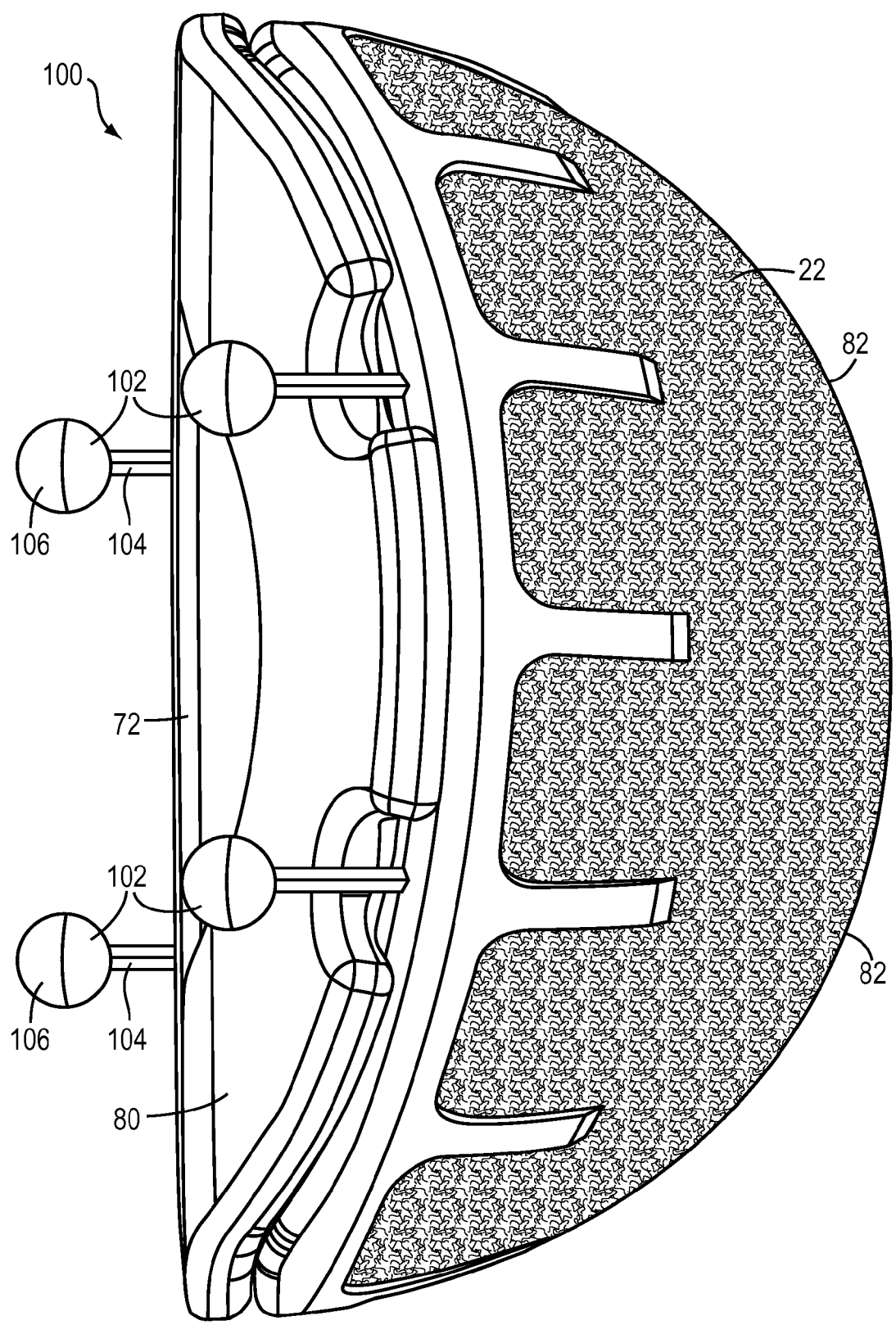
FIG. 12 shows a view similar to that of FIG. 11 but with an impactor cap fitted to the cup.

A further attachment means is shown in FIGS. 10 to 12 in a further acetabular cup 100 according to another embodiment of the invention. In this case the attachment means is in the form of four metal rods 102. The metal rods 102 may be integrally formed with the metal shell 22 as shown in FIG. 10. Each rod 102 includes a shaft 104 having a large spherical ball 106 mounted on its free end. Close to the interface between the rod 102 and the metal shell 22, there is provided a neck 108 which is thinner than the rest of the shaft 104. The neck 108 is provided so that after the cup 100 has been inserted into a patient, the rod 102 can be twisted to cause the neck 108 to break and thereby enable the depending portion of the rod 102 to be removed. Although not shown, it will be understood that the cup 100 is configured for use with an introducer that can grip onto the spherical balls 106 to thereby secure the cup 100 to the introducer.

It will also be seen from FIG. 10 that the internal surface of the metal shell 22 is provided with a plurality of small spherical cut-outs 110. These are provided for the mechanical fixation of the polymer liner 24 to the metal shell 22, as will be described in more detail with reference to FIG. 21A.

FIG. 11 shows a view similar to that of FIG. 10 but with the polymer liner 24 attached to the metal shell 22. Thus, it can be seen that the polymer liner 24 is formed around the base of the rods 102 such that the rods 102 project from the polymer liner 24. Notably, the necks 108 are below the surface of the polymer liner 24 so that when the rods 102 are removed, the remaining portions of the shafts 104 are encapsulated by the polymer liner 24 so as to protect the surrounding tissue from damage by these parts.

The cup 100 is shown in FIG. 12 with the impactor cap 72 in place. As previously, the four semi-circular cut-outs 82 in the flange 80 allow the attachment means (in this case the rods 102) to project outwardly from the edge 44 of the polymer liner 24.

Figure 13:
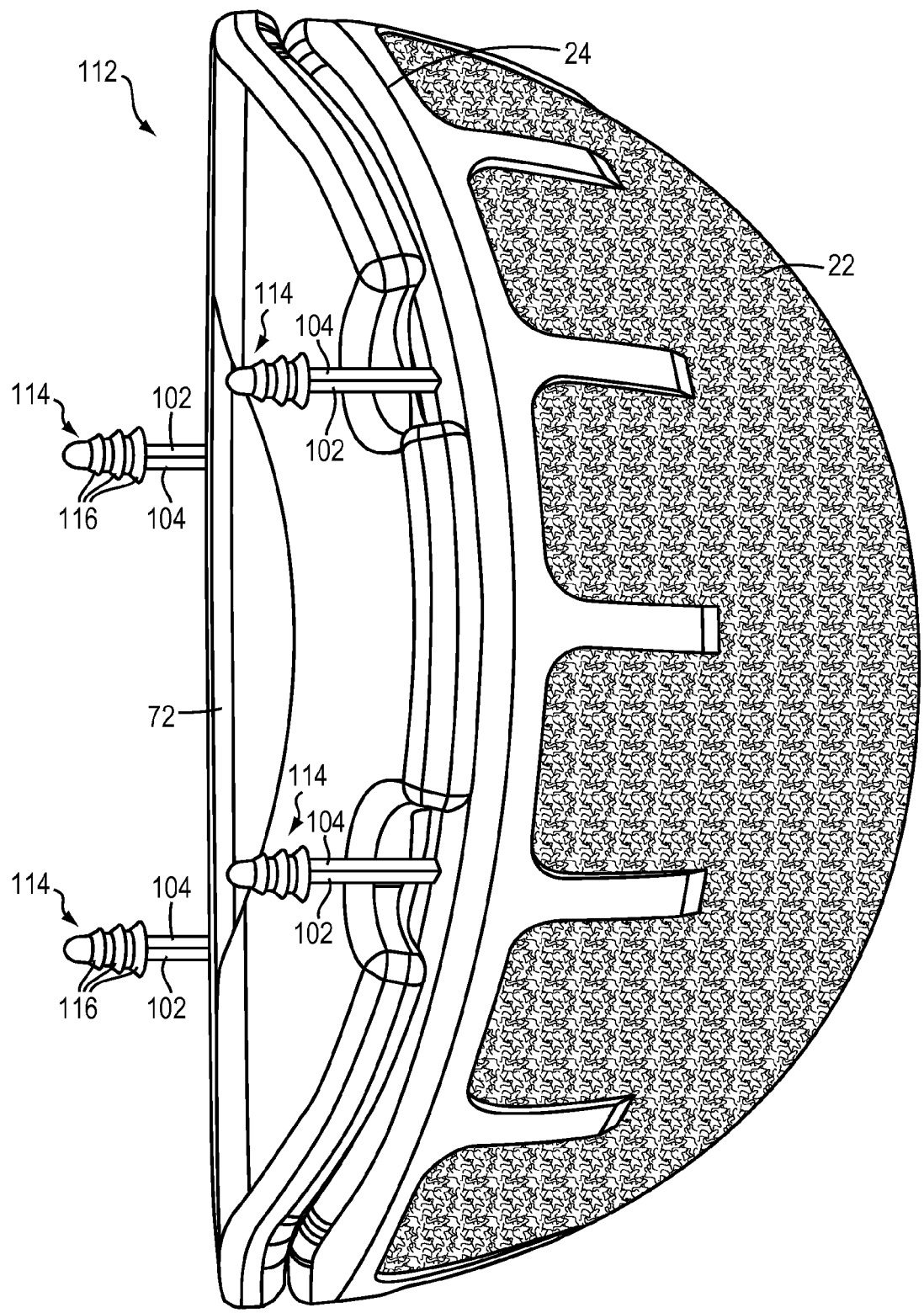
FIG. 13 shows a view similar to that of FIG. 12 but with the ends of the metal rods fitted with conical portions at their tips.
Figure 15C:
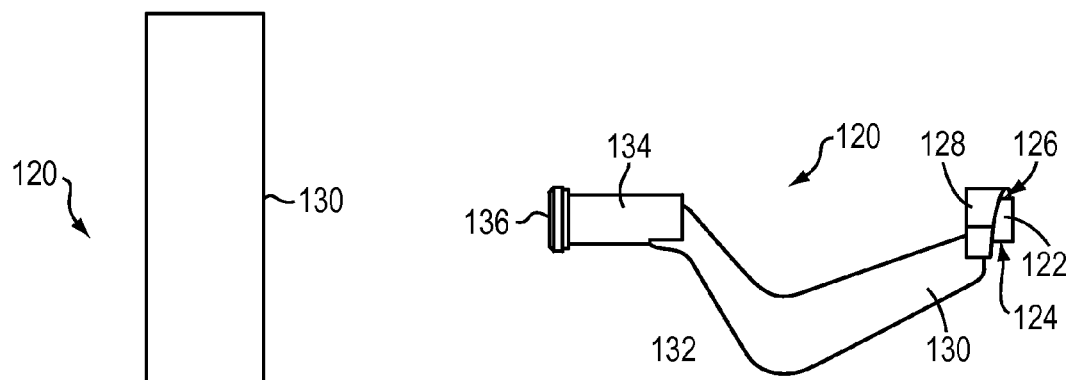
FIG. 15C shows a side elevation view of the introducer shown in FIG. 15A.
Figure 15B:
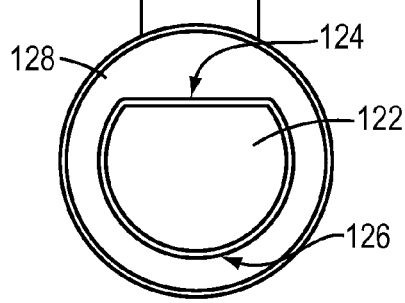
FIG. 15B shows an end elevation view of the introducer shown in FIG. 15A.
Figure 15D:
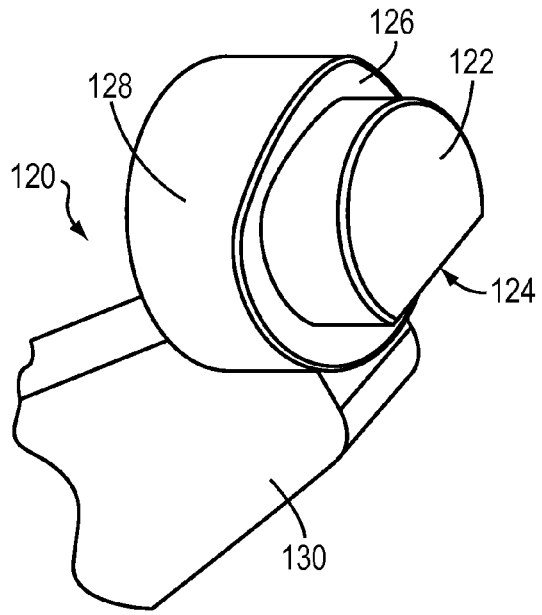
FIG. 15D shows a part-perspective view of the end of the introducer shown in FIG. 15A, configured for attachment to an impactor cap such as that shown in FIGS. 14A-D.
Figure 15A:
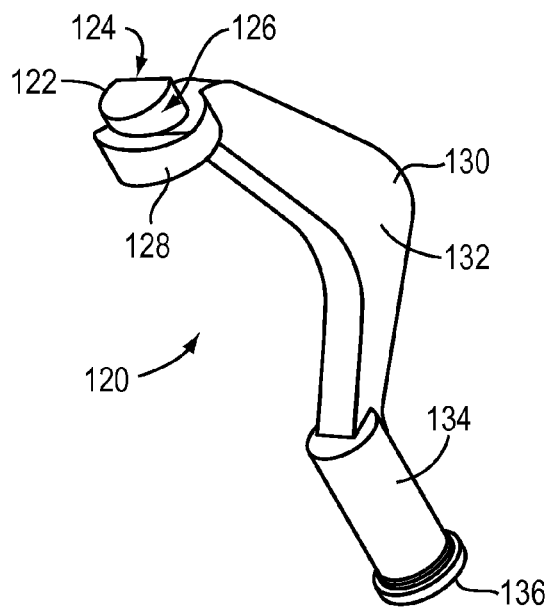
FIG. 15A shows a simplified perspective view of an introducer in accordance with an embodiment of the present invention.

FIG. 13 shows another acetabular cup prosthesis 112, according to an embodiment of the present invention, also fitted with the impactor cap 72. In this case, the attachment means is identical to that shown in FIGS. 10 to 12 except that the spherical balls 106 on the ends of each shaft 104 are replaced by a generally conical structure 114. The conical structure 114 is composed of a series of three conical portions 116 stacked with their tips towards the free end of the rod 102, each conical portion 116 decreasing in size toward the free end of the rod 102.

In alternative embodiments, the necks 108 may not be provided in the rods 102 and the rods 102 may simply be cut adjacent the polymer liner 24 when they are to be removed.

Figure 6A:
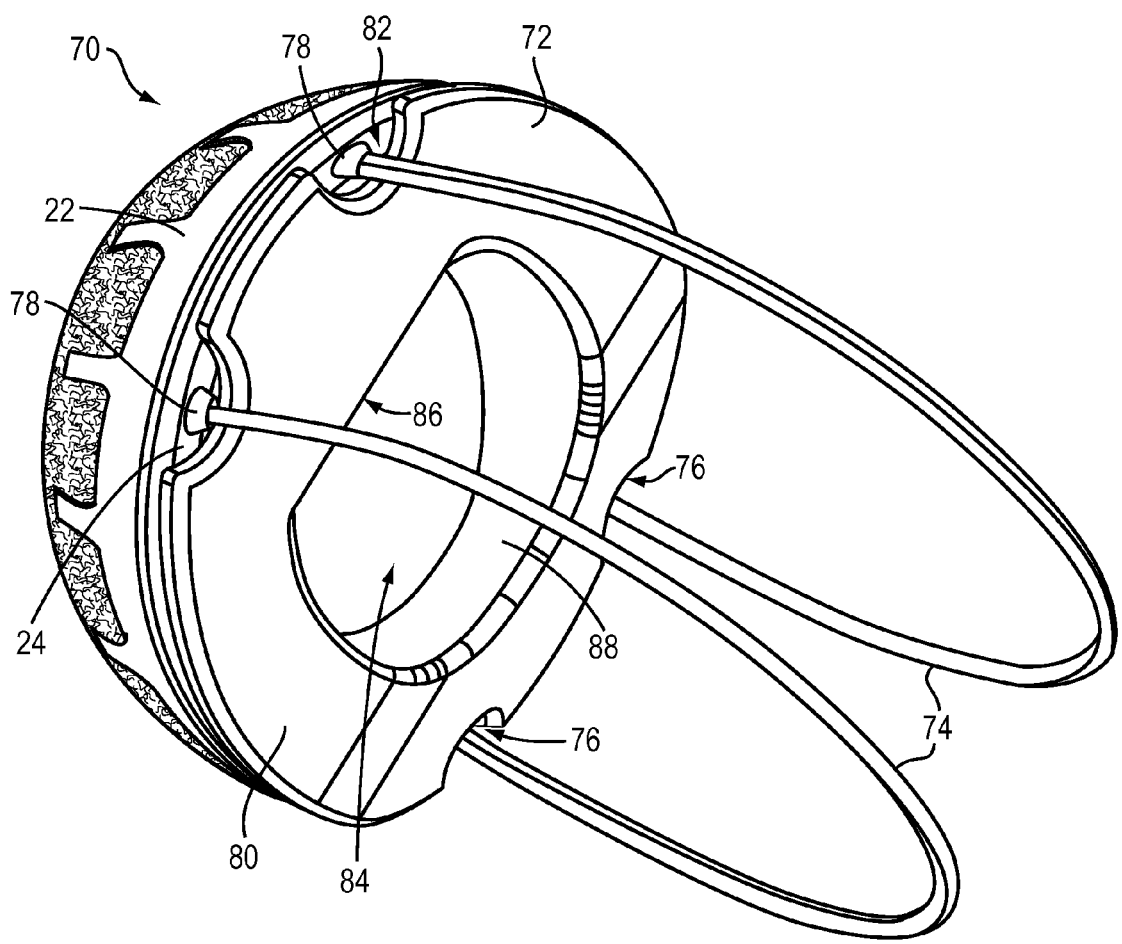
FIG. 6A shows a perspective view from a first side of an acetabular cup prosthesis in accordance with one embodiment of the invention, fitted with an impactor cap in accordance with another embodiment of the invention.
Figure 6B:
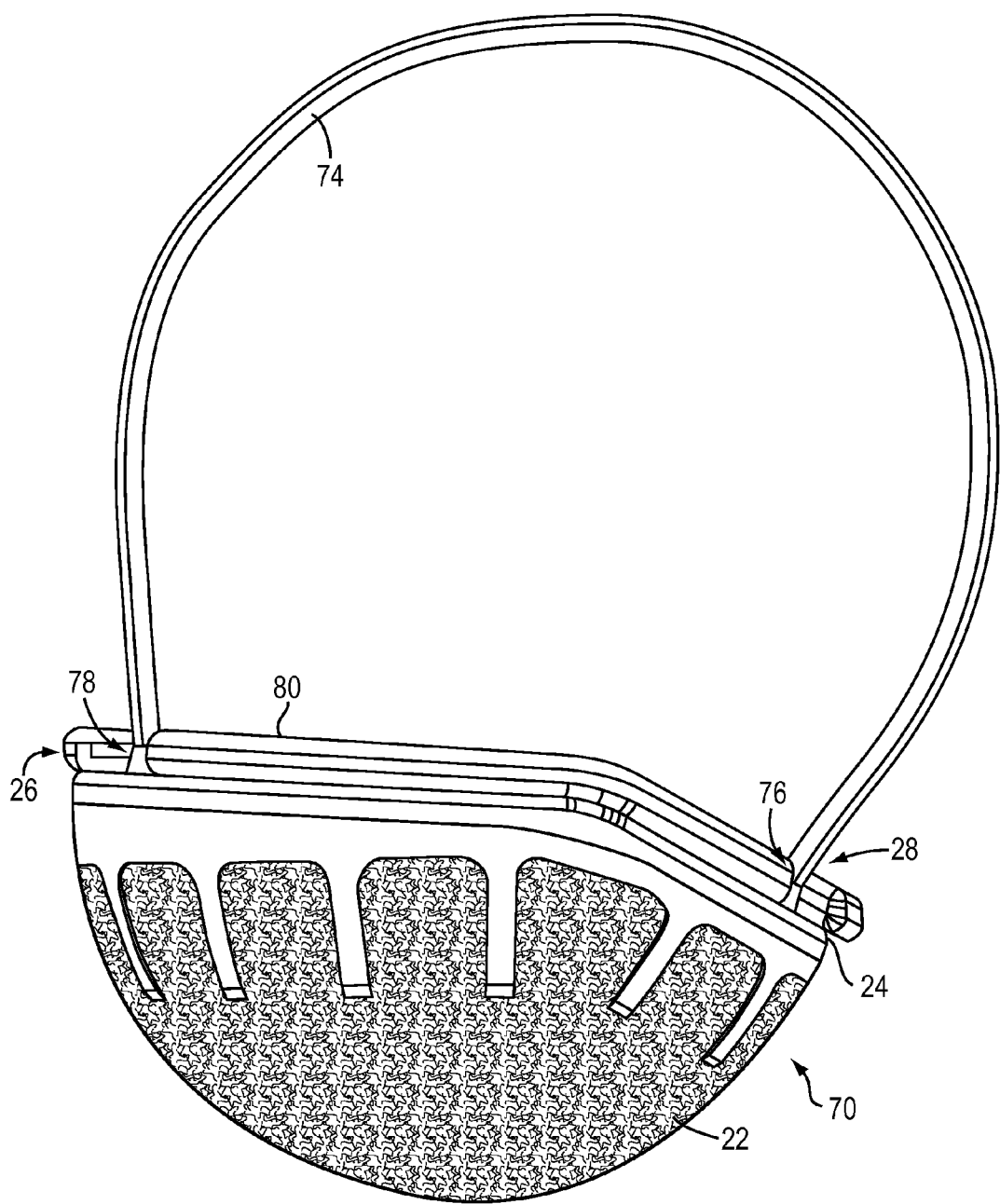
FIG. 6B shows a side elevation view of the acetabular cup and impactor cap of FIG. 6A.
Figure 6C:
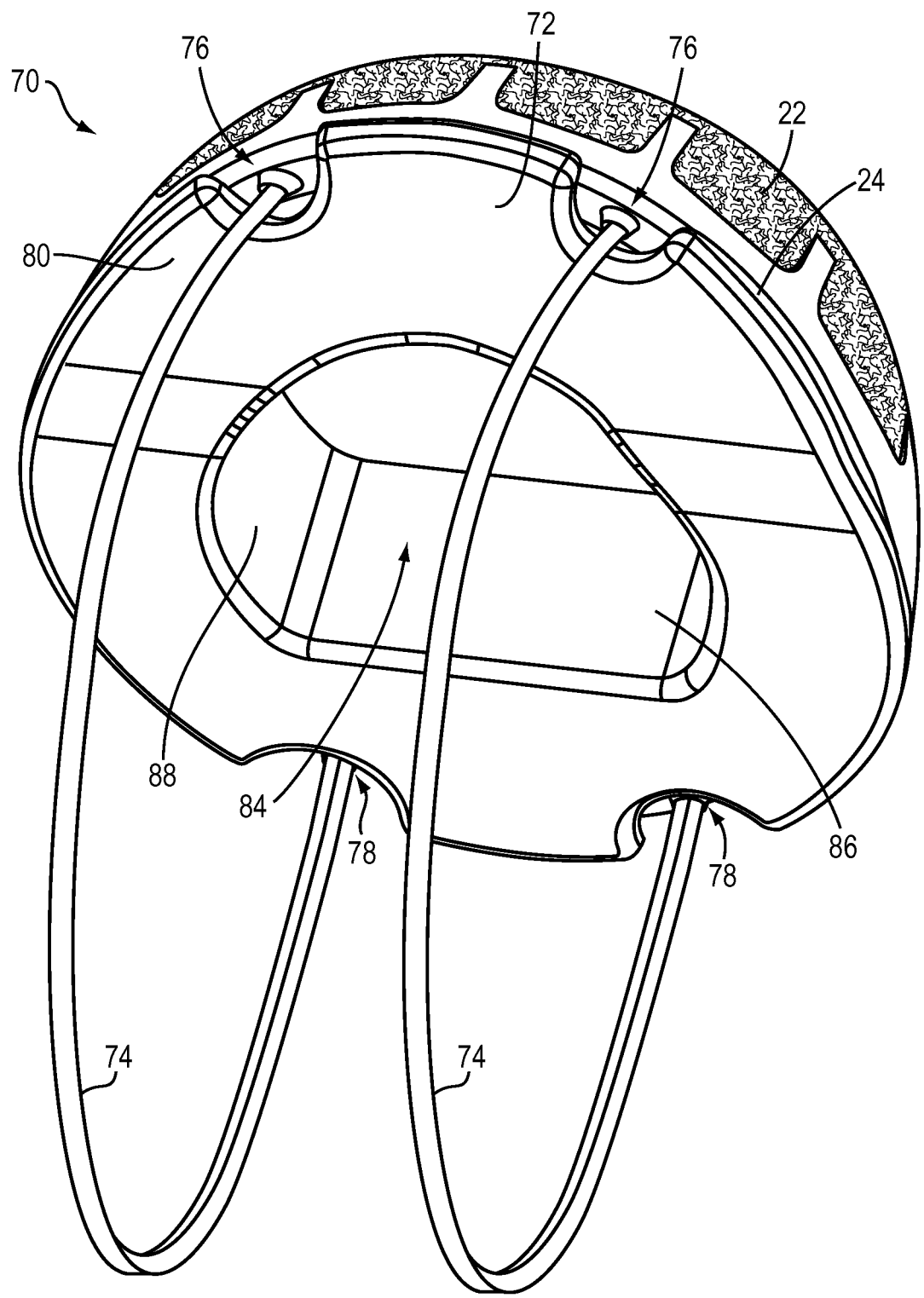
FIG. 6C shows a part-perspective view of the acetabular cup and impactor cap of FIG. 6A, from a second side.
Figure 6D:
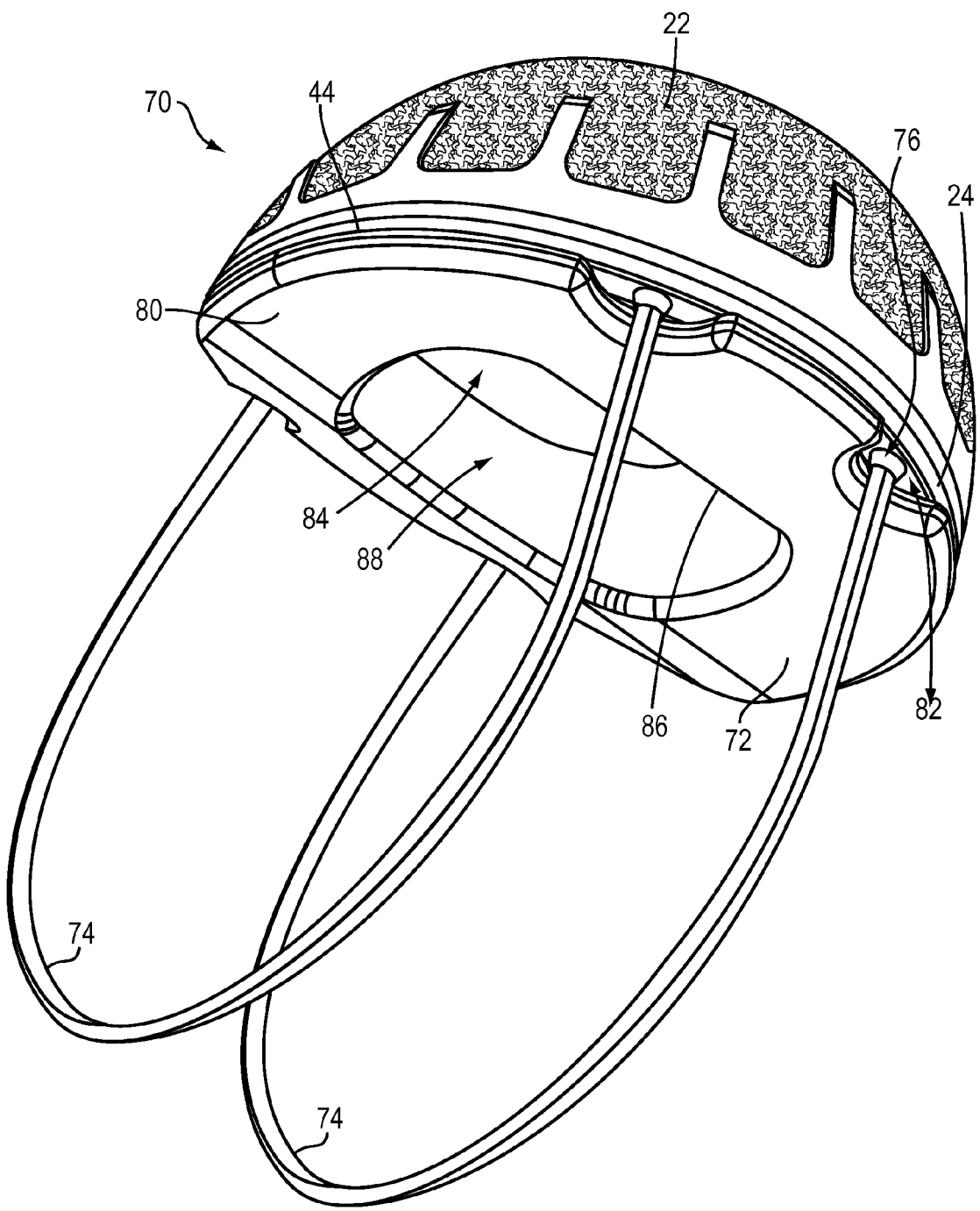
FIG. 6D shows a part-perspective view of the acetabular cup and impactor cap of FIG. 6A, showing a close-up of the cup edge and initial portions of the introducer attachment loops.

FIGS. 14A through 14D show various views of the impactor cap 72 first introduced in relation to FIG. 6A. Thus, it can be seen that the impactor cap 72 includes a large bulbous exterior surface 89 on its underside which is shaped to precisely match the shape of inner surface of the polymer liner 24. Accordingly, the impactor cap 72 provides additional strength to any thin-walled acetabular cup, such as those described above in accordance with different embodiments of the present invention, and therefore helps to maintain the shape of the cup as it is impacted into a prepared bone cavity, even where a slight press-fit is required.

FIGS. 15A through 15D show various views of an introducer 120 according to one embodiment of the present invention. The introducer 120 includes a mating means in the form of a projection 122 that is configured to fit into the recess 84 of the impactor cap 72 when inserted into an acetabular cup such as those described above. Thus the projection 122 has a straight side 124 configured to mate with the straight side 86 of the recess 84 and a curved side 126 configured to mate with the curved side 88 of the recess 84. Accordingly, it is only possible for the introducer 120 to be attached to the impactor cap 72 in one orientation. As explained above, since the impactor cap 72 is itself only capable of being attached to a cup in one orientation, this ensures that the cup is always held on the introducer 120 in the correct orientation for insertion into a patient.

The projection 122 extends from a head 128 of the introducer 120, which itself is mounted on the end of a handle 130. The handle 130 is provided with a kink 132 to avoid impingement with the body of the patient during insertion. The handle 130 is also provided with a cylindrical grip 134 having an end 136 suitable for hitting with a hammer or similar instrument to force the cup into position. The grip is aligned with the axis of the cup such that the end 136 is orthogonal thereto and is therefore configured to transmit a force applied to it through the axis of the cup.

The introducer 120 also includes a gripping and tightening means for locking onto the attachment means of a cup to secure it to the introducer. This means has been omitted from FIGS. 15A through D for clarity but is shown in FIGS. 16A and B described below.

In an alternative embodiment, not shown, the impactor cap 72 may be integral with the head 122 of the introducer 120.

Figures 16A, 16B:
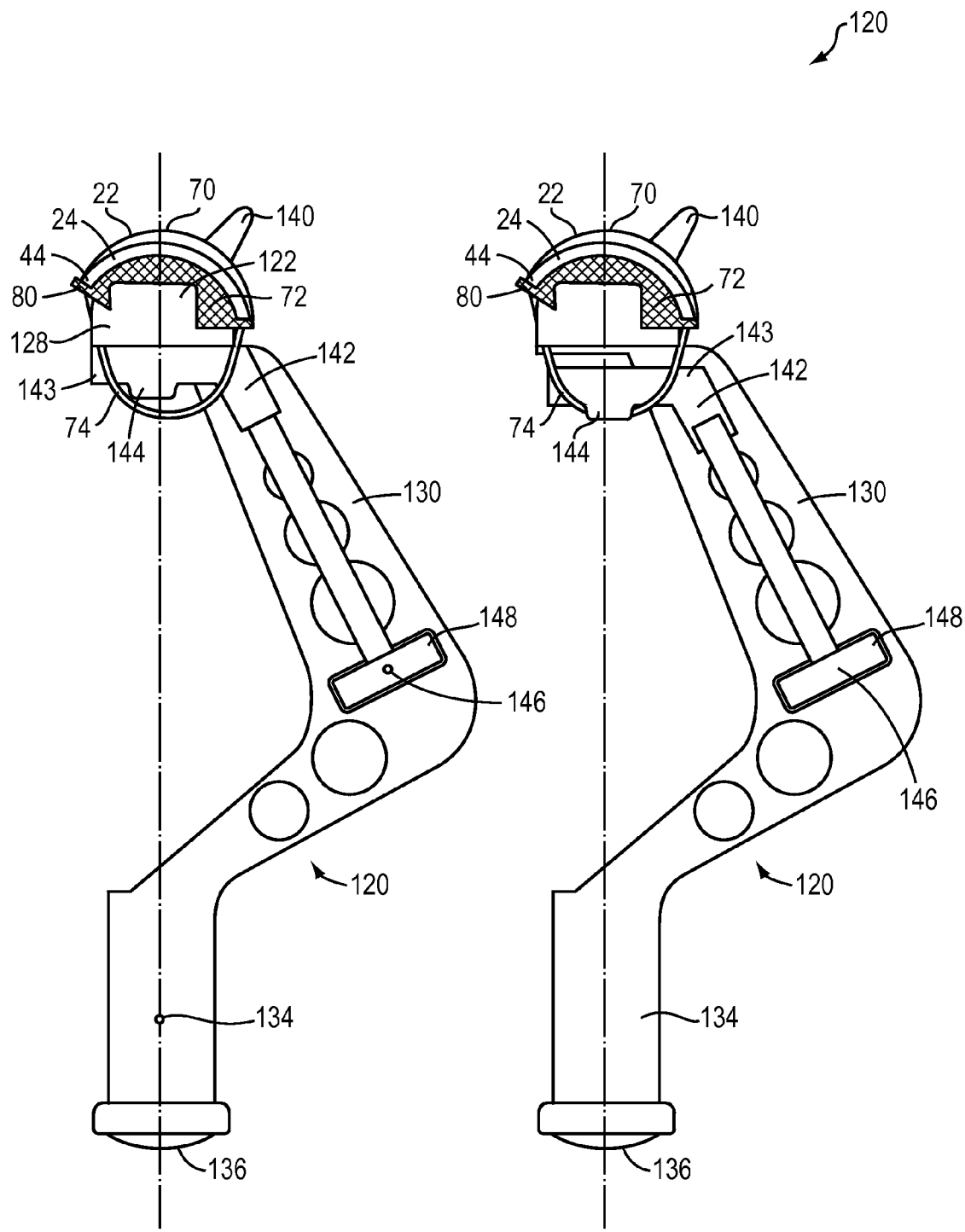
FIG. 16A shows a side elevation view of the introducer shown in FIGS. 15A-D inserted into an impactor cap similar to that shown in FIGS. 14A-D, provided in an acetabular cup prosthesis similar to that shown in FIGS. 6A-D.
FIG. 16B shows the apparatus of FIG. 16A after tension has been applied by the introducer to securely attach the acetabular cup thereto.

FIG. 16A shows a side elevation view of the introducer 120 inserted into the impactor cap 72, which in turn is inserted into an acetabular cup prosthesis 70 similar to that shown in FIGS. 6A-D but further including a modular peg 140 as will be described in more detail below in relation FIG. 17. More specifically, the projection 122 of the introducer 120 is located within the recess 84 of the impactor cap 72 and the bulging surface of the impactor cap 72 is placed into contact with the inner polymer liner 24 of the cup 70. The flange 80 of the impactor cap 72 is located on the edge 44 of the polymer liner 24 and the loops 74 are arranged to extend past either side of the head 128 of the introducer 120.

As shown in FIGS. 16A and B, the introducer includes a gripping and tightening means 142 for locking onto the loops 74 of the cup 70. The means 142 includes two opposed feet 143, each provided with a projecting ear 144 arranged such that each loop 74 can be wound around an ear 144 to retain the loops 74 thereon. The means 142 further includes a tightening mechanism 146 which, as shown in FIG. 16B, retracts the feet 143 and ears 144 away from the head 128 on rotation of a thumb screw 148. It will be understood that retracting the ears 144 also retracts the loops 74 hooked thereon and as such tension is applied between the cup 70 and the introducer 120 so as to hold the cup 70 securely thereon.

FIG. 16B illustrates the assembly ready for insertion of the cup 70 into a patient, after tension has been applied. As mentioned above, the cup 70 may be impacted into the prepared bone by hammering the end 136 of the introducer 120. Once in position, the surgeon will release the tension by unscrewing the screw 148 to lower the feet 143. This in turn will release the tension on the loops 74 allowing them to be disengaged from the ears 144. The introducer 120 and impactor cap 72 will then be removed from the cup 70 and the loops 74 will be cut close the polymer edge 44.

Figure 17:
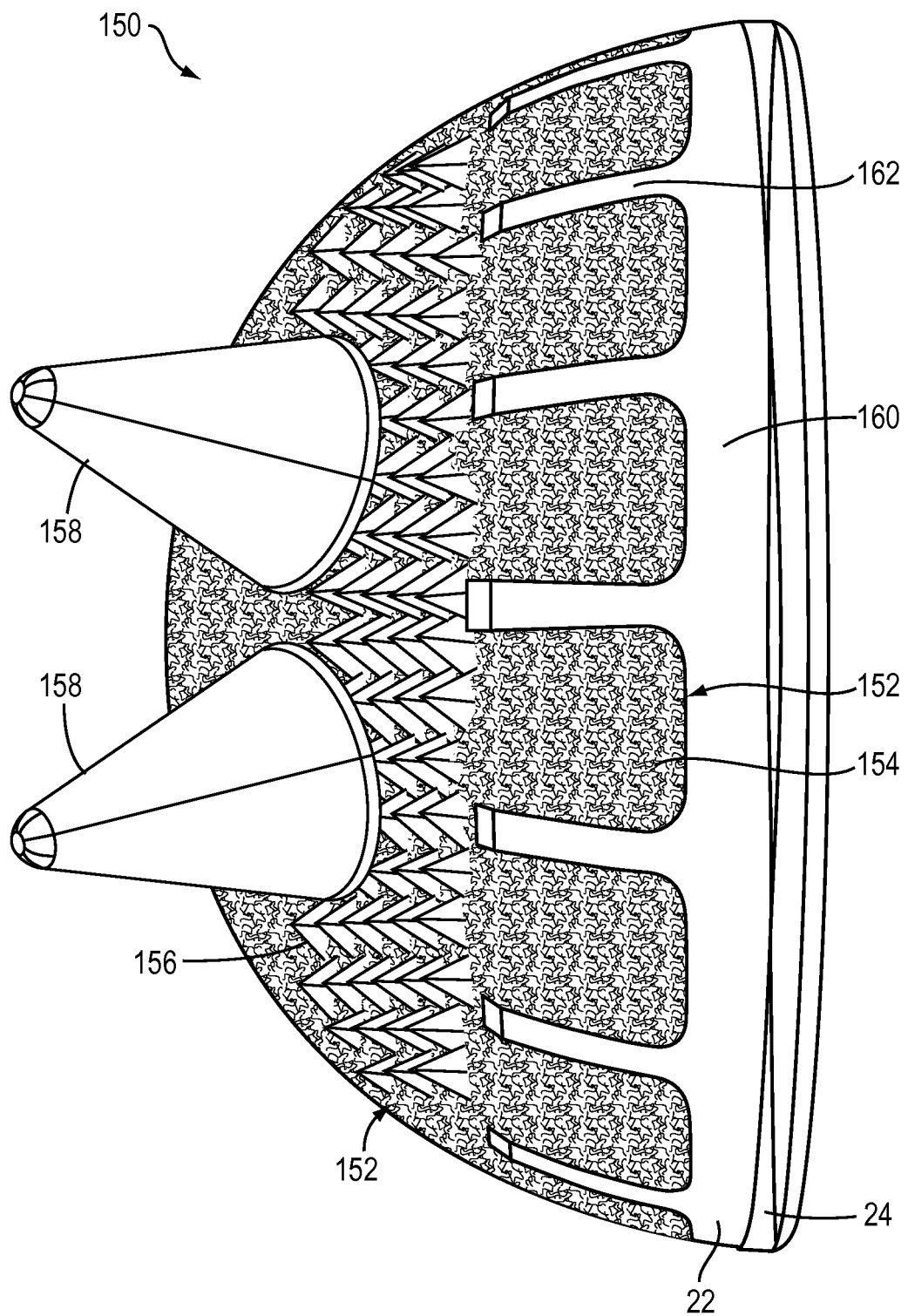
FIG. 17 shows a part-perspective view of an outer portion of an acetabular cup according to an embodiment of the present invention.

FIG. 17 shows a part-perspective view of an outer superolateral portion of an acetabular cup 150 according to an embodiment of the present invention. The cup 150 is similar to that shown in FIGS. 6A to 6D and 7 to 13. Accordingly, it includes a metal outer shell 22 and a polymer inner liner 24. The external surface of the metal shell 22 is provided with a number of features to aid fixation of the thin-walled cup 150 in a prepared bone cavity. The majority of the surface is covered with a truncated-bead lattice 152 which is designed to sit on the surface of the bone cavity. The lattice 152 includes a rough exterior provided by a plurality of microspikes 154 which are configured to aid initial fixation by increasing the frictional resistance between the bone and the cup 150. The lattice 152 also provides a porous structure for bone in-growth and a plurality of undercuts to allow bone to lock onto the cup 150. Each of these features will be shown in greater detail in later figures. The surface of the metal cup 22 is also provided with an array of conical fixation spikes 156 which are configured to penetrate into the bone by approximately 2 mm so as to aid fixation in the absence of a strong press-fit which is not possible with such a thin-walled cup 150. The array is provided in a band across the most proximal region of the cup 150, as defined in relation to the body of the patient. Accordingly, on impaction the spikes 156 penetrate into the bone before the lattice 152 contacts the surface of the cavity. The cup 150 is also provided with two optional modular pegs 158 which are configured for selective attachment to the exterior of the metal shell 22 to provide additional fixation, if required. The modular pegs 158 are provided on either side of the centre of the array of fixation spikes 156. Each modular peg 158 is conical and has a rounded tip. The modular pegs project normal to the external surface of the metal shell 22.

As seen in FIG. 17, the external surface of the metal shell 22 is provided with a rim 160 around the periphery of the cup 150 which is free from all of the above-mentioned fixation features. This is advantageous in providing maximum strength around the periphery of the cup 150, particularly in the inferior region where both the metal shell 22 and the polymer liner 24 are thin. Furthermore, a series of strengthening ribs 162 are provided in the region adjacent the periphery of the cup 150. The strengthening ribs 162 extend in a longitudinal direction towards the pole of the metal shell 22 and terminate close to the array of fixation spikes 156, which it will be noted are provided in the region of maximum thickness of the cup 150 (i.e. on the opposite surface of the cup from the wear zone). The rim 160 and strengthening ribs 162 therefore help to stiffen the metal shell 22 in where it and/or the polymer shell 24 are thinnest. In this particular embodiment, the metal shell 22 is configured to be approximately 1 mm thick around the rim and in the region of the strengthening ribs 162 but becoming thicker to approximately 3 mm of thickness in the region adjacent the intended wear zone This increased thickness provided greater support for the fixation spikes 156 and modular pegs 158. Where the lattice 152 is present, the combined thickness of the metal shell 22 and the lattice 152 is approximately 1 mm.

Figure 18:
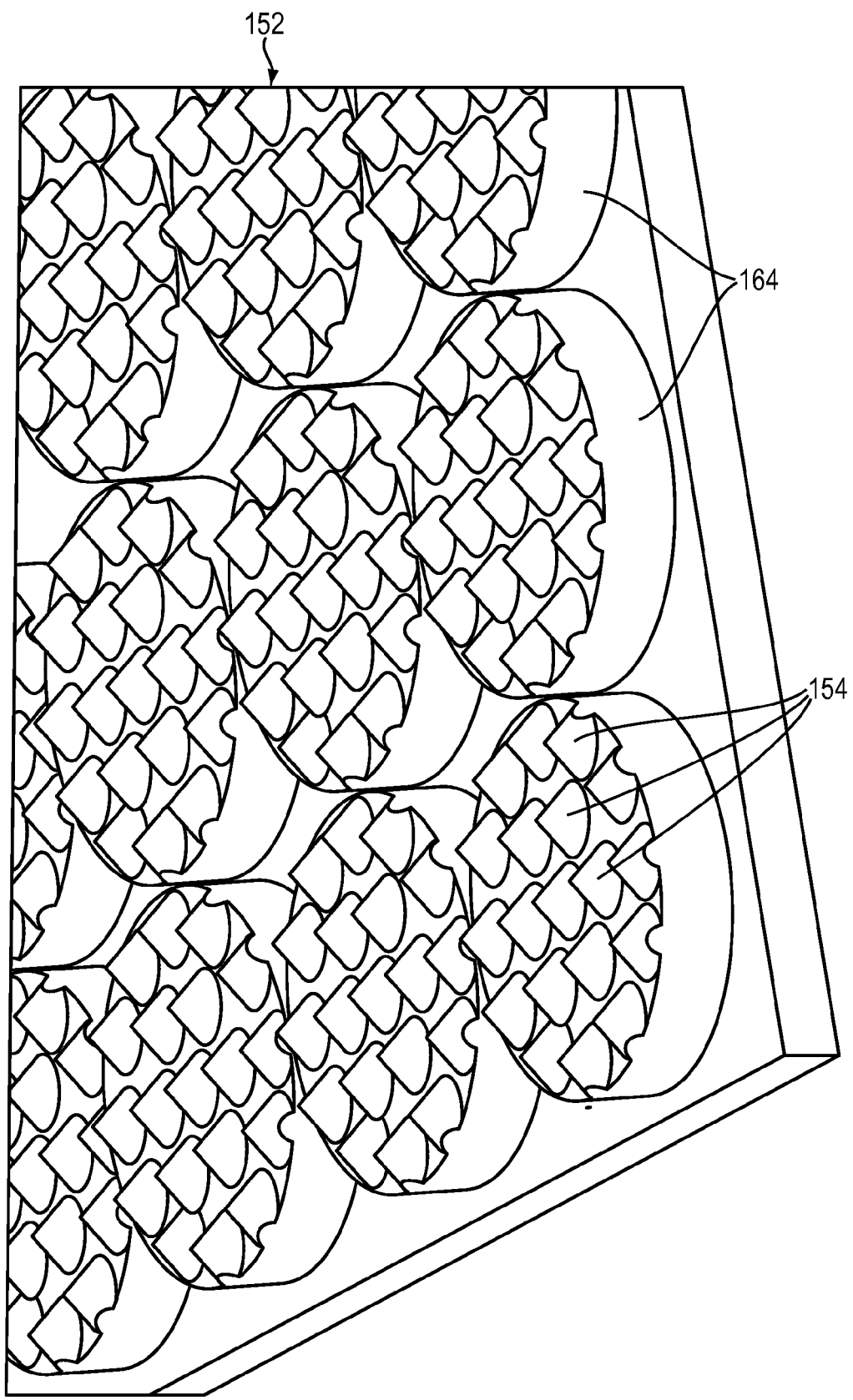
FIG. 18 shows a schematic illustration of an enlarged portion of an external surface of an acetabular cup according to one embodiment of the present invention.

FIG. 18 shows a section of a particular truncated-bead lattice 152 similar to that shown in FIG. 17. Thus, it can be seen that each bead 164 is truncated so as to provide a large top surface layer onto which a plurality of conical micro-spikes 154 are provided. Notably, each bead 164 is arranged to touch its nearest neighbours so that forces applied to the beads 164 can be distributed through the lattice 152. The spaces between the beads 164 form a porous structure for bone in-growth and the rounded sides of the beads 164 provide undercuts which allow bone to grow into to thereby lock onto the cup 150 in time.

Figure 19:
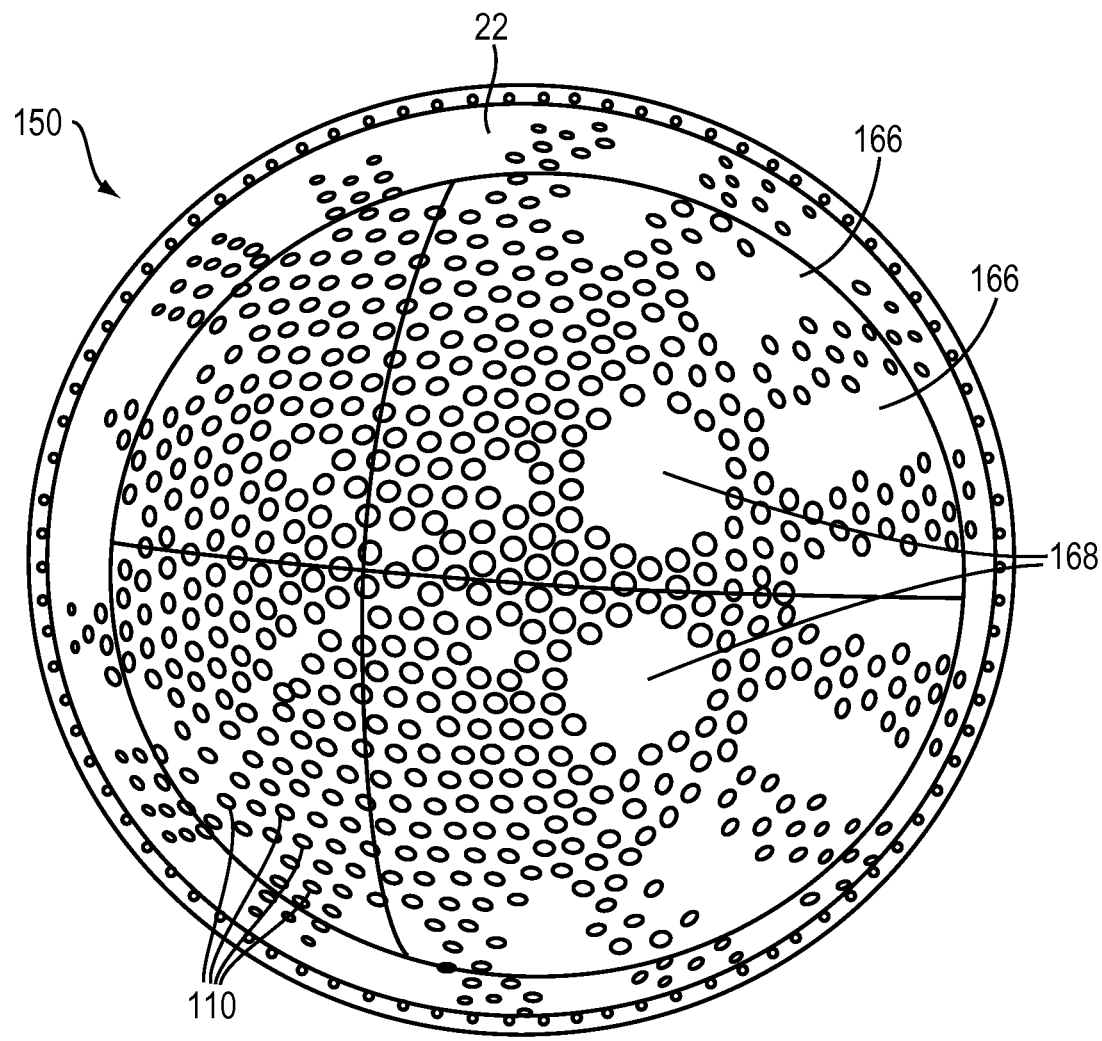
FIG. 19 shows an internal view of a metal shell of an acetabular cup prosthesis according to an embodiment of the present invention, showing the distribution of cut-outs for mechanical attachment of a polymer inner liner.

FIG. 19 shows an internal view of the metal shell 22 of the cup 150. This shows the distribution of the spherical undercuts 110 provided in the metal shell 22 for attachment of the polymer liner 24. Thus, it can be seen that the undercuts 110 are smallest around the periphery of the cup 150 where the metal shell 22 is at its thinnest, becoming thicker towards the centre of the cup 150 where the metal shell 22 is thickest. In addition, no undercuts 110 are provided in the areas 166 opposite the strengthening ribs 162 in order to preserve the strength of the metal in these regions. Furthermore, no undercuts 110 are provided in the areas 168 opposite to the location of the modular pegs 158. The reason for this will become apparent in the discussion of later figures.

Figure 20:
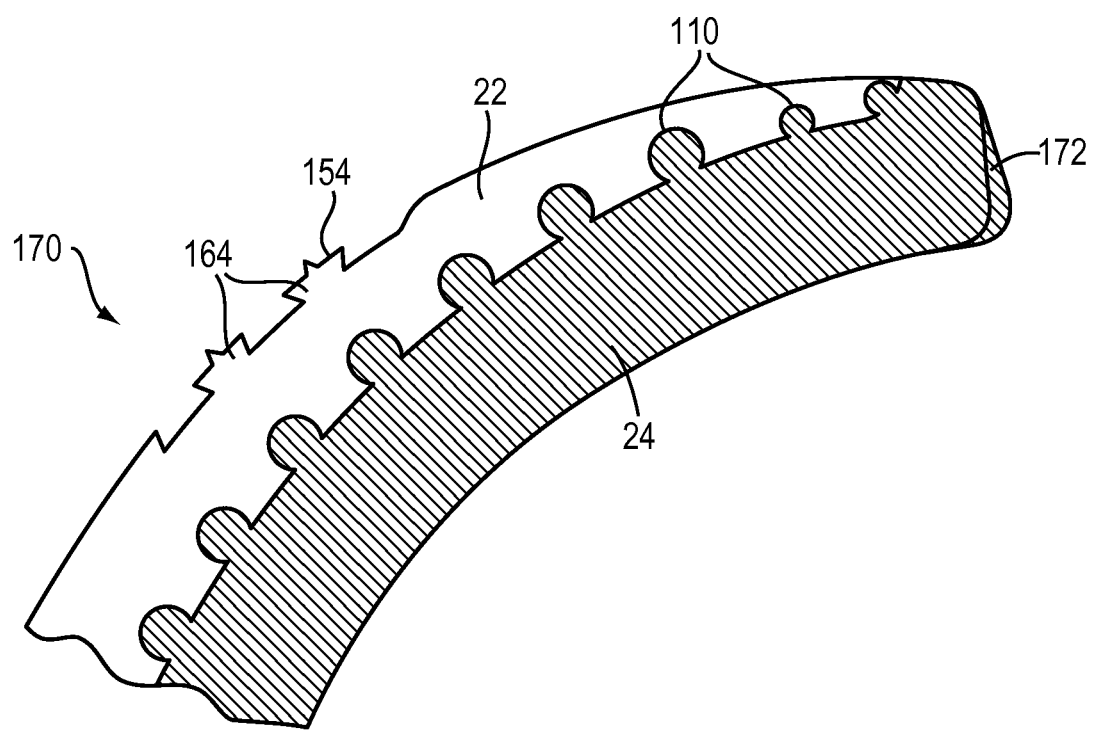
FIG. 20 shows a part cross-sectional view of an edge portion of an acetabular cup prosthesis according to an embodiment of the present invention, showing the mechanical attachment of a polymer inner liner in spherical cut-outs provided on an internal surface of a metal outer shell, and wherein the metal outer shell comprises a plurality of truncated beads on its external surface.

FIG. 20 shows a simplified schematic view of a part cross-sectional view of a supero-lateral edge portion of an acetabular cup prosthesis 170 according to a further embodiment of the present invention, which is similar to that shown in FIG. 17. In this case the metal shell 22 gradually increases in thickness towards its centre while the polymer liner 24 has its maximum thickness at this side of the cup 170 and decreases in thickness towards the inferior side of the cup 1 70 (not shown). Spherical undercuts 110 are provided in the inner surface of the metal shell 22 into which the polymer liner 24 is compression moulded so as to mechanically attach the components together. As described above, the undercuts 1 10 are smallest at the edge of the metal shell 22 and become larger as the metal shell 22 increases in thickness. It will also be noted from FIG. 20 that the polymer liner 24 is provided as an extension from the end of the metal shell 22 and that the edge 172 of the polymer liner 24 is sloped outwardly so as to maximise the articular surface area which would otherwise be reduced by the displacement of the inner liner 24 with respect to the metal shell 22.

A plurality of truncated beads 164 including micro-spikes 154 are provided on the outer surface of the metal shell 22 as described above. Note the beads 164 shown in FIG. 20 are illustrative only. In practice a great many beads 164 would be provided in touching relationship so as to form a lattice.

Figure 21:
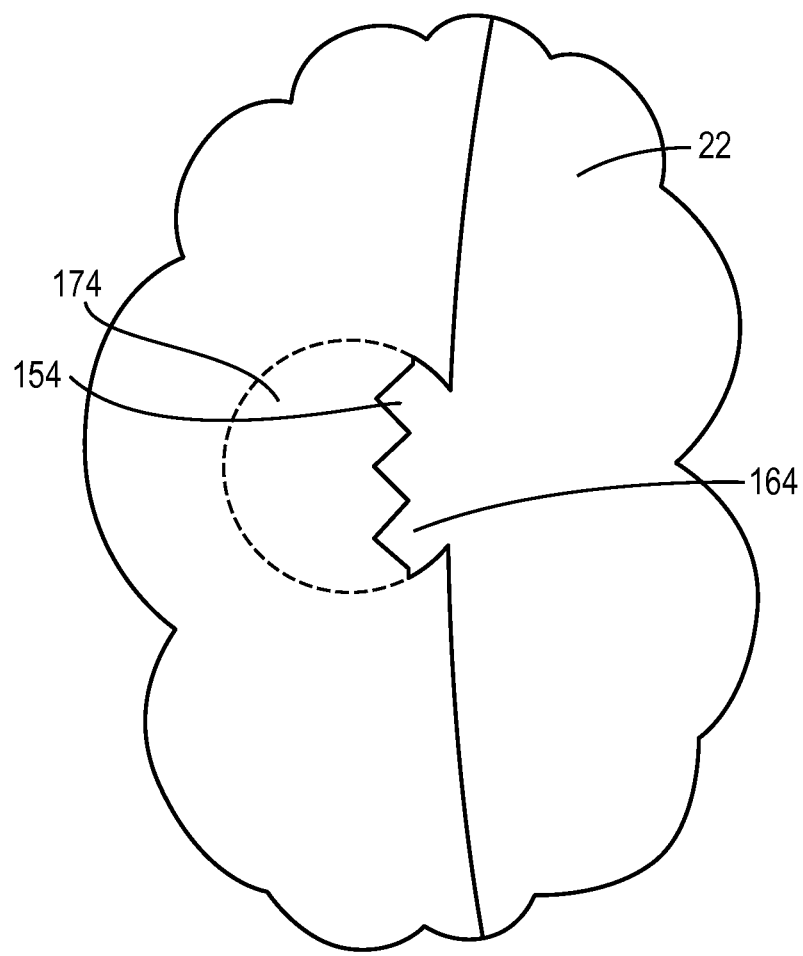
FIG. 21 shows an enlarged view of a truncated bead provided on the acetabular cup of FIG. 20.

An enlarged view of a truncated bead 164 is shown in FIG. 21 along with a dashed spherical outline of the bead 164 prior to its truncation.

Figure 22:
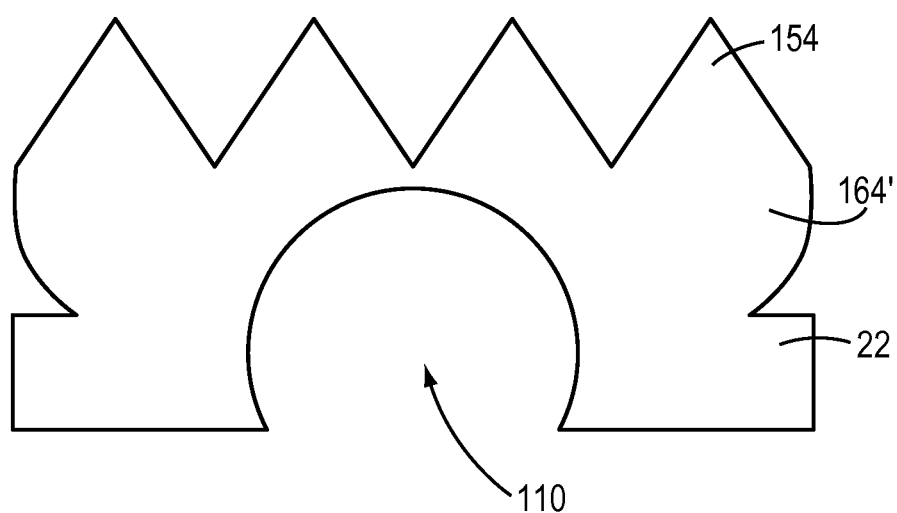
FIG. 22 illustrates schematically a truncated bead having a spherical cut-out protruding into it from an inner surface thereof, in accordance with a particular embodiment of the invention.

FIG. 22 illustrates schematically another truncated bead 164' having a spherical cut-out 110 protruding into it from an inner surface of the metal shell 22 in accordance with another embodiment of the invention.

Figure 23:
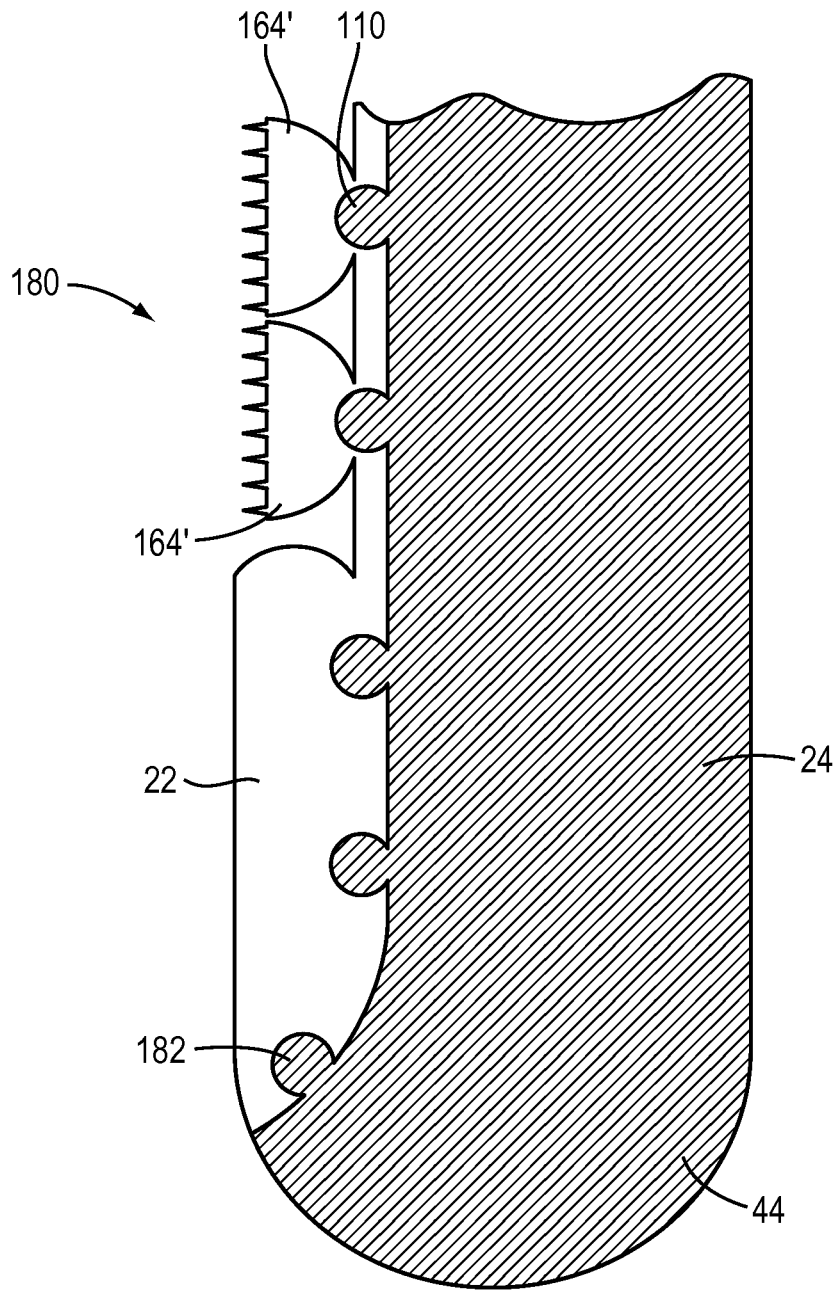
FIG. 23 shows a part cross-sectional view of an edge portion of an acetabular cup prosthesis according to a particular embodiment of the present invention, showing the mechanical attachment of a polymer inner liner in spherical cut-outs provided on an internal surface of a metal outer shell, and wherein the metal outer shell comprises a plurality of truncated beads on its external surface and into which the spherical cut-outs protrude, however, as the section is not through the mid-point of the beads, they appear not to be touching in this view.

FIG. 23 shows another part cross-sectional view of a supero-lateral edge portion of an acetabular cup prosthesis 180 according to a further embodiment of the present invention. In this case beads 164' similar to that shown in FIG. 22 are provided into which the spherical cut-outs 110 in the metal shell 22 protrude. Thus, the polymer liner 24 is mechanically attached to the metal shell 22 by polymer nodules 182 located within the spherical cut-outs 110. In this embodiment the edge 44 of the polymer liner 24 is rounded.

Figure 24A:
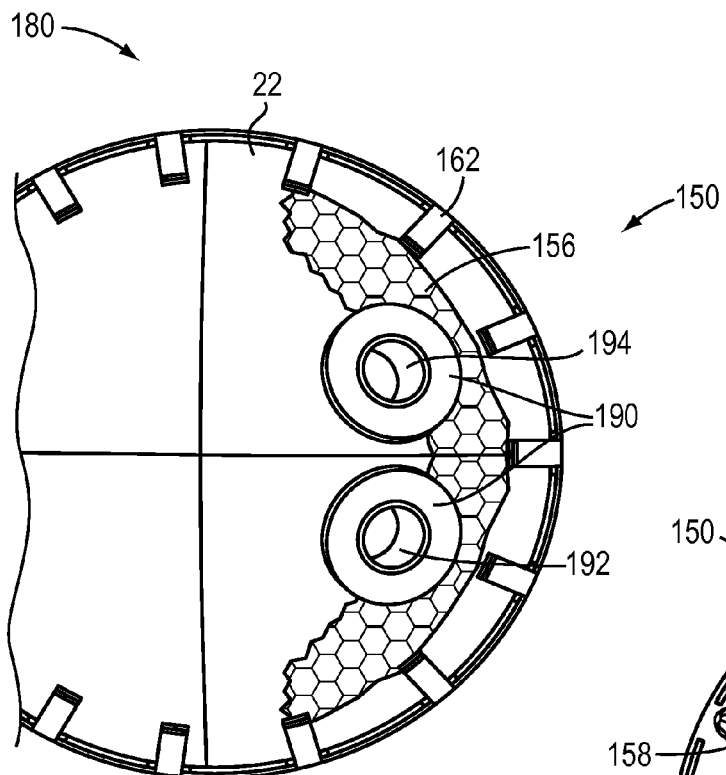
FIG. 24A shows a part underneath plan view of an external surface of a metal shell for the acetabular cup of FIG. 17 including fixation means for modular pegs and fixation spikes for primary fixation to the bony bed but prior to inclusion of truncated beads.

FIGS. 24A, B and C show part underneath plan views of the external surface of the metal shell 22 for the acetabular cup 150 of FIG. 17 including fixation means 190 for the modular pegs 158 and the fixation spikes 156 for primary fixation to the bony bed but prior to inclusion of the truncated-bead lattice 152. From each of these views, the band of fixation spikes 156 appears to form a horseshoe shape with the modular pegs 158 encapsulated by the horseshoe. As described above, the fixation spikes 156 are provided in lieu of fixation normally obtained in thick-walled cups from heavy press-fit (e.g. by the acetabulum being under-reamed by 2 mm when compared to the cup outer diameter). In embodiments of the present invention, where thin-walled cups are provided, the reaming will preferably be a line-to-line fit with the cup outer diameter or, at most, a 1 mm press-fit may be applied. In either case, the fixation spikes 156 are arranged to project beyond the cup outer diameter so that they are necessarily driven into the reamed surface of the acetabulum on cup impaction. As viewed in FIGS. 24A, B and C, the fixation spikes 156 are all in line with an axis through the centre of the cup 150 and passing midway between the modular pegs 158.

The fixing means 190 for the modular pegs 158 each comprise a relatively thick metal support ring including a blind hole 192 provided with an internal screw thread 194. Although not shown it will be understood that the underside of each modular peg 158 has a projection provided with an external screw thread for complementary engagement with the screw thread 194. The fixation means 190 is a permanent feature of the metal shell 22 and may be formed integrally therewith.

If the surgeon decides that additional fixation is not necessary, the modular pegs 158 will not be used and, instead, the holes 192 in the fixation means 190 will be provided with fillings 196. The fillings 196 include an external thread so they can be screwed into the fixation means 190 and a hexagonal cut-out 198 for location of an Allen key so they can be selectively removed (e.g. for the attachment of a modular peg 158).

Figure 24C:
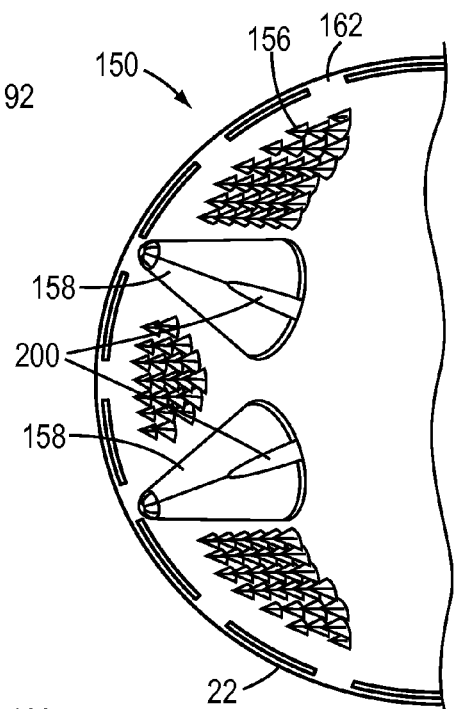
FIG. 24C shows a view similar to that of FIG. 24A, rotated through 180°, and showing the modular pegs fitted in the fixation means.
Figure 24B:
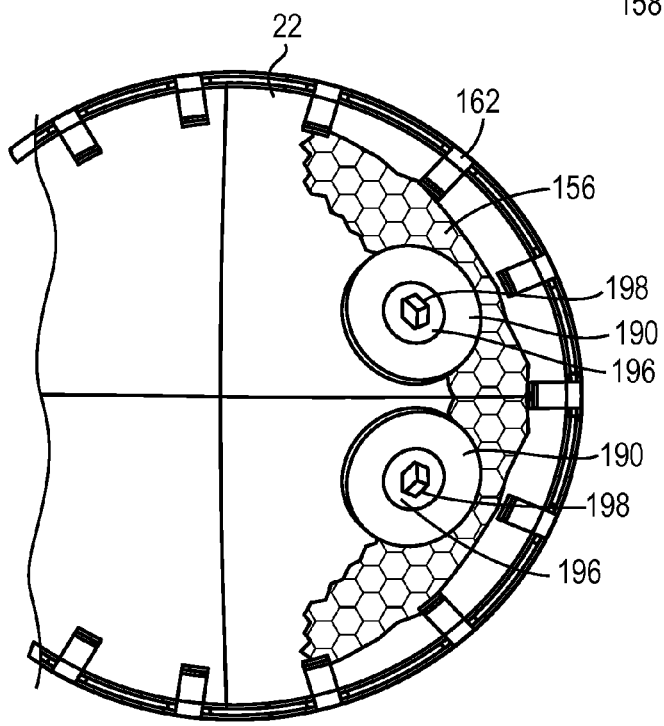
FIG. 24B shows a view similar to that shown in FIG. 24A but with fillings provided in the fixing means.

FIG. 24C shows the two modular pegs 158 screwed into the fixation means of FIG. 24A. The modular pegs 158 shown in FIG. 24C are largely as described in relation to FIG. 17. However, in the particular embodiment shown in FIG. 24C the modular pegs 158 include four equally spaced recesses 200 for ease of grip when screwing or unscrewing the modular pegs 158 to/from the fixation means 190.

FIGS. 25A through D show further views of the configuration shown in FIG. 24C but wherein the recesses 200 are omitted clarity. More specifically, FIG. 25A is a view from the inferior side of the cup 150 and shows that each fixation spike 156 points parallel to the inferior-superior axis of the cup 150 while each modular peg 158 points normal to the exterior surface of the metal shell 22. As described above, FIG. 25B shows that the fixation spikes 156 are all in line with an axis through the centre of the cup 150 and passing midway between the modular pegs 158. FIG. 25C shows further alignment of the fixation spikes 156. FIG. 25D is a side view of the cup 150 showing that the fixation spikes 156 are parallel to the long axis of the modular pegs 158. It is also evident from FIG. 25D that both the fixation spikes 156 and the modular pegs 158 point parallel to the axis of insertion of the cup into the bone. Furthermore, FIG. 25D shows that the width of the rim 160 around the periphery of the metal shell 22 is relatively narrow (only 1.5-2 mm thick) at the inferior side 202 of the cup 150 and relatively wide (3-4 mm) around the supero-lateral side 204 of the cup 150. This additional rim width is advantageous for support since it is common to have no bone covering the supero-lateral side 204 of the cup 150.

Figure 26:
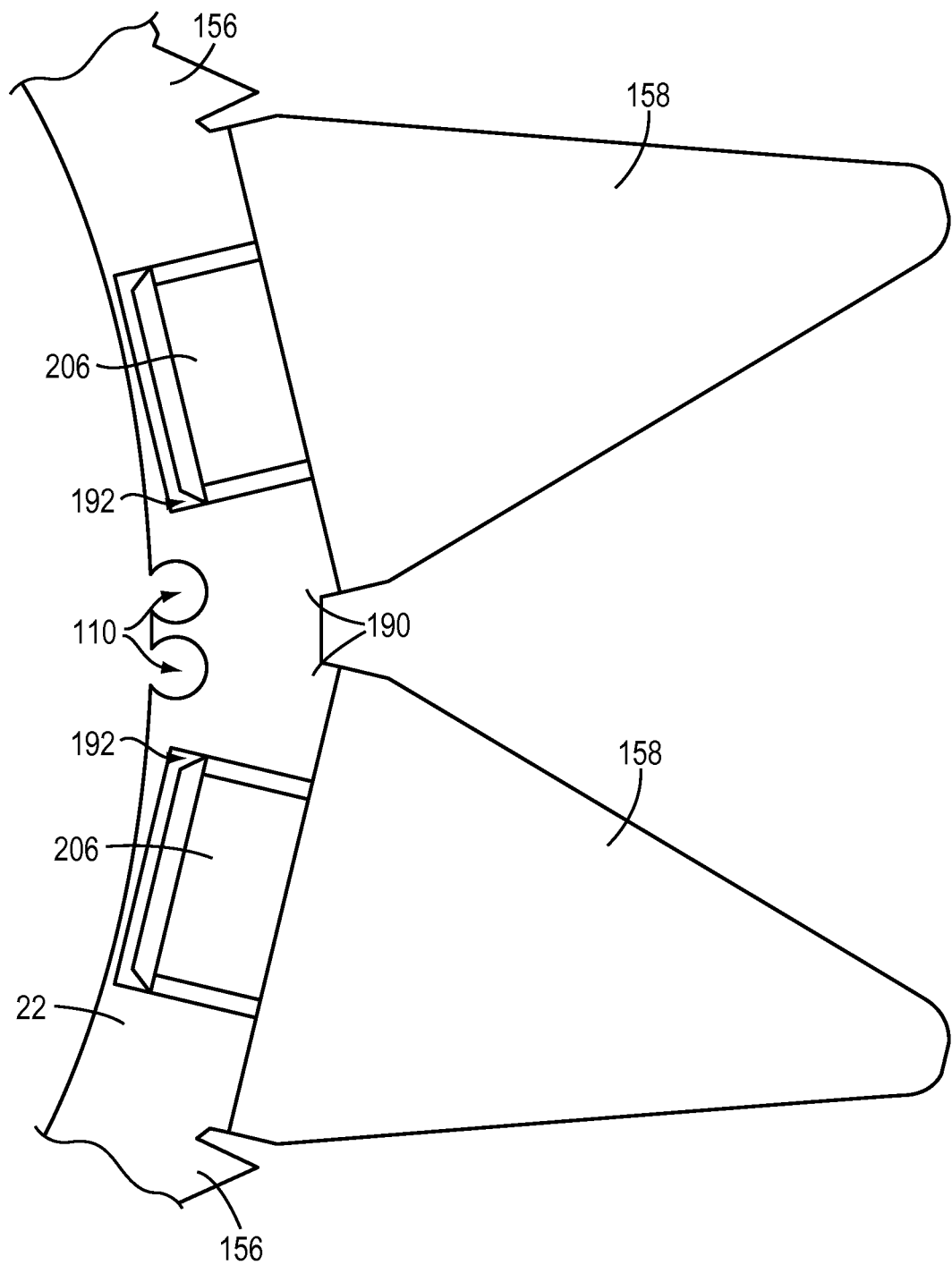
FIG. 26 shows a part cross-sectional view through the modular pegs of FIG. 24C.

FIG. 26 shows a part cross-sectional view through the modular pegs 158 of FIG. 24C. Accordingly, it can be seen that the hole 192 in the fixing means 190 extends through the majority of the thickness of the metal shell 22 (which is at its thickest in this region opposite the wear zone) but terminates without penetrating all the way through. This therefore protects the polymer liner 24 (not shown) adjacent to the fixing means 190. As shown, each modular peg 158 includes a projection 206 provided with an external screw thread for mating with the internal screw thread 194 of the fixing means 190. It is also clear from FIG. 26 that no spherical undercuts 110 (for polymer attachment) are provided in the metal shell 22 directly opposite to the fixing means 190.

Figure 27:
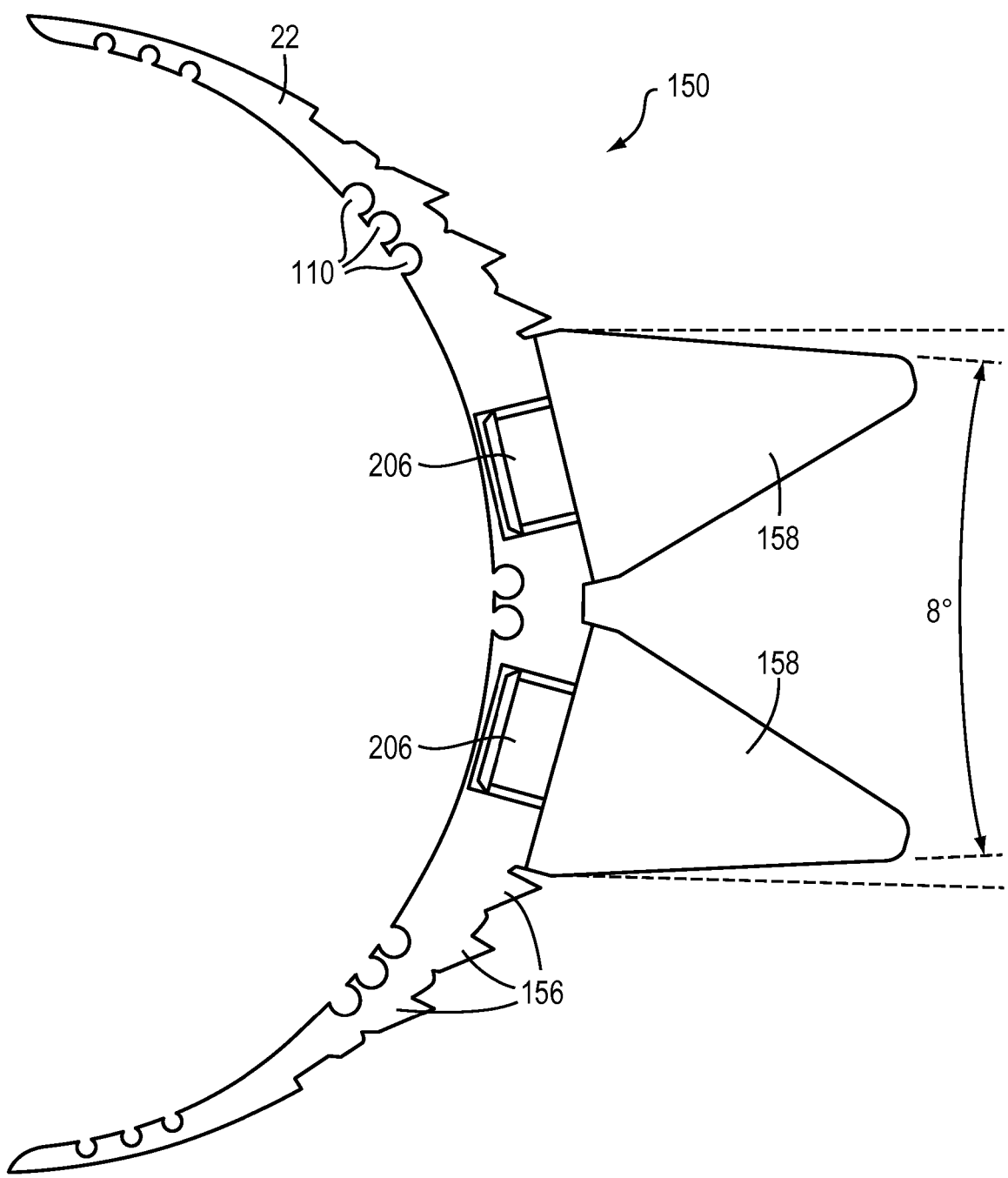
FIG. 27 shows a cross-sectional view similar to that shown in FIG. 26 but showing the entire metal shell of the acetabular cup, including internal cut-outs for polymer attachment.

FIG. 27 shows a cross-sectional view similar to that shown in FIG. 26 but showing the entire metal shell 22 of the acetabular cup 150, including several of the spherical cut-outs 110 for polymer attachment (arranged for illustrative purposes only). This figure clearly shows the thickness of the metal shell 22 being greatest in the centre of the cup 150 and getting thinner towards the periphery of the cup 150. FIG. 27 also shows that the long axis of each modular peg 158 diverges with respect to the other. This arrangement has been chosen partly because it is desirable not to increase the thickness of the cup to make the pegs parallel and partly because diverging pegs provide good fixation in the bone. However, it will be understood that if the diverging peg were cylindrical it would not be possible to insert them securely into the bone (since this would require an undercut). However, with conical pegs 158, as shown, it is possible to insert the cup in a straight line, without requiring an undercut. In the present embodiment, the conical pegs 158 are disposed such that although they have diverging long axes, each outermost conical side is angled inwardly by 4 degrees from parallel.

In another embodiment of the present invention (not shown) a prosthetic cup may be provided with a truncated-bead lattice 152 as described above and shown in FIG. 17, but without any fixation means or modular pegs. In this case an array of fixation spikes 156 as described above are also provided but in this case the spikes in the array vary in height and are smallest towards the edge of the array and gradually increase in height to the largest in the centre of the array. The array in this embodiment is generally of a circular disc shape which is located opposite to the intended wear zone (i.e. in the supero-lateral half of the cup). Furthermore, in this embodiment, the internal surface of the metal shell is provided with spherical cut-outs 110, as described above, but in this case the spherical cut-outs are all of a similar size and are evenly distributed in a ring around the edge of the metal shell and over the majority of the rest of the metal shell but are not provided in the region opposite to the rim of the shell or in the region opposite the array of fixation spikes. These regions are provided free of cut-outs for increased strength in these areas.

Alternative lattice structures to the truncated-bead lattice 152 described above, are envisaged in accordance with embodiments of the invention. FIGS. 28A through 29E are illustrative of one such lattice structure 230 which could be provided on an external surface of a metal shell of a prosthesis such as an acetabular cup. As before, the lattice 230 is configured to provide the surface with a rough exterior to aid initial fixation, a porous structure for bone in-growth and a plurality of undercuts to allow bone to lock onto the surface.

Figure 28A:
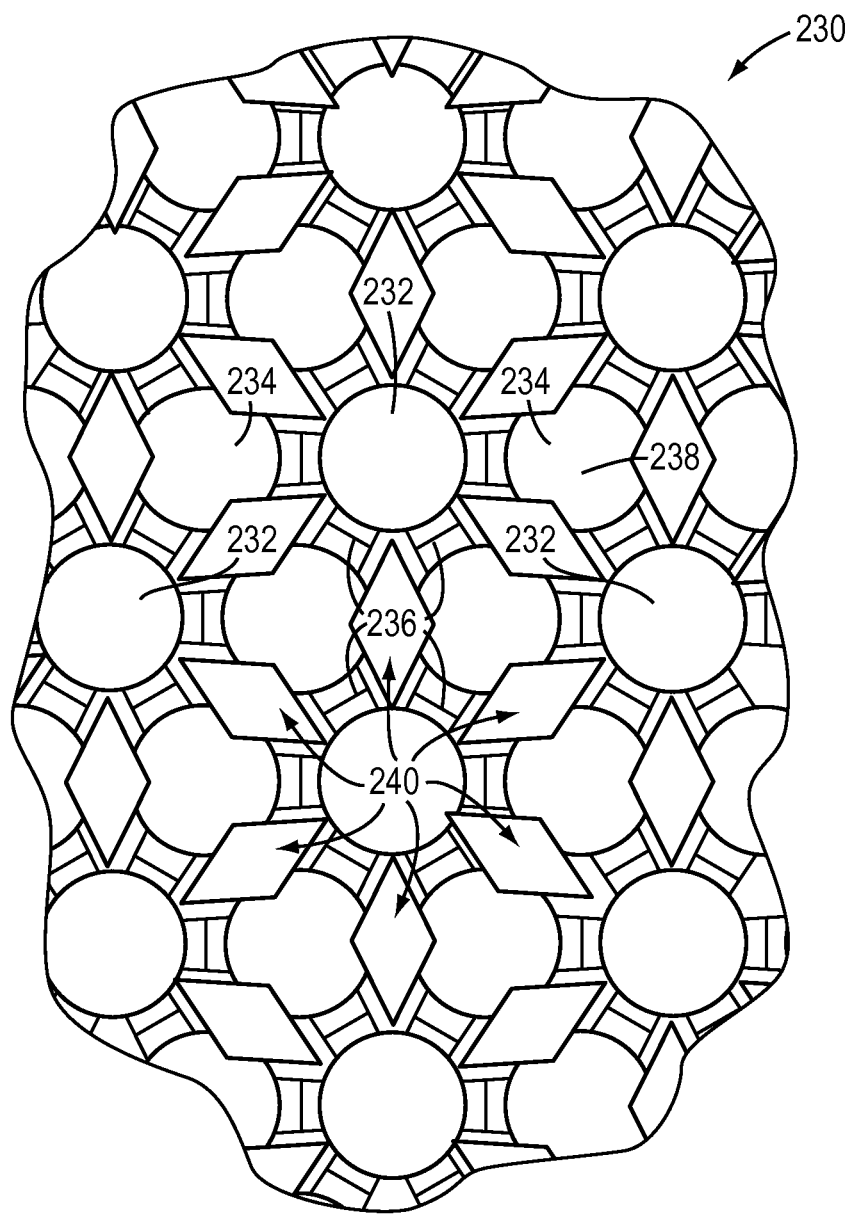
FIG. 28A shows an enlarged underneath plan view of a porous lattice structure for attachment to an external surface of a prosthesis such as an acetabular cup prosthesis according to an embodiment of the present invention.
Figure 28B:
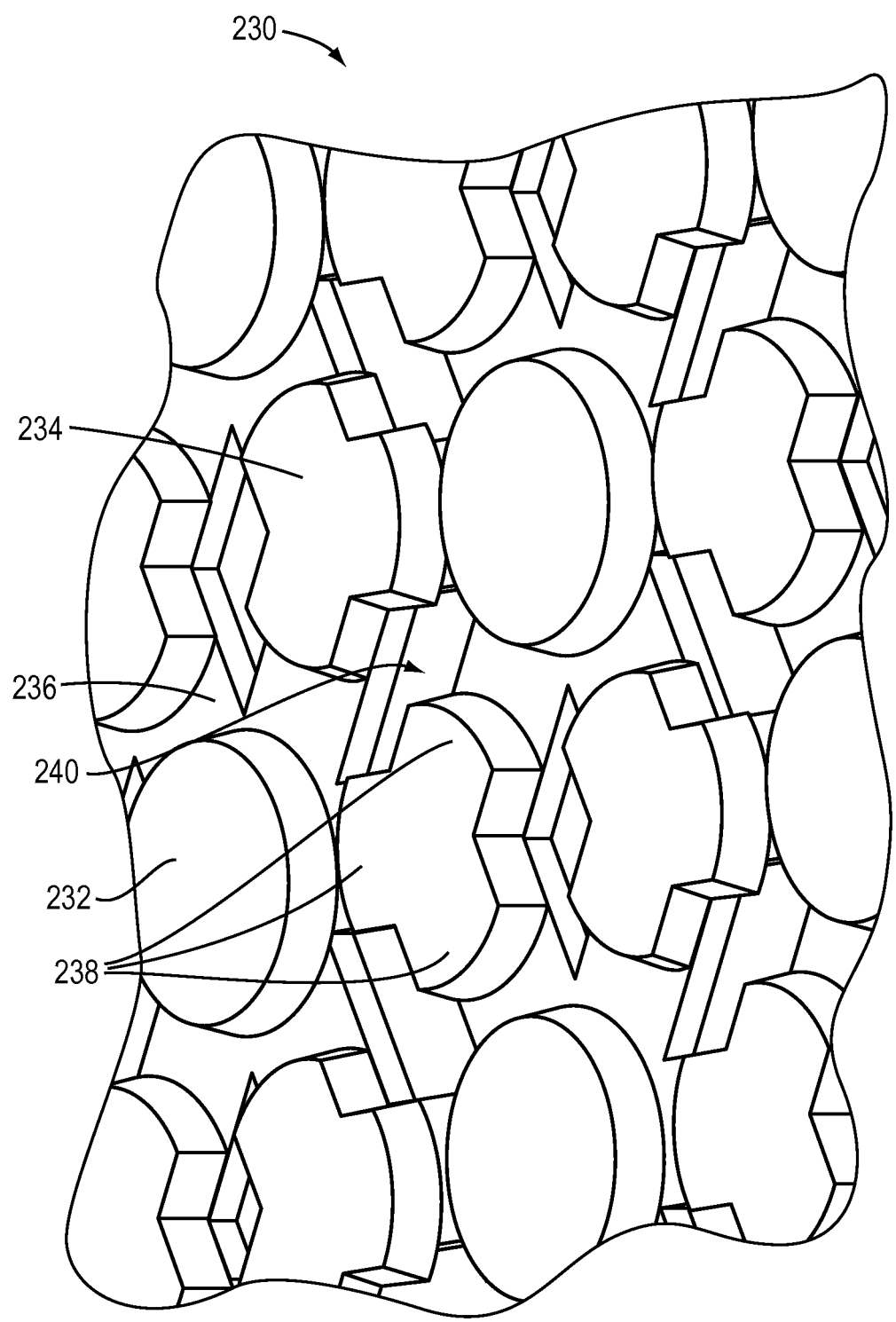
FIG. 28B shows a further enlarged perspective view of a portion of the lattice structure shown in FIG. 28A.
Figure 29A:
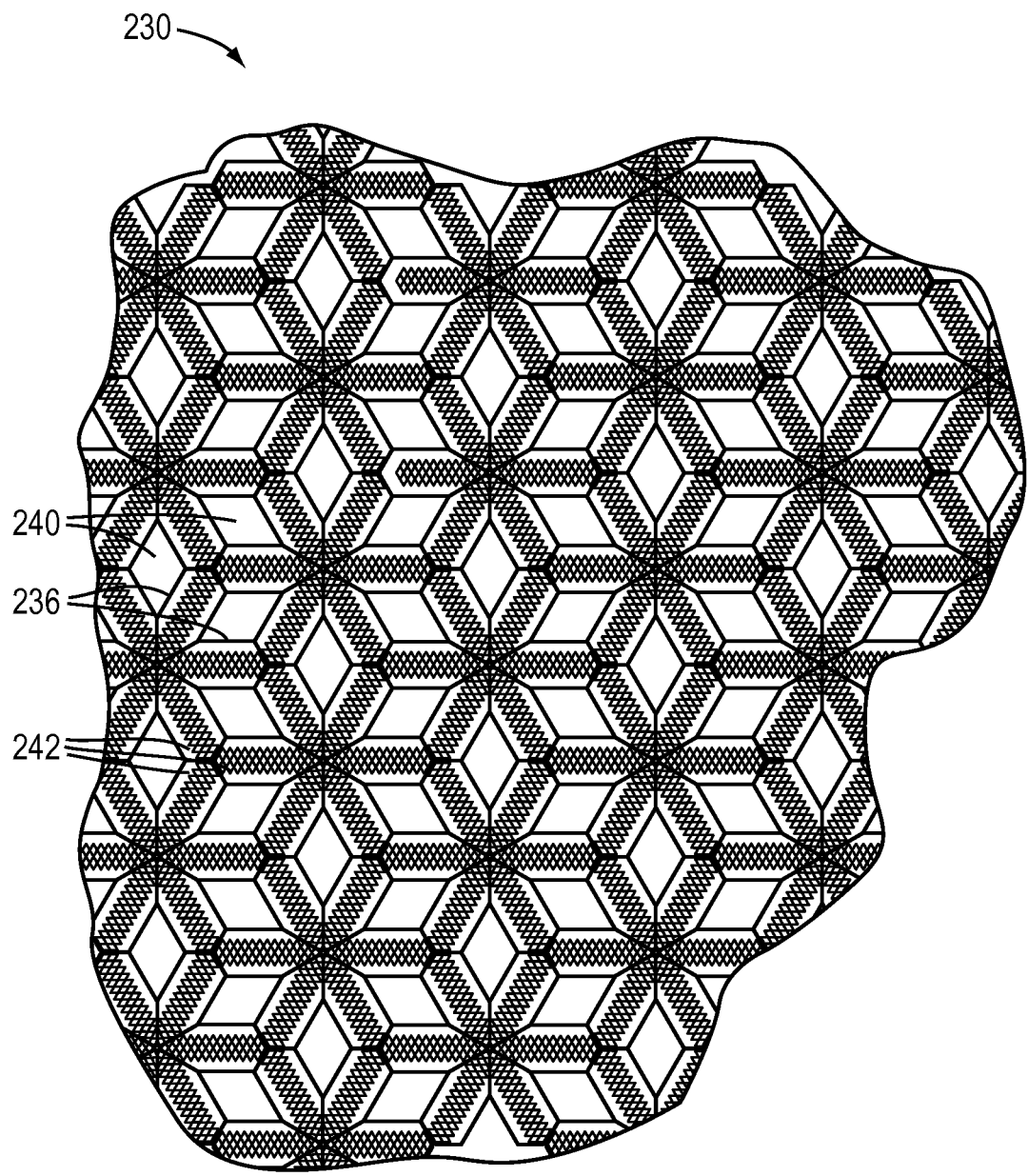
FIG. 29A shows a top plan view of the lattice structure shown in FIG. 28A.
Figure 29B:
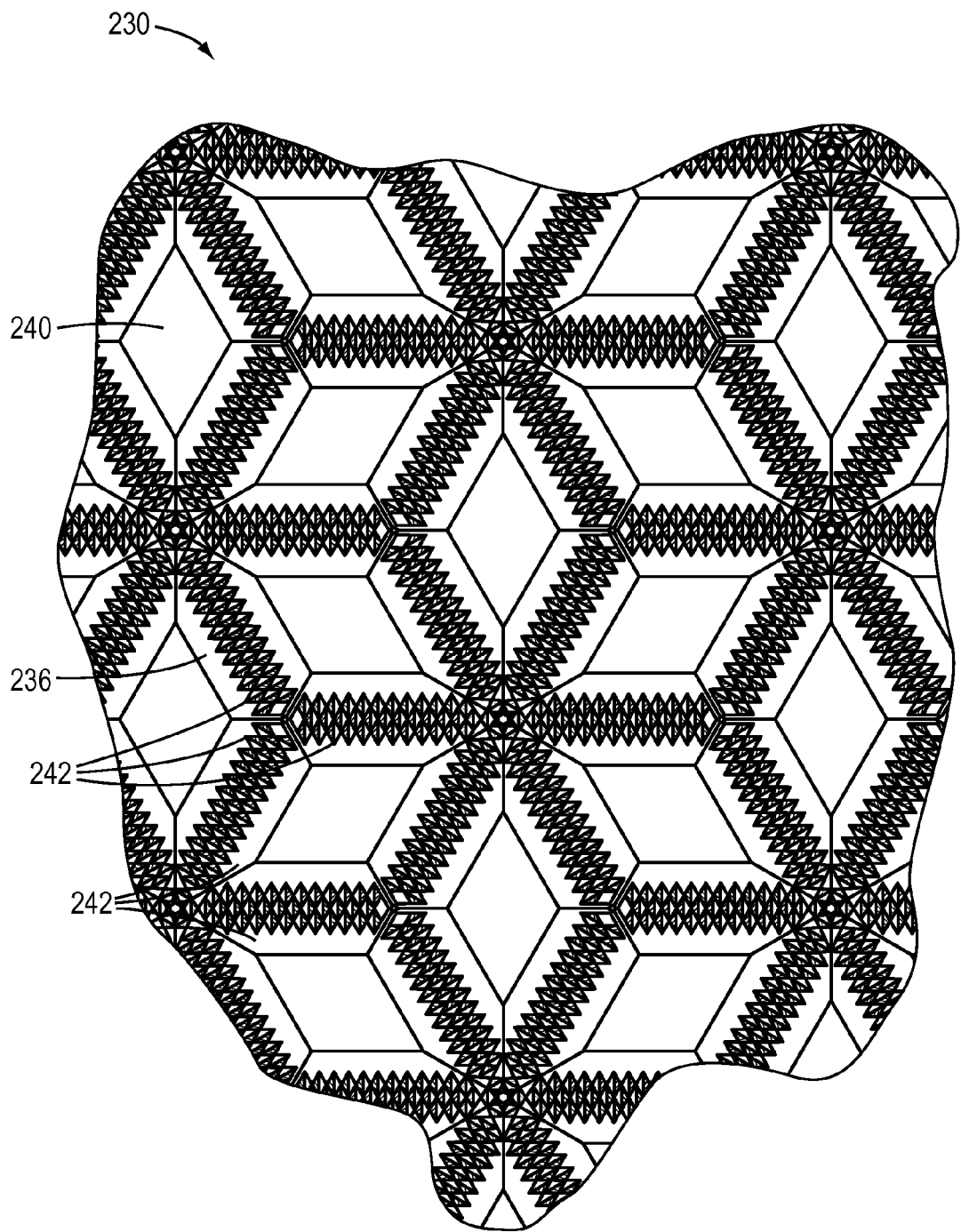
FIG. 29B shows an enlarged top plan view of a portion of the lattice structure shown in FIG. 29A.
Figure 29C:
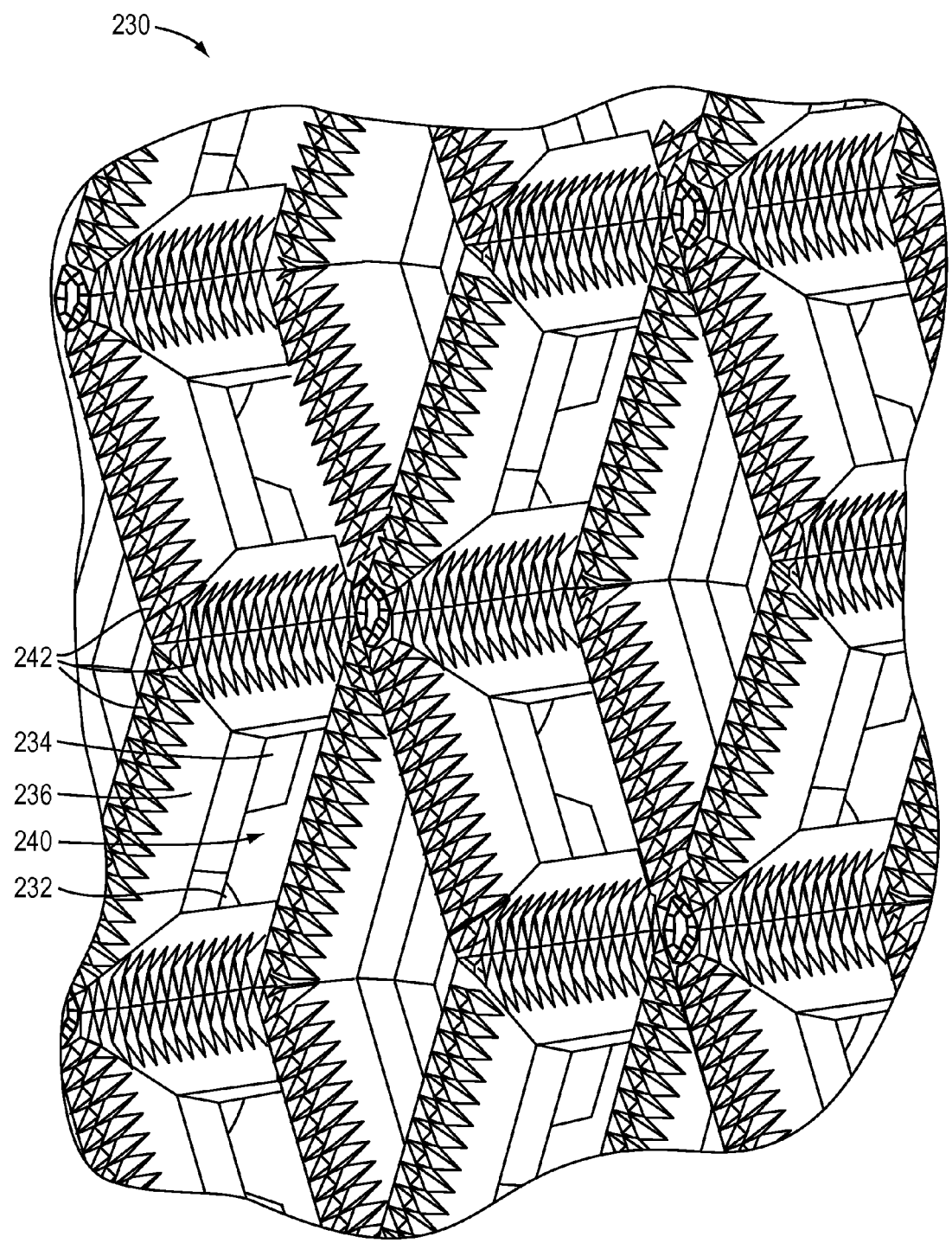
FIG. 29C shows an enlarged perspective view of a portion of the lattice structure shown in FIG. 29B.
Figure 29D:
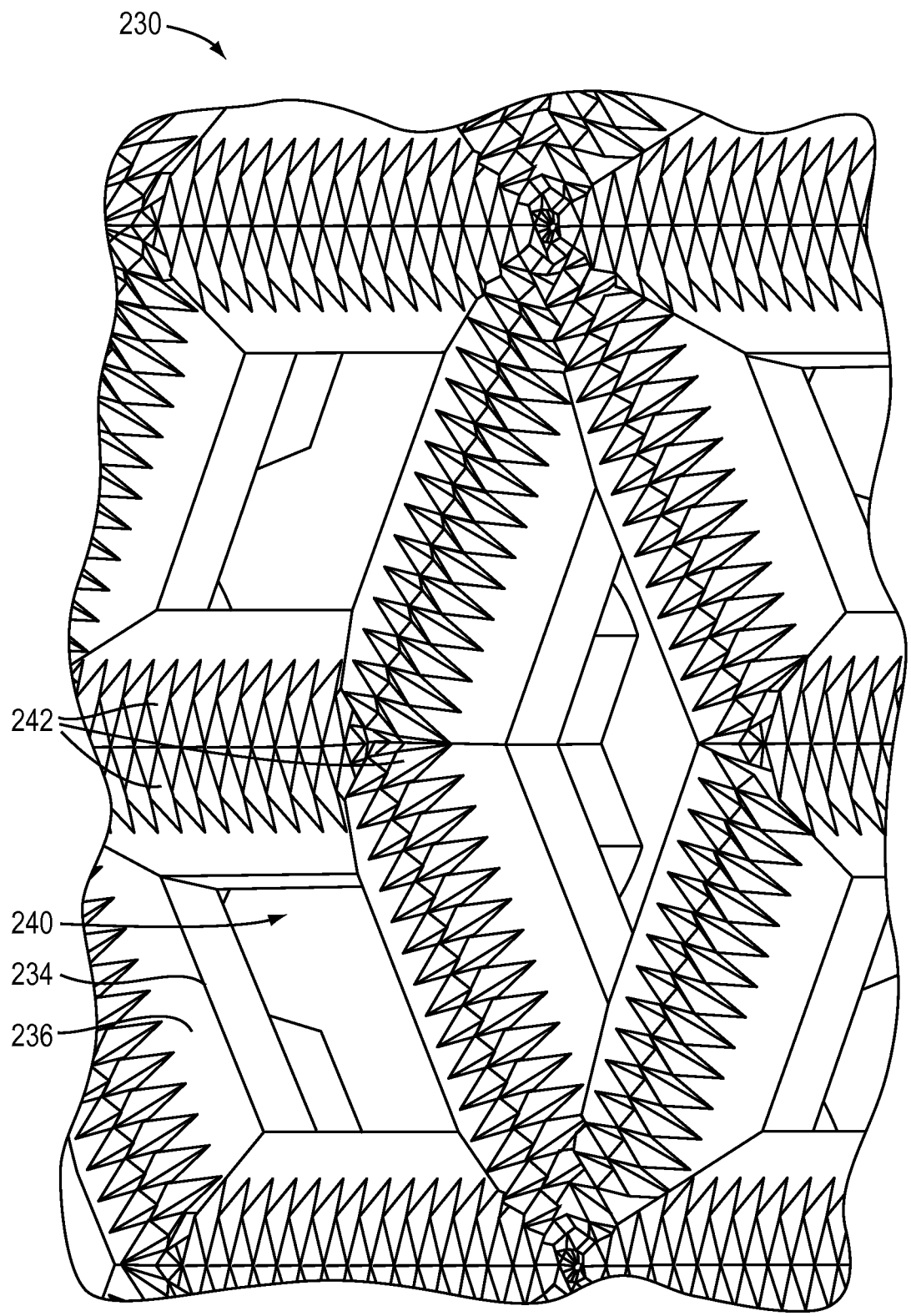
FIG. 29D shows a further enlarged perspective view of a first portion of the lattice structure shown in FIG. 29C.
Figure 29E:
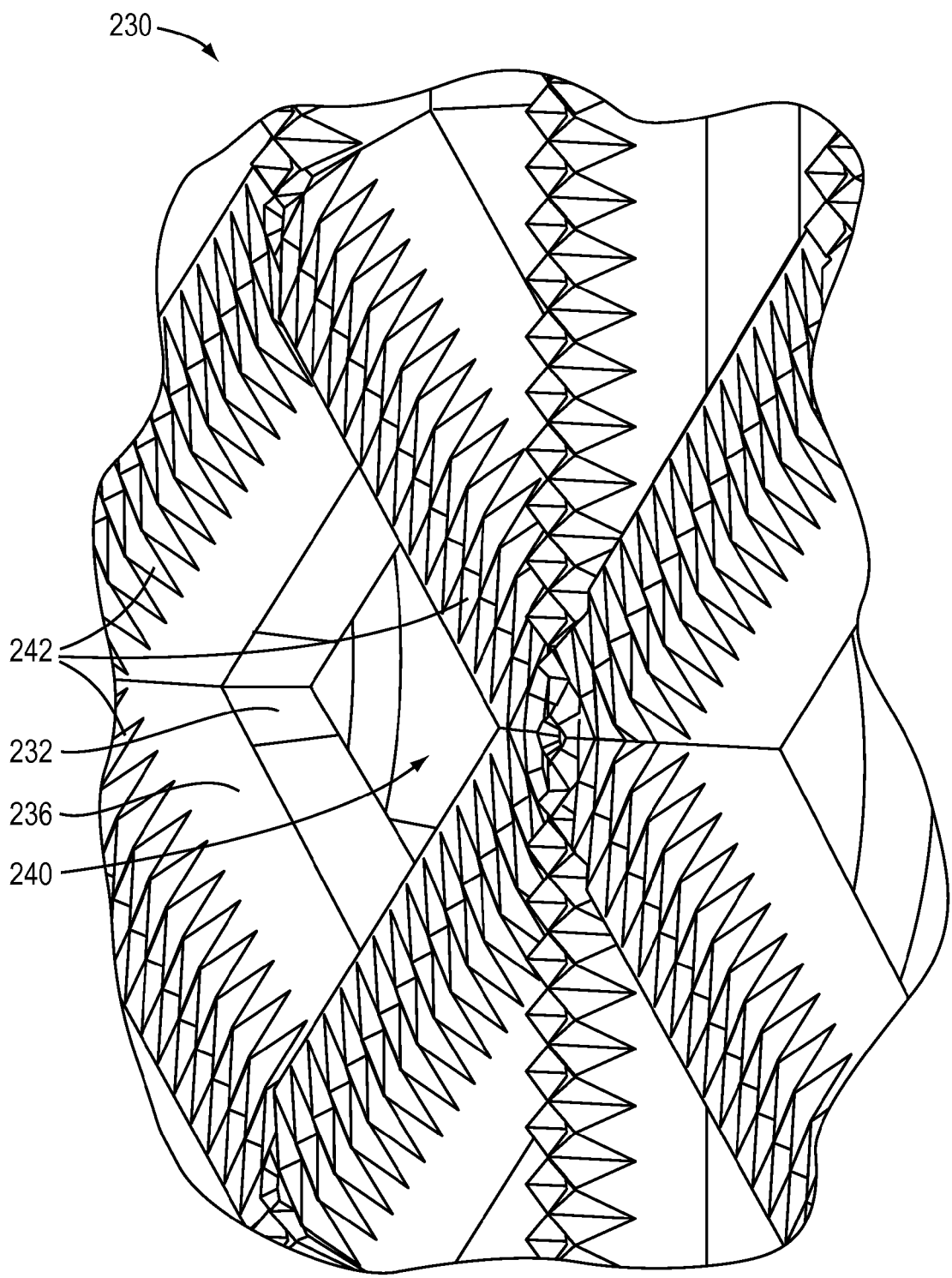
FIG. 29E shows a further enlarged perspective view of a second portion of the lattice structure shown in FIG. 29C.

More specifically, FIGS. 28A and B show an enlarged underneath view of the lattice 230. The lattice 230 includes a first series of posts 232 that have a circular cross-section and a second series of posts 234 that have a triple-lobed cross-section. When provided on an external surface of a prosthesis the posts 232 and 234 will extend normally of the surface and will support mating ends (not shown) of a number of bridging elements 236. In this embodiment, the circular posts 232 support mating ends of six bridging elements 236. Each bridging element 236 extends radially from a circular post 232 to a lobe 238 of one of the triple-lobed posts 234. Each of the triple-lobed posts 234 is arranged to support mating ends of three bridging elements 236, one extending from each of its lobes 238. Accordingly, in this embodiment where each circular post 232 supports six bridging elements 236 and each triple-lobed post 234 supports three bridging elements 236, a tessellating pattern is created with diamond-shaped gaps 240 provided between the bridging elements 236. As best shown in FIG. 2813, the posts 232, 234 and bridging elements 236 are all have a relatively thick cross-section so as to allow for molten metal to easily flow into the structure during manufacture of the lattice 230.

It will be understood that the lattice 230 described above not only allows bone in-growth through the gaps 240 between the bridging elements 236 but also provide undercuts 242 in the regions underneath the bridging elements 236, between the posts 232, 234, into which bone can grow to mechanically lock the implant in place.

FIGS. 29A through 29E show a top plan view of the lattice 230 of FIG. 28A and B. Although the posts 232, 234 are not clearly visible in these views, it will be understood that a circular post 232 is provided wherever six bridging elements 236 meet and a triple-lobed post 234 is provided wherever three bridging elements 236 meet. As shown in these figures, a rough exterior is provided on the lattice 230 by the provision of diamond and pyramid shaped cut-outs 242 in the exterior surface of the bridging elements 236. These cut-outs 242 create a plurality of sharp edges which can be presented to the bone during use to aid primary fixation of the implant.

Figure 30A:
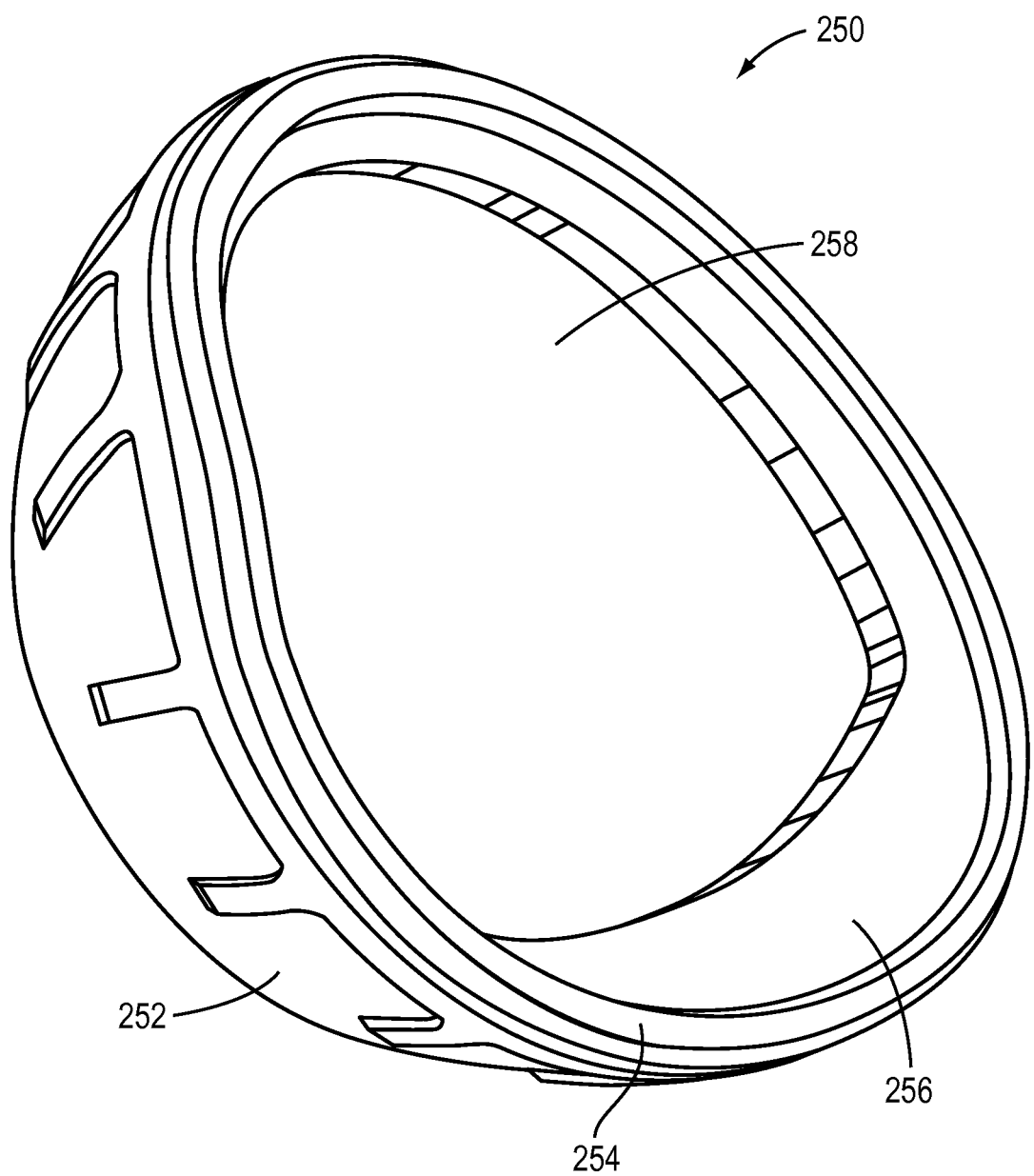
FIG. 30A shows a perspective view of an acetabular cup prosthesis according to an embodiment of the invention, after a first layer of the polymer liner has been moulded but prior to the moulding of a second layer forming a portion of the articular surface layer of the cup.
Figure 30B:
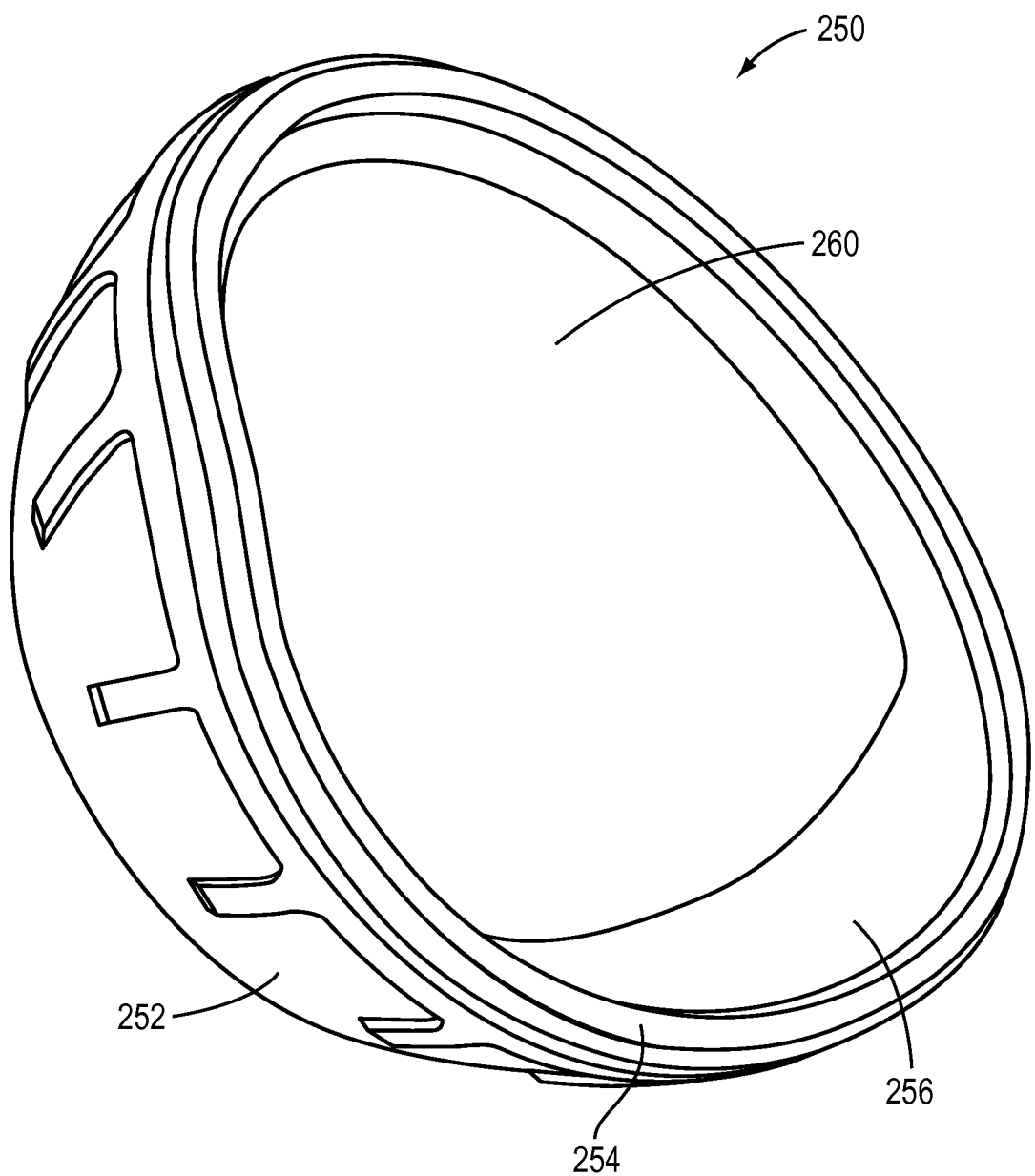
FIG. 30B shows a perspective view of the acetabular cup of FIG. 30A after the moulding of the second layer in the first layer to form a portion of the articular surface layer of the cup.

FIG. 30A shows a perspective view of an acetabular cup prosthesis 250 according to a further embodiment of the invention. The cup 250 comprises a metal outer shell 252 and a polymer inner liner 254. The polymer inner liner 254 includes a first layer 256 which is formed by placing polymer powder including vitamin E into the metal outer shell 252 (which serves as an outer mould cavity) and cold compression stamping the powder into the desired shape of the first layer 256. It will be noted that, in this embodiment, the first layer 256 is formed with a recessed cavity 258 which is configured to receive a second layer 260 of polymer powder as shown in FIG. 30B. Thus, after the moulding of the first layer 256, polymer powder (not including vitamin E) is placed in the cavity 258 and a second mould is employed to cold compress the polymer powder into the second layer 260 forming a portion of the articular surface layer of the cup 250. The first and second layers 256 and 260 are then hot compression moulded to form a single solid cup 250 before it is irradiated to cross-link the molecules in the second layer 260. The cup 250 is then heated to below its melting point to encourage the vitamin E in the first layer 256 to diffuse into the second layer 260 to consume the free radicals therein and thereby minimise the risk of oxidation of the second layer 260. Thus, the cup 250 is formed with a partially cross-linked surface layer 260 in the intended wear zone, which is hoped to increase the wear resistance of the cup 250 during use.

Figure 31:
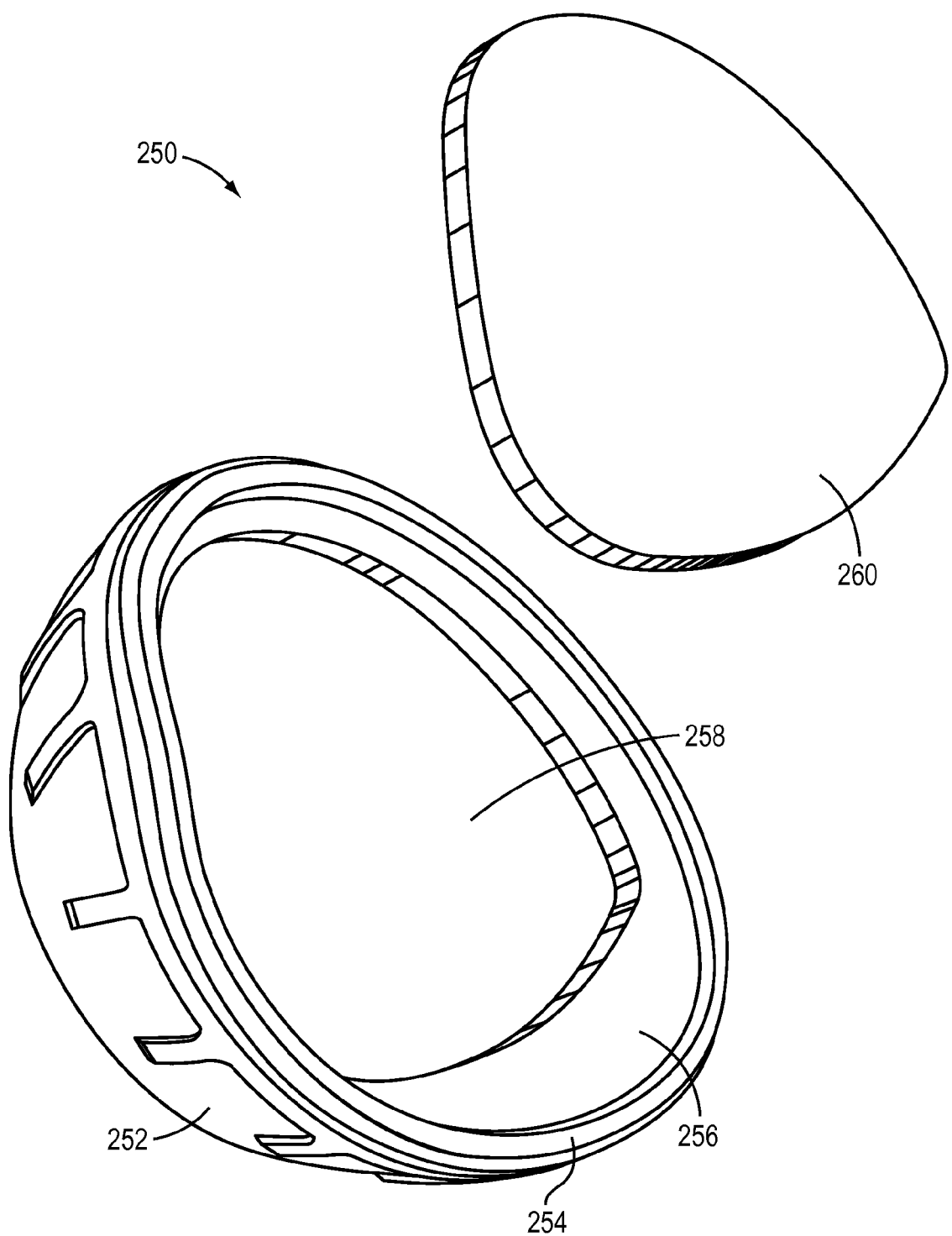
FIG. 31 shows a perspective view of an acetabular cup prosthesis according to a further embodiment of the invention, wherein a second layer of a polymer liner (forming a portion of an articular surface layer of the cup) has been moulded separately to a first layer of the polymer liner, just prior to insertion of the second layer into the first layer.

FIG. 31 shows a perspective view of an acetabular cup prosthesis 260 according to another embodiment of the invention. The cup 260 includes each of the components described above in relation to FIGS. 30A and 30B and so like reference numerals will be employed as appropriate. The only difference between the cup 250 of FIGS. 30A and 30B and the present cup 260 is that, as shown in FIG. 31, the second layer 260 is moulded independently of the cup 260 before being inserted into the recess 258. It will be understood that the step of hot compression moulding the first and second layers 256 and 260 is still performed in this embodiment, along with the subsequent steps described above.

Figure 32:
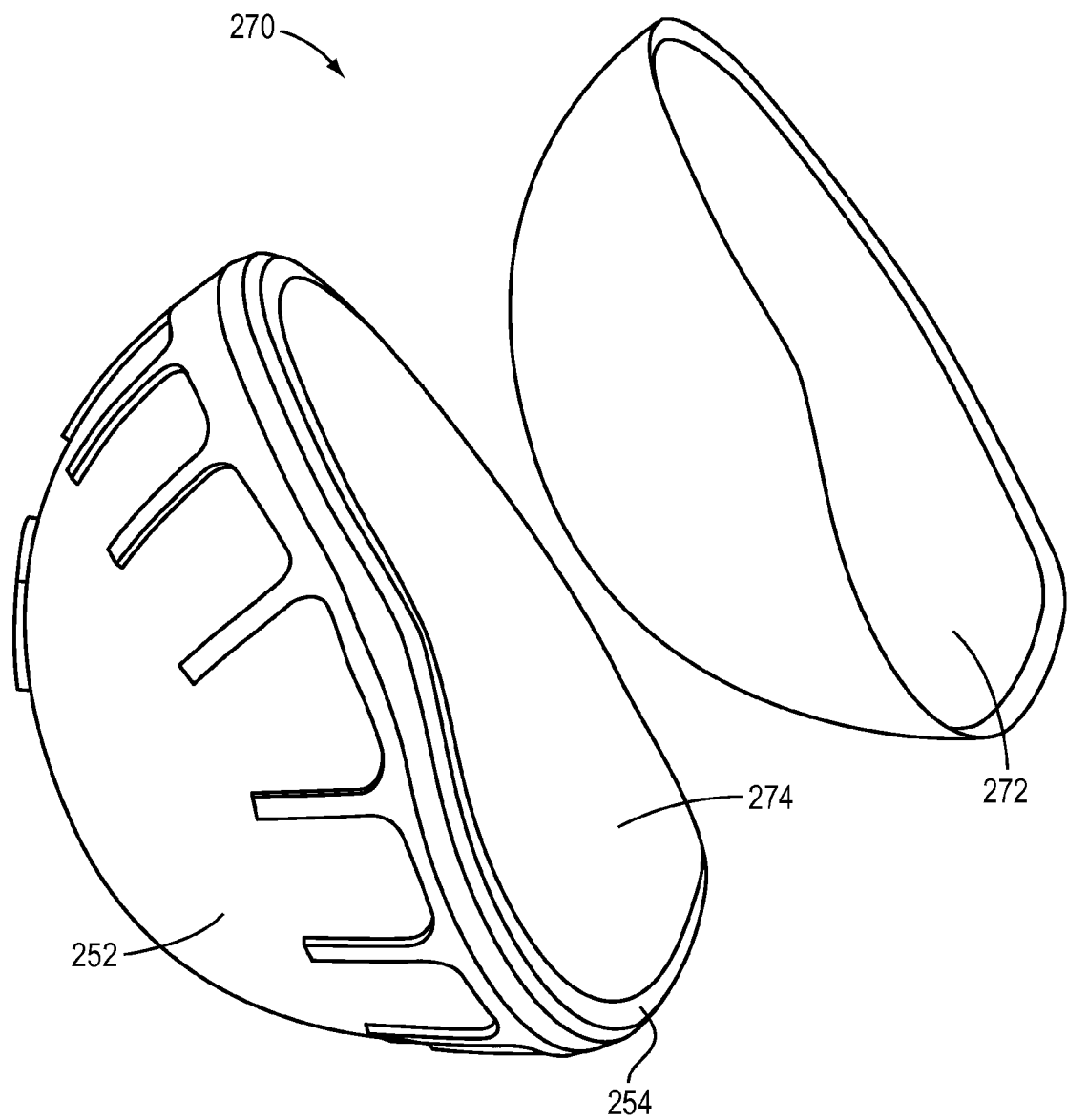
FIG. 32 shows a perspective view of an acetabular cup prosthesis according to a another embodiment of the invention, wherein a second layer of a polymer liner (forming the whole of an articular surface layer of the cup) has been moulded separately to a first layer of the polymer liner, just prior to insertion of the second layer into the first layer.

FIG. 32 shows a perspective view of an acetabular cup prosthesis 270 according to a yet further embodiment of the invention. The cup 270 is essentially formed as described above in relation FIG. 31. However, in this case, the second layer 272 is configured to form the whole of the articular surface layer of the polymer liner 254. Thus, the first layer 274 in this embodiment does not include a recess, as such, but rather is arranged to be thinner than the desired polymer liner 254 thickness so as to accommodate the second layer 272.

It will be understood that an advantage of employing the methods described above in relation to FIGS. 31 and 32 is that they ensure that the polymer powder of the second layer does not accumulate in the pole of the cup thereby producing a thicker than intended layer of cross-linked polymer at the pole and a thinner than intended layer of cross-linked polymer at the periphery of the cup (i.e. in the intended wear zone).

In a further embodiment of the present invention, a polymer component was formed by blending Ticona GUR 1020 polyethylene resin powder with varying amounts of antioxidant in the form of vitamin E (DSM dl alpha Tocopherol). For comparison, a first sample was created with no vitamin E, a second sample was coated with 0.1% by weight of vitamin E and a third sample was coated with 2.0% by weight of vitamin E.

All three samples were packaged in special packets made from PET film, aluminium foil, adhesive layers and polyethylene film to keep the samples separated from the atmosphere. Oxygen was removed from the internal aspect of each of the packets after they were filled with the samples by a sequence of vacuum, nitrogen gas flush, vacuum and finally sealing of the packets. Irradiation of each sample was performed by gamma irradiation at Isotron UK at a dose rate of less than 5 kGy per hour to provide a total dose of 100 kGy. Compression moulding of each sample into consolidated blocks was performed using a bespoke mould at 230 degrees C. at Orthoplastics UK. The consolidated blocks were conditioned for 24 hours at 23 degrees C. prior to machining of test specimens from the blocks according to FRM-PRD-003. Oxidation in the consolidated specimens was measured using infrared spectroscopy according to ASTM F2102-01(2001) and a graph of the results is shown in FIG. 33.

Figure 33:
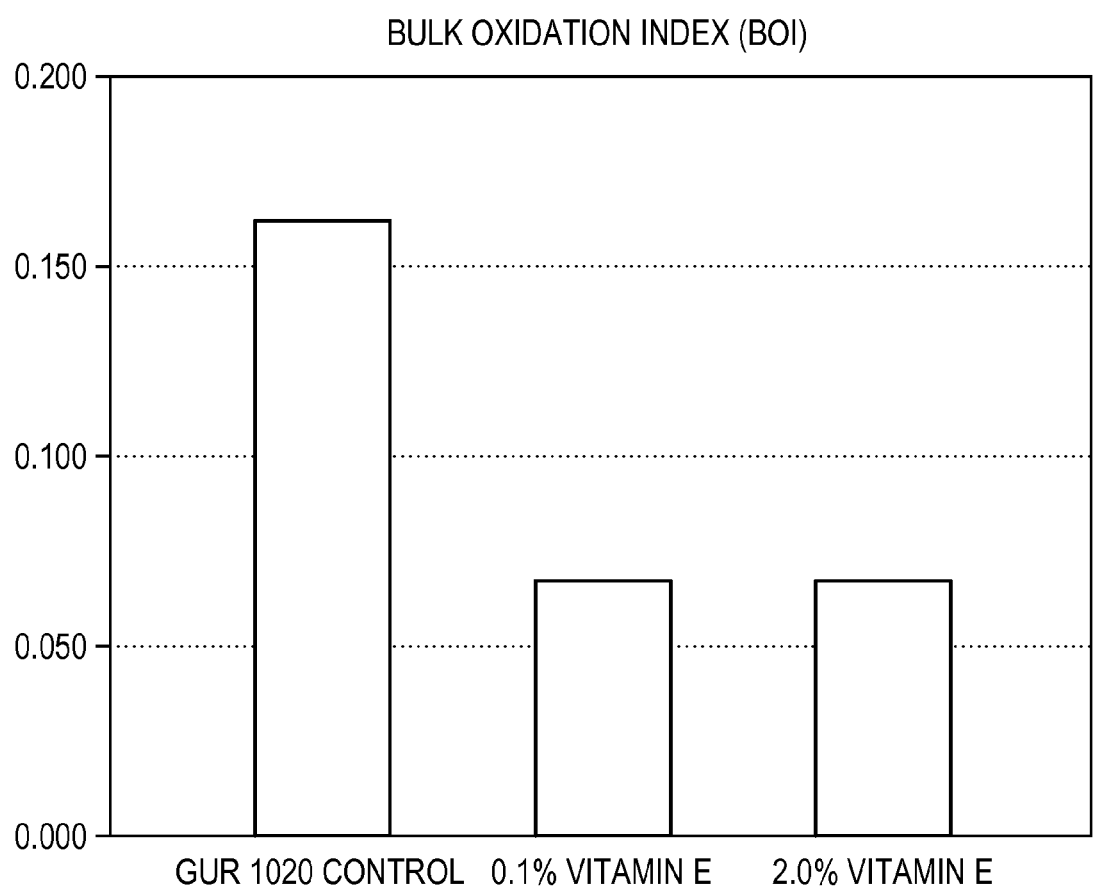
FIG. 33 shows a graph of the Bulk Oxidation Index (BOI) for three test samples to compare the oxidation levels of a standard polymer component with those formed according to embodiments of the present invention.

It can be seen from FIG. 33 that irradiating polyethylene resin without a coating of antioxidant resulted in significant oxidation (greater than 0.15%) of the bulk consolidated material, despite the irradiation being carried out in a reduced Oxygen environment. It is regarded in the orthopaedic industry that levels of oxidation above 0.1% (i.e. above 0.100 on the BOI) are unacceptable for use as an orthopaedic implant. With 0.1% vitamin E added to the polyethylene, the bulk oxidation index is reduced to an acceptable level of approximately 0.07%. Blending in 2.0% vitamin E reduces the oxidation index even further, to approximately 0.015%. Thus, it can be seen that using the method of the present invention, it is possible to produce cross-linked polymer components having an acceptable level of oxidation.

Figure 34A:
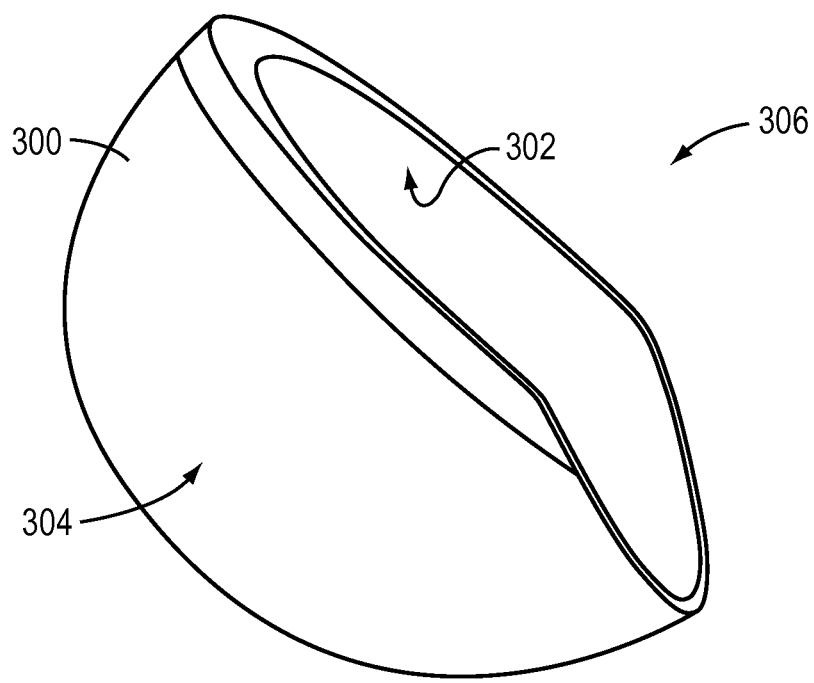
FIG. 34A shows a side perspective view of a one-piece acetabular cup prosthesis according to an embodiment of the present invention in which the centre of the inner surface has been displaced with respect to the outer surface and a cut-out provided at an inferior edge.
Figure 34B:
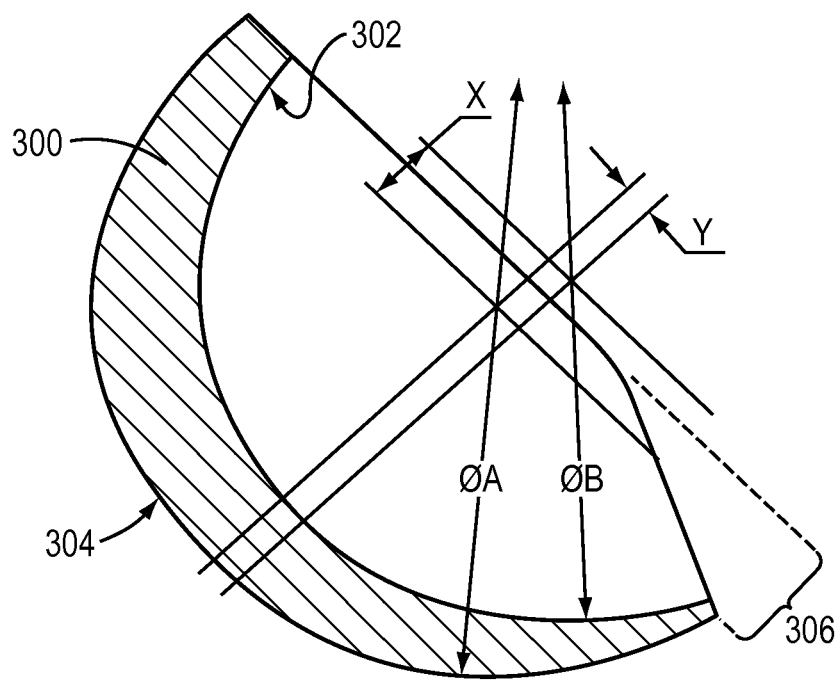
FIG. 34B shows a cross-sectional view through the one-piece acetabular cup prosthesis of FIG. 34A.

FIGS. 34A and 34B show a metal one-piece acetabular cup prosthesis 300 according to a further embodiment of the present invention in which the centre of the inner surface 302 has been displaced with respect to the outer surface 304 and a cut-out 306 is provided at an inferior edge.

In this particular embodiment, the inner centre has been displaced outwards by 7 mm and downwards (i.e. inferiorly) by 2 mm This allows a 54 mm inner diameter (instead of the normal 50 mm inner diameter associated with a standard 56 mm outer diameter cup). Accordingly, it is possible to achieve a 2 mm inner diameter to outer diameter difference so that a larger than normal femoral head (e.g. 54 mm rather than 50 mm) can be employed without increasing the size of the cup 300. This therefore helps to ensure better wear and load characteristics without requiring the removal of any additional bone.

Figure 35A:
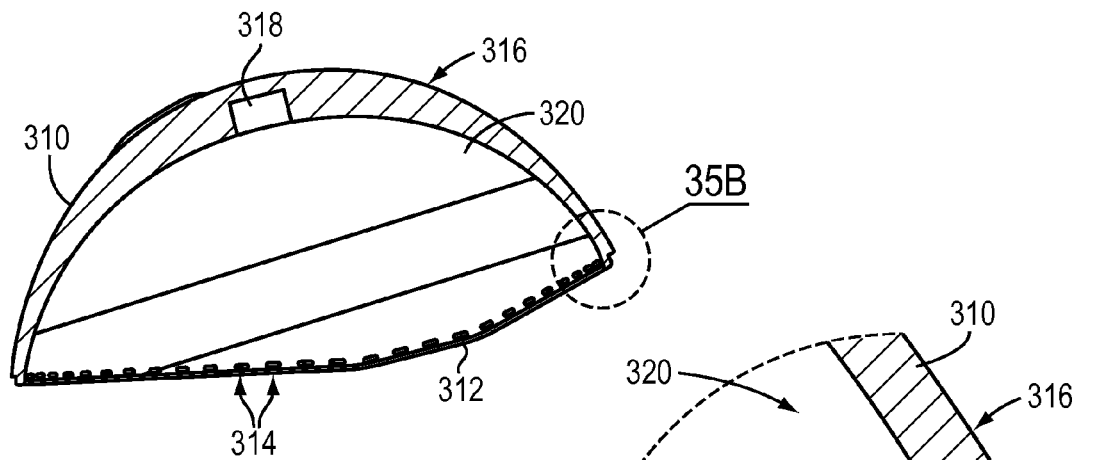
FIG. 35A shows a cross-sectional view through a metal acetabular cup shell, showing a series of holes through an edge rim of the shell, in accordance with an embodiment of the present invention.
Figure 35B:
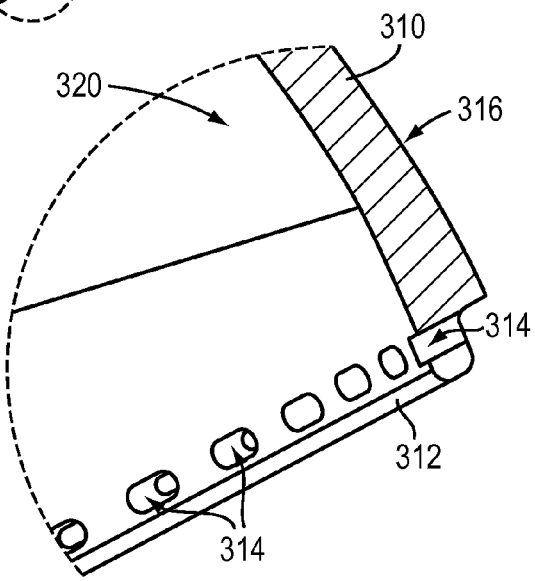
FIG. 35B shows an enlarged view of an edge portion of the metal shell of FIG. 35A, showing that the cross-section has been taken through one of the holes.

FIGS. 35A and 35B show a metal acetabular cup shell 310 having a rim 312 around the whole the cup edge. The rim 312 is perforated with a plurality of holes 314 therethrough. As clearly shown in FIG. 35B, the rim 312 is inset from the external surface 316 of the shell 310. The shell 310 also comprises a threaded blind bore 318 located at the pole of the cup, on the interior surface 320.

Figure 36A:
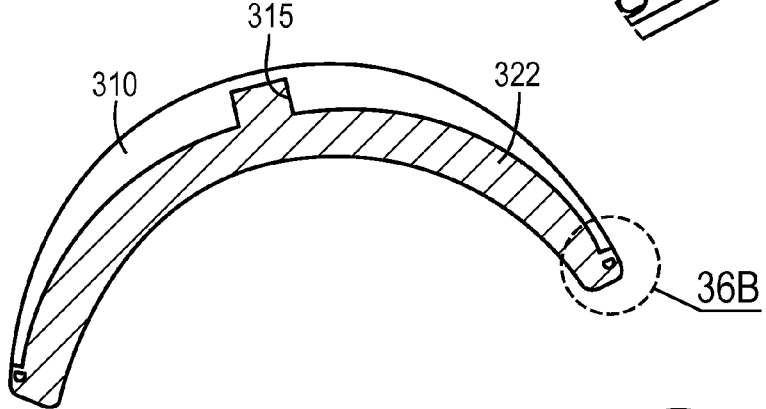
FIG. 36A shows a cross-sectional view of the shell of FIGS. 35A and 35B after a polymer liner has been compression moulded therein.
Figure 36B:
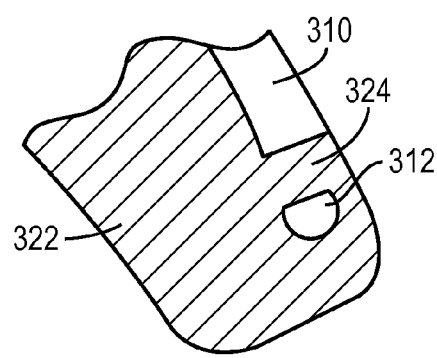
FIG. 36B shows an enlarged view of an edge portion of the cup of FIG. 36A, showing the polymer liner extending through the exposed hole in the metal shell.

As shown in FIGS. 36A and 36B, a polymer inner liner 322 is compression moulded in the shell 310 such that threads 324 of the polymer liner 322 are formed through the holes 314 in the rim 312 and then moulded into the polymer which is arranged to envelope the rim 312 to thereby stitch the edge of the liner 322 to the shell 310. In addition, the polymer liner 322 is moulded into the threaded hole 31/8 of the shell 310 to provide a macro fixation means and the inner surface 320 of the shell 310 is roughened for micro-attachment of the polymer liner 322.

Figure 37A:
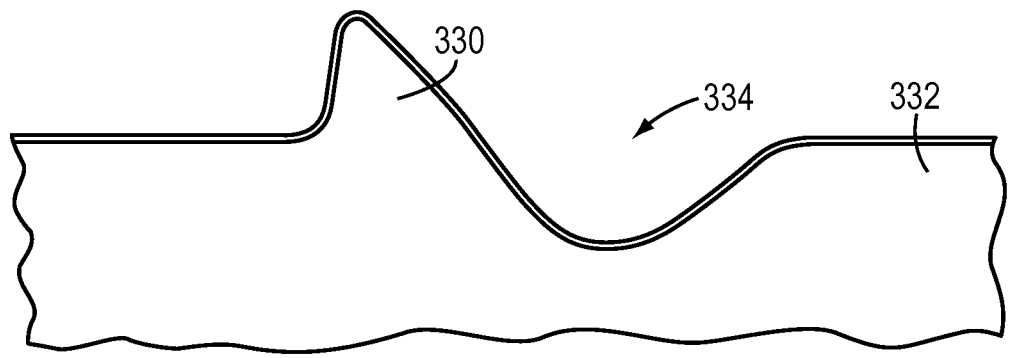
FIG. 37A shows an enlarged cross-sectional view of a spike created in an external surface of a metal acetabular cup shell, in accordance with an embodiment of the present invention.

FIG. 37A shows an enlarged cross-sectional view of a spike 330 created in an external surface 332 of a metal acetabular cup shell, in accordance with an embodiment of the present invention. The spike 330 is created using e-beam sculpturing. Thus, the e-beam is initially focused to melt a small droplet of metal on the surface 332 and then the e-beam is moved a small distance along the surface 332 to push the droplet of metal out of the melt pool 334 to form the adjacent spike 330. This process is repeated a number of times at different locations on the surface 332 of the shell to create a series of spikes 330 forming a rough exterior for initial fixation.

Figure 37B:
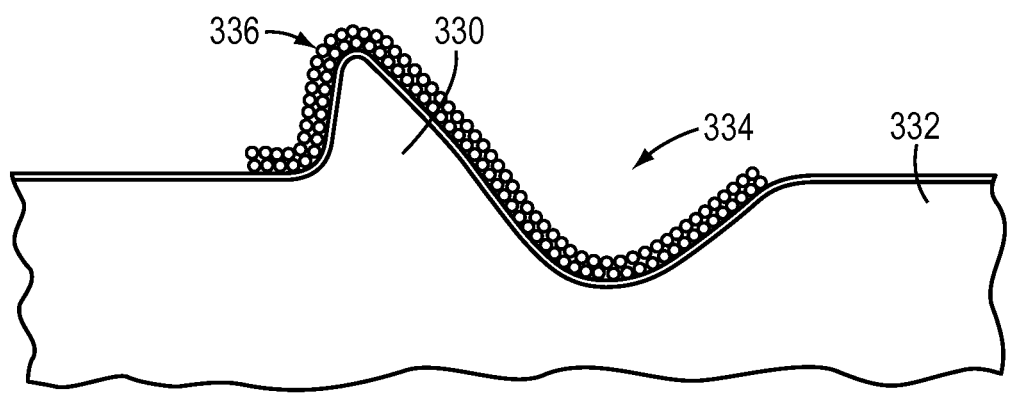
FIG. 37B shows a view similar to that of FIG. 37A but after a vacuum plasma sprayed metal coating has been applied to the spiky surface.

In certain embodiments, a vacuum plasma sprayed titanium coating 336 is then applied to the spiky surface 332 to substantially cover the surface 332, as illustrated in FIG. 37B. It will be understood that the titanium coating 336 provides the surface 332 with undercuts and a good pore size to promote bone in-growth for longer-term fixation.

It is also noted that the provision of the spikes 330 helps to ensure that the titanium particles of the coating 336 are not dislodged by shear forces when the cup is inserted into a patient.

It will be appreciated by persons skilled in the art that various modifications may be made to the above embodiments without departing from the scope of the present invention. In particular, one or more features from a first embodiment may be mixed and matched with one or more features from a second or subsequent embodiment.

The invention claimed is:

1. An acetabular cup prosthesis comprising a metal outer shell and a polymer inner liner, wherein an attachment means is provided which (i) projects from or through a terminal edge of the polymer liner and (ii) is configured for attachment of the cup to an introducer configured for insertion of the cup into a patient.

2. The acetabular cup prosthesis according to claim 1 wherein the attachment means is sloped or curved inwardly towards the centre of the cup.

3. The acetabular cup prosthesis according to claim 1 wherein the attachment means projects from the terminal edge of the polymer liner and is formed as an integral part of the polymer liner.

4. The acetabular cup prosthesis according to claim 1 wherein the attachment means projects through the terminal edge of the polymer liner and is formed as an integral part of the metal shell.

5. The acetabular cup prosthesis according to claim 1 wherein the attachment means is joined to the metal shell or polymer liner by melting or gluing or by mechanical means such as by small loops.

6. The acetabular cup prosthesis according to claim 1 wherein the attachment means comprises one or more loops having a first end and a second end secured to the liner of the cup and projecting from the terminal edge of the liner.

7. The acetabular cup prosthesis according to claim 6 wherein the loops are thickest at their first and second ends so as to provide more support at these joints.

8. The acetabular cup prosthesis according to claim 1 wherein the attachment means comprises one or more projections having a serrated surface.

9. The acetabular cup prosthesis according to claim 1 wherein the attachment means comprises one or more projections having a device configured to lock onto a serrated surface.

10. The acetabular cup prosthesis according to claim 9 wherein the device is configured to allow the serrated surface to be passed through it in one direction but to prevent the serrated surface from passing through it in the opposite direction.

11. The acetabular cup prosthesis according to claim 1 wherein the attachment means comprises one or more projections in the form of fingers or straps.

12. The acetabular cup prosthesis according to claim 1 wherein the attachment means comprises one or more rods.

13. An acetabular cup prosthesis comprising a metal outer shell and a polymer inner liner, wherein an attachment means is provided which projects from or through the polymer liner for attachment of the cup to an introducer configured for insertion of the cup into a patient,
wherein (i) the attachment means comprises one or more rods, and (ii) the rods are provided with an enlarged portion at their free ends configured for gripping by an introducer.

14. The acetabular cup prosthesis according to claim 13 wherein the enlarged portion is spherical.

15. The acetabular cup prosthesis according to claim 13 wherein the enlarged portion is generally conical and orientated with its tip at the free end of the rod.

16. The acetabular cup prosthesis according to claim 13 wherein the enlarged portion comprises two or more conical portions stacked with their tips all towards the free end of the rod.

17. An acetabular cup prosthesis comprising a metal outer shell and a polymer inner liner, wherein an attachment means is provided which projects from or through the polymer liner for attachment of the cup to an introducer configured for insertion of the cup into a patient,
wherein (i) the attachment means comprises one or more rods, and (ii) the rods include a neck configured such that rotation of the rod with respect to the inner liner and/or outer shell will cause the rod to shear at the neck.

18. The acetabular cup prosthesis according to claim 17 wherein the rods are configured as extensions of the polymer liner, and project from the terminal edge of the polymer liner, and the location of the neck is close to the base of each rod.

19. The acetabular cup prosthesis according to claim 17 wherein the rods are configured as extensions of the metal shell, and project through the terminal edge of the polymer liner, and the location of the neck is below the height of the polymer liner through which it extends.

* * * * *